US012755838B2

(12) United States Patent
Dunstan et al.

(10) Patent No.: US 12,755,838 B2
(45) Date of Patent: Oct. 6, 2026

(54) SENIOR LIVING ENGAGEMENT AND CARE SUPPORT PLATFORMS

(71) Applicant: State Farm Mutual Automobile Insurance Company, Bloomington, IL (US)

(72) Inventors: Stephen Dunstan, Tempe, AZ (US); Kami LaVallier, Pekin, IL (US); Edward P. Matesevac, Normal, IL (US); Mary Kay Mueller, Normal, IL (US); Vallory Clardy, Fremont, CA (US); Matthew Morrison, Mesa, AZ (US); Nirav Patel, Plano, TX (US); Francesco Radicati, Palo Alto, CA (US); Beth Ann Snell, Anchor, IL (US); Cara Lawlor Quigley, Bloomington, IL (US); Caroline Mead, Bloomington, IL (US); Kelsey Schachter, Bloomington, IL (US); Brea Dutt, Bloomington, IL (US); Lindsay Meyer, Bloomington, IL (US); Leny Santana, Bloomington, IL (US); Marta Coleman, Bloomington, IL (US); Christine Pizzo, Bloomington, IL (US)

(73) Assignee: State Farm Mutual Automobile Insurance Company, Bloomington, IL (US)

( * ) Notice: Subject to any disclaimer, the term of this patent is extended or adjusted under 35 U.S.C. 154(b) by 0 days.

(21) Appl. No.: 19/228,669

(22) Filed: Jun. 4, 2025

(65) Prior Publication Data

US 2025/0299816 A1 Sep. 25, 2025

Related U.S. Application Data

(63) Continuation of application No. 18/417,752, filed on Jan. 19, 2024, now Pat. No. 12,354,746, which is a (Continued)

(51) Int. Cl.
*G16H 40/67* (2018.01)
*G06F 3/16* (2006.01)
(Continued)

(52) U.S. Cl.
CPC ............ *G16H 40/67* (2018.01); *G06F 3/167* (2013.01); *G16H 10/60* (2018.01); *G16H 80/00* (2018.01); *H04L 5/02* (2013.01); *H04L 51/02* (2013.01)

(58) Field of Classification Search
CPC .............................. G16H 80/00; G16H 40/67
See application file for complete search history.

(56) References Cited

U.S. PATENT DOCUMENTS

| | | | |
|---|---|---|---|
| 1,446,000 | A | 2/1923 | Cleland |
| 5,553,609 | A | 9/1996 | Chen et al. |

(Continued)

FOREIGN PATENT DOCUMENTS

| | | | |
|---|---|---|---|
| CA | 2781251 | A1 | 12/2013 |
| IN | 201811043670 | A | 12/2018 |

(Continued)

OTHER PUBLICATIONS

Aicha, A.N. et al., "Continuous measuring of the indoor walking speed of older adults living alone", J Ambient Intell Human Comput, 2018, 9:589-599, 11 p.

(Continued)

*Primary Examiner* — Joseph D Burgess
(74) *Attorney, Agent, or Firm* — Armstrong Teasdale LLP

(57) ABSTRACT

Provided herein is an engagement and care support platform ("ECSP") computer system including at least one processor in communication with at least one memory device for facilitating senior user engagement. The processor is programmed to: (i) register a user through an application, (ii) register a caregiver associated with the user through the (Continued)

application, (iii) generate a senior profile based upon user personal and scheduling data, (iv) build a daily interactive user interface that reflects the senior profile, (v) display the daily interactive user interface at a first client device associated with the user, (vi) cause the first client device to initiate a daily interaction prompt to the user, (vii) determine whether any user interaction was received in response to the daily interaction prompt, and (viii) transmit a daily update message to a second client device associated with the caregiver, including an indication of whether any user interaction was received.

20 Claims, 26 Drawing Sheets

Related U.S. Application Data continuation of application No. 17/461,627, filed on Aug. 30, 2021, now Pat. No. 11,901,071, which is a continuation of application No. 17/324,993, filed on May 19, 2021, now Pat. No. 11,107,581, which is a continuation of application No. 17/038,738, filed on Sep. 30, 2020, now Pat. No. 11,056,235, which is a continuation of application No. 16/996,592, filed on Aug. 18, 2020.

(60) Provisional application No. 63/041,409, filed on Jun. 19, 2020, provisional application No. 62/935,860, filed on Nov. 15, 2019, provisional application No. 62/935,854, filed on Nov. 15, 2019, provisional application No. 62/892,207, filed on Aug. 27, 2019, provisional application No. 62/888,746, filed on Aug. 19, 2019.

(51) Int. Cl.

*G16H 10/60* (2018.01)
*G16H 80/00* (2018.01)
*H04L 5/02* (2006.01)
*H04L 51/02* (2022.01)

(56) References Cited

U.S. PATENT DOCUMENTS 5,703,995 A 12/1997 Willbanks
5,935,251 A 8/1999 Moore
5,967,975 A 10/1999 Ridgeway
6,428,475 B1 8/2002 Shen
6,611,206 B2 8/2003 Eshelman et al.
6,847,892 B2 1/2005 Zhou et al.
6,886,139 B2 4/2005 Liu
7,091,865 B2 8/2006 Cuddihy et al.
7,154,399 B2 12/2006 Cuddihy et al.
7,242,305 B2 7/2007 Cuddihy et al.
7,289,965 B1 10/2007 Bradley et al.
7,301,463 B1 11/2007 Paterno
7,397,346 B2 7/2008 Helal et al.
7,411,510 B1 8/2008 Nixon
7,498,985 B1 3/2009 Woo et al.
7,502,498 B2 3/2009 Wen et al.
7,562,121 B2 7/2009 Berisford et al.
7,586,418 B2 9/2009 Cuddihy et al.
7,733,224 B2 6/2010 Tran
7,801,612 B2 9/2010 Johnson et al.
7,831,235 B2 11/2010 Mononen et al.
7,835,919 B1 11/2010 Bradley et al.
7,835,926 B1 11/2010 Naidoo et al.
7,865,386 B2 1/2011 Sarkar
7,911,334 B2 3/2011 Busey
7,966,203 B1 6/2011 Pietrzak
7,966,378 B2 6/2011 Berisford et al.
7,974,854 B1 7/2011 Bradley et al.
8,010,377 B1 8/2011 Bradley et al.
8,019,622 B2 9/2011 Kaboff et al.
8,027,850 B1 9/2011 Pietrzak
8,050,665 B1 11/2011 Orbach
8,131,875 B1 3/2012 Chen et al.
8,214,082 B2 7/2012 Tsai et al.
8,346,594 B2 1/2013 Begeja et al.
8,490,006 B1 7/2013 Reeser et al.
8,527,306 B1 9/2013 Reeser et al.
8,529,456 B2 9/2013 Cobain
8,533,144 B1 9/2013 Reeser et al.
8,589,806 B1 11/2013 Sena
8,640,038 B1 1/2014 Reeser et al.
8,650,048 B1 2/2014 Hopkins, III et al.
8,655,595 B1 2/2014 Green et al.
8,665,084 B2 3/2014 Shapiro et al.
8,669,864 B1 3/2014 Tedesco et al.
8,670,998 B2 3/2014 Bertha et al.
8,675,920 B2 3/2014 Hanson et al.
8,676,833 B2 3/2014 Chunilal
8,682,682 B1 3/2014 Bradley et al.
8,682,952 B2 3/2014 Kutzik et al.
8,744,901 B2 6/2014 Begeja et al.
8,760,285 B2 6/2014 Billman et al.
8,803,690 B2 8/2014 Junqua et al.
8,856,383 B2 10/2014 Beninato et al.
8,868,616 B1 10/2014 Otto et al.
8,882,666 B1 11/2014 Goldberg et al.
8,890,680 B2 11/2014 Reeser et al.
8,917,186 B1 12/2014 Grant
8,929,853 B2 1/2015 Butler
8,965,327 B2 2/2015 Davis et al.
8,976,937 B2 3/2015 Shapiro et al.
9,049,168 B2 6/2015 Jacob et al.
9,057,746 B1 6/2015 Houlette et al.
9,117,349 B2 8/2015 Shapiro et al.
9,142,119 B1 9/2015 Grant
9,152,737 B1 10/2015 Micali et al.
9,165,334 B2 10/2015 Simon
9,183,578 B1 11/2015 Reeser et al.
9,202,363 B1 12/2015 Grant
9,208,661 B2 12/2015 Junqua et al.
9,213,994 B2 12/2015 Green et al.
9,262,909 B1 2/2016 Grant
9,286,772 B2 3/2016 Shapiro et al.
9,344,330 B2 5/2016 Jacob et al.
9,349,300 B2 5/2016 Harkness
9,375,142 B2 6/2016 Schultz et al.
9,408,561 B2 8/2016 Stone et al.
9,424,737 B2 8/2016 Bailey et al.
9,443,195 B2 9/2016 Micali et al.
9,472,092 B1 10/2016 Grant
9,491,277 B2 11/2016 Vincent
9,536,052 B2 1/2017 Amarasingham et al.
9,585,563 B2 3/2017 Mensinger et al.
9,589,441 B2 3/2017 Shapiro et al.
9,609,003 B1 3/2017 Chmielewski et al.
9,665,892 B1 5/2017 Reeser et al.
9,666,060 B2 5/2017 Reeser et al.
9,699,529 B1 7/2017 Petri et al.
9,712,576 B1 7/2017 Gill
9,739,813 B2 8/2017 Houlette et al.
9,754,477 B2 9/2017 Poder et al.
9,767,680 B1 9/2017 Trundle
9,786,158 B2 10/2017 Beaver et al.
9,798,979 B2 10/2017 Fadell et al.
9,798,993 B2 10/2017 Payne et al.
9,800,570 B1 10/2017 Bleisch
9,800,958 B1 10/2017 Petri et al.
9,801,541 B2 10/2017 Mensinger et al.
9,812,001 B1 11/2017 Grant
9,838,854 B2 12/2017 Fretwell
9,866,507 B2 1/2018 Frenkel et al.
9,888,371 B1 2/2018 Jacob
9,892,463 B1 2/2018 Hakimi-Boushehri et al.
9,898,168 B2 2/2018 Shapiro et al.
9,898,912 B1 2/2018 Jordan et al.
9,901,252 B2 2/2018 Tran

(56) References Cited

U.S. PATENT DOCUMENTS 9,911,042 B1 3/2018 Cardona et al.
9,922,524 B2 3/2018 Devdas et al.
9,923,971 B2 3/2018 Madey et al.
9,936,076 B1 4/2018 Tanner
9,942,630 B1 4/2018 Petri et al.
9,947,202 B1 4/2018 Moon et al.
9,978,033 B1 5/2018 Payne et al.
9,996,882 B1 6/2018 Manzella et al.
9,997,056 B2 6/2018 Bleisch
10,002,295 B1 6/2018 Cardona et al.
10,022,084 B2 7/2018 Nonaka et al.
10,042,341 B1 8/2018 Jacob
10,043,369 B2 8/2018 Hopkins et al.
10,047,974 B1 8/2018 Riblet et al.
10,055,793 B1 8/2018 Call et al.
10,055,803 B2 8/2018 Orduna et al.
10,057,664 B1 8/2018 Moon et al.
10,073,929 B2 9/2018 Vaynriber et al.
10,102,584 B1 10/2018 Devereaux et al.
10,102,585 B1 10/2018 Bryant et al.
10,102,589 B1 10/2018 Tofte et al.
10,107,708 B1 10/2018 Schick et al.
10,136,294 B2 11/2018 Mehta et al.
10,140,666 B1 11/2018 Wang et al.
10,142,394 B2 11/2018 Chmielewski et al.
10,147,296 B2 12/2018 Gregg
10,152,150 B2 12/2018 Sherman
10,176,705 B1 1/2019 Grant
10,181,160 B1 1/2019 Hakimi-Boushehri et al.
10,181,246 B1 1/2019 Jackson
10,186,134 B1 1/2019 Moon et al.
10,198,771 B1 2/2019 Madigan et al.
10,204,500 B2 2/2019 Cullin et al.
10,206,630 B2 2/2019 Stone et al.
10,217,068 B1 2/2019 Davis et al.
10,223,751 B1 3/2019 Hutchinson et al.
10,226,187 B2 3/2019 Al-Ali et al.
10,226,204 B2 3/2019 Heaton et al.
10,229,394 B1 3/2019 Davis et al.
10,244,294 B1 3/2019 Moon et al.
10,249,158 B1 4/2019 Jordan et al.
10,258,295 B2 4/2019 Fountaine
10,282,787 B1 5/2019 Hakimi-Boushehri et al.
10,282,788 B1 5/2019 Jordan, II et al.
10,282,961 B1 5/2019 Jordan, II et al.
10,295,431 B1 5/2019 Schick et al.
10,296,978 B1 5/2019 Corder et al.
10,297,138 B2 5/2019 Reeser et al.
10,298,735 B2 5/2019 Preston et al.
10,304,311 B2 5/2019 Clark et al.
10,304,313 B1 5/2019 Moon et al.
10,319,209 B2 6/2019 Carlton-Foss
10,323,860 B1 6/2019 Riblet et al.
10,325,471 B1 6/2019 Victor
10,325,473 B1 6/2019 Moon et al.
10,332,059 B2 6/2019 Matsuoka et al.
10,335,059 B2 7/2019 Annegarn et al.
10,346,811 B1 7/2019 Jordan, II et al.
10,353,359 B1 7/2019 Jordan, II et al.
10,356,303 B1 7/2019 Jordan, II et al.
10,360,345 B2 7/2019 Ramsdell et al.
10,373,257 B1 8/2019 Iqbal et al.
10,380,692 B1 8/2019 Parker et al.
10,387,966 B1 8/2019 Shah et al.
10,388,135 B1 8/2019 Jordan, II et al.
10,412,169 B1 9/2019 Madey et al.
10,446,000 B2 10/2019 Friar et al.
10,446,007 B2 10/2019 Kawazu et al.
10,453,149 B1 10/2019 Gaudin et al.
10,467,476 B1 11/2019 Cardona et al.
10,475,141 B2 11/2019 Mcintosh et al.
10,480,825 B1 11/2019 Riblet et al.
10,482,746 B1 11/2019 Moon et al.
10,506,411 B1 12/2019 Jacob
10,506,990 B2 12/2019 Lee et al.
10,510,120 B1 12/2019 Roll
10,514,669 B1 12/2019 Call et al.
10,515,372 B1 12/2019 Jordan, II et al.
10,522,009 B1 12/2019 Jordan, II et al.
10,522,021 B1 12/2019 Victor
10,546,478 B1 1/2020 Moon et al.
10,547,918 B1 1/2020 Moon et al.
10,548,512 B2 2/2020 Hausdorff et al.
10,565,541 B2 2/2020 Payne et al.
10,572,947 B1 2/2020 Berends et al.
10,573,146 B1 2/2020 Jordan, II et al.
10,573,149 B1 2/2020 Jordan, II et al.
10,579,028 B1 3/2020 Jacob
10,586,177 B1 3/2020 Choueiter et al.
10,607,295 B1 3/2020 Hakimi-Boushehri et al.
10,621,686 B2 4/2020 Mazar et al.
10,623,790 B2 4/2020 Maddalena
10,634,576 B1 4/2020 Schick et al.
10,664,922 B1 5/2020 Madigan et al.
10,679,292 B1 6/2020 Call et al.
10,685,402 B1 6/2020 Bryant et al.
10,699,346 B1 6/2020 Corder et al.
10,726,494 B1 7/2020 Shah et al.
10,726,500 B1 7/2020 Shah et al.
10,733,671 B1 8/2020 Hakimi-Boushehri et al.
10,733,868 B2 8/2020 Moon et al.
10,735,829 B2 8/2020 Petri et al.
10,740,691 B2 8/2020 Choueiter et al.
10,741,033 B1 8/2020 Jordan, II et al.
10,750,252 B2 8/2020 Petri et al.
10,795,329 B1 10/2020 Jordan, II et al.
10,796,557 B2 10/2020 Sundermeyer et al.
10,810,574 B1 10/2020 Wilson et al.
10,823,458 B1 11/2020 Riblet et al.
10,824,971 B1 11/2020 Davis et al.
10,825,318 B1 11/2020 Williams et al.
10,825,320 B1 11/2020 Moon et al.
10,825,321 B2 11/2020 Moon et al.
10,832,225 B1 11/2020 Davis et al.
10,846,800 B1 11/2020 Bryant et al.
10,878,062 B1 12/2020 Garavaglia et al.
10,922,756 B1 2/2021 Call et al.
10,922,948 B1 2/2021 Moon et al.
10,930,141 B2 2/2021 De Paz Alberola et al.
10,943,306 B1 3/2021 Gaudin et al.
10,943,447 B1 3/2021 Jordan, II et al.
10,949,928 B1 3/2021 Roll
10,970,990 B1 4/2021 Jacob
10,990,069 B1 4/2021 Jacob
11,003,334 B1 5/2021 Conway et al.
11,004,320 B1 5/2021 Jordan, II et al.
11,015,997 B1 5/2021 Schick et al.
11,017,480 B2 5/2021 Shah et al.
11,024,142 B2 6/2021 Tunnell et al.
11,042,137 B1 6/2021 Call et al.
11,042,942 B1 6/2021 Hakimi-Boushehri et al.
11,043,098 B1 6/2021 Jordan, II et al.
11,049,078 B1 6/2021 Jordan, II et al.
11,049,189 B2 6/2021 Shah et al.
11,056,235 B2 7/2021 Dunstan et al.
11,070,644 B1 7/2021 Teng et al.
11,074,659 B1 7/2021 Hakimi-Boushehri et al.
11,094,180 B1 8/2021 Williams et al.
11,100,594 B1 8/2021 West et al.
11,107,465 B2 8/2021 Gustman et al.
11,118,812 B1 9/2021 Riblet et al.
11,120,226 B1 9/2021 Nudd et al.
11,126,708 B2 9/2021 Reimer
11,151,654 B2 10/2021 Trainor et al.
11,188,840 B1 11/2021 Rivera et al.
11,232,873 B1 1/2022 Aspro et al.
11,301,502 B1 4/2022 Dijamco et al.
11,308,247 B2 4/2022 McDade
11,393,585 B2 7/2022 Dunstan et al.
11,394,799 B2 7/2022 Jackson
11,431,660 B1 8/2022 Leeds et al.
11,436,549 B1 9/2022 Hull et al.
11,556,995 B1 1/2023 Little et al.
11,581,099 B1 2/2023 Rufo et al.

(56) References Cited

U.S. PATENT DOCUMENTS 11,587,555 B1 2/2023 Pathak
11,688,516 B2 6/2023 Harr et al.
11,715,074 B2 8/2023 Aspro et al.
11,783,423 B1 10/2023 Yager et al.
11,853,919 B1 12/2023 Mangat et al.
11,941,712 B2 3/2024 Trundle
2002/0046047 A1 4/2002 Budd
2002/0116256 A1 8/2002 De Rafael et al.
2002/0169631 A1 11/2002 Lewis
2002/0194048 A1 12/2002 Levinson
2003/0001742 A1 1/2003 Eshelman et al.
2003/0023459 A1 1/2003 Shipon
2003/0144793 A1 7/2003 Melaku et al.
2004/0030531 A1 2/2004 Miller et al.
2004/0078220 A1 4/2004 Jackson
2004/0220538 A1 11/2004 Panopoulos
2004/0249250 A1 12/2004 McGee et al.
2005/0137465 A1 6/2005 Cuddihy et al.
2005/0142524 A1 6/2005 Simon et al.
2005/0174242 A1 8/2005 Cohen
2005/0228245 A1 10/2005 Quy
2006/0143060 A1 6/2006 Conry et al.
2006/0205564 A1 9/2006 Peterson
2006/0293924 A1 12/2006 Gardiner
2007/0088507 A1 4/2007 Haberlen et al.
2007/0186165 A1 8/2007 Maislos et al.
2007/0214002 A1 9/2007 Smith et al.
2007/0250791 A1 10/2007 Halliday et al.
2007/0260401 A1 11/2007 Sydor et al.
2007/0274464 A1 11/2007 Cameron et al.
2007/0282476 A1 12/2007 Song et al.
2008/0084296 A1 4/2008 Kutzik et al.
2008/0154099 A1 6/2008 Aspel et al.
2008/0201174 A1 8/2008 Ramasubramanian et al.
2008/0235629 A1 9/2008 Porter et al.
2008/0240379 A1 10/2008 Maislos et al.
2008/0292151 A1 11/2008 Kurtz et al.
2008/0294462 A1 11/2008 Nuhaan et al.
2008/0294490 A1 11/2008 Nuhaan et al.
2009/0010106 A1 1/2009 Levy
2009/0012373 A1 1/2009 Raij et al.
2009/0048865 A1 2/2009 Breazeale, Jr.
2009/0177500 A1 7/2009 Swahn
2009/0259492 A1 10/2009 Cossman
2009/0265185 A1 10/2009 Finn et al.
2009/0265193 A1 10/2009 Collins et al.
2009/0281393 A1 11/2009 Smith
2009/0315735 A1 12/2009 Bhavani et al.
2009/0326981 A1 12/2009 Karkanias et al.
2010/0017718 A1 1/2010 Bohms
2010/0145164 A1 6/2010 Howell
2010/0191824 A1 7/2010 Lindsay
2010/0198608 A1 8/2010 Kaboff et al.
2010/0217619 A1 8/2010 Cox et al.
2010/0222649 A1 9/2010 Schoenberg
2010/0286490 A1 11/2010 Koverzin
2010/0306824 A1 12/2010 Gurney et al.
2011/0021140 A1 1/2011 Binier
2011/0047086 A1 2/2011 Heisterkamp et al.
2011/0092779 A1 4/2011 Chang et al.
2011/0125844 A1 5/2011 Collier et al.
2011/0181422 A1 7/2011 Tran
2011/0201901 A1 8/2011 Khanuja
2011/0202345 A1 8/2011 Meyer et al.
2011/0224501 A1 9/2011 Hudsmith
2011/0246123 A1 10/2011 DelloStritto et al.
2012/0095846 A1 4/2012 Leverant
2012/0143619 A1 6/2012 Routt
2012/0191788 A1 7/2012 Mellen
2012/0197662 A1 8/2012 Sun et al.
2012/0254021 A1 10/2012 Wohied et al.
2012/0280811 A1 11/2012 McKalip et al.
2012/0284040 A1 11/2012 Dupin
2012/0284637 A1 11/2012 Boyer et al.
2012/0303404 A1* 11/2012 Nudd .................... G06Q 10/06 705/7.15
2013/0035946 A1 2/2013 Ratan et al.
2013/0065569 A1 3/2013 Leipzig et al.
2013/0073299 A1 3/2013 Warman et al.
2013/0073306 A1 3/2013 Shlain et al.
2013/0080209 A1 3/2013 Begeja et al.
2013/0082842 A1 4/2013 Balazs et al.
2013/0095459 A1 4/2013 Tran
2013/0100268 A1 4/2013 Mihailidis et al.
2013/0110895 A1 5/2013 Valentino et al.
2013/0147899 A1 6/2013 Labhard
2013/0148942 A1 6/2013 Ryan et al.
2013/0191140 A1 7/2013 Fotheringham et al.
2013/0197807 A1 8/2013 Du et al.
2013/0226578 A1 8/2013 Bolton et al.
2013/0262155 A1 10/2013 HinKamp
2013/0267795 A1 10/2013 Cosentino et al.
2013/0275263 A1 10/2013 Carlin, Jr. et al.
2013/0297350 A1 11/2013 Gross et al.
2013/0332959 A1 12/2013 Kothari
2014/0052474 A1 2/2014 Madan et al.
2014/0074454 A1 3/2014 Brown et al.
2014/0108031 A1 4/2014 Ferrara
2014/0129160 A1 5/2014 Tran
2014/0136242 A1 5/2014 Weekes et al.
2014/0136264 A1 5/2014 Kinsey, II
2014/0148733 A1 5/2014 Stone et al.
2014/0188997 A1 7/2014 Schneiderman et al.
2014/0207486 A1 7/2014 Carty et al.
2014/0207492 A1 7/2014 Farooq et al.
2014/0257851 A1 9/2014 Walker et al.
2014/0266669 A1 9/2014 Fadell et al.
2014/0266791 A1 9/2014 Lloyd et al.
2014/0282828 A1 9/2014 Stuntebeck
2014/0284348 A1 9/2014 Cheng
2014/0324757 A1 10/2014 Tabrizi et al.
2014/0358592 A1 12/2014 Wedig et al.
2014/0362213 A1 12/2014 Tseng
2015/0002293 A1 1/2015 Nepo
2015/0006200 A1 1/2015 Chaput et al.
2015/0019262 A1 1/2015 Du et al.
2015/0020170 A1 1/2015 Talley
2015/0077237 A1 3/2015 Chou et al.
2015/0094144 A1 4/2015 Brown et al.
2015/0094830 A1 4/2015 Lipoma et al.
2015/0134343 A1 5/2015 Kluger et al.
2015/0154880 A1 6/2015 Petito et al.
2015/0179040 A1 6/2015 Nishihara et al.
2015/0194032 A1 7/2015 Wright
2015/0213224 A1 7/2015 Amarasingham et al.
2015/0223705 A1 8/2015 Sadhu
2015/0254412 A1 9/2015 Humphrys et al.
2015/0269329 A1 9/2015 Fearon et al.
2015/0288797 A1 10/2015 Vincent
2015/0302331 A1 10/2015 Randall
2015/0302529 A1 10/2015 Jagannathan
2015/0302538 A1 10/2015 Mazar et al.
2015/0312740 A1 10/2015 Li et al.
2015/0356701 A1 12/2015 Gandy et al.
2016/0026354 A1 1/2016 Mcintosh et al.
2016/0027278 A1 1/2016 Mcintosh et al.
2016/0048934 A1 2/2016 Gross
2016/0055595 A1 2/2016 Green et al.
2016/0086255 A1 3/2016 Sainfort et al.
2016/0106627 A1 4/2016 Geman et al.
2016/0110509 A1 4/2016 Girardeau et al.
2016/0140320 A1 5/2016 Moturu et al.
2016/0155163 A1 6/2016 White et al.
2016/0162785 A1 6/2016 Grobman
2016/0171864 A1 6/2016 Ciaramelletti et al.
2016/0174913 A1 6/2016 Somanath et al.
2016/0203444 A1 7/2016 Frank et al.
2016/0210427 A1 7/2016 Mynhier et al.
2016/0210434 A1 7/2016 Al-Sharif
2016/0214571 A1 7/2016 Othmer et al.
2016/0225240 A1 8/2016 Voddhi et al.
2016/0246936 A1 8/2016 Kahn
2016/0259902 A1 9/2016 Feldman et al.

(56) References Cited

U.S. PATENT DOCUMENTS

2016/0275475 A1 9/2016 Lin et al.
2016/0292373 A1 10/2016 Spors et al.
2016/0314514 A1 10/2016 High et al.
2016/0342767 A1 11/2016 Narasimhan et al.
2016/0350721 A1 12/2016 Comerford et al.
2016/0371620 A1 12/2016 Nascenzi et al.
2017/0004273 A1 1/2017 Mbanefo et al.
2017/0004463 A1 1/2017 Stroeh et al.
2017/0004695 A1 1/2017 Brasch et al.
2017/0011188 A1 1/2017 Arshad et al.
2017/0011195 A1 1/2017 Arshad et al.
2017/0024525 A1 1/2017 Walker
2017/0046501 A1 2/2017 Coleman et al.
2017/0094057 A1 3/2017 Naiga et al.
2017/0116384 A1 4/2017 Ghani
2017/0124276 A1 5/2017 Tee
2017/0124277 A1 5/2017 Shlagman
2017/0124526 A1 5/2017 Sanderford et al.
2017/0140486 A1 5/2017 Saxena et al.
2017/0193164 A1 7/2017 Simon et al.
2017/0214758 A1 7/2017 Engel
2017/0221336 A1 8/2017 Ogaz
2017/0228109 A1 8/2017 Zhang et al.
2017/0242886 A1 8/2017 Jolley et al.
2017/0262604 A1 9/2017 Francois
2017/0270260 A1 9/2017 Shetty et al.
2017/0277834 A1 9/2017 Zipnick et al.
2017/0293878 A1 10/2017 Donnelly et al.
2017/0300626 A1 10/2017 Love
2018/0007131 A1 1/2018 Cohn et al.
2018/0032696 A1 2/2018 Rome
2018/0060970 A1 3/2018 Oduor et al.
2018/0068081 A1 3/2018 Salem
2018/0075204 A1 3/2018 Lee et al.
2018/0082184 A1 3/2018 Guo et al.
2018/0153477 A1 6/2018 Nagale et al.
2018/0158080 A1 6/2018 Mehl
2018/0158548 A1 6/2018 Taheri et al.
2018/0177436 A1 6/2018 Chang et al.
2018/0182055 A1 6/2018 Jepson et al.
2018/0194919 A1 7/2018 Wu et al.
2018/0196919 A1 7/2018 Abou Mahmoud et al.
2018/0209806 A1 7/2018 Rakah et al.
2018/0211509 A1 7/2018 Ramaci
2018/0211724 A1 7/2018 Wang
2018/0225649 A1 8/2018 Babar et al.
2018/0255114 A1 9/2018 Dharmaji
2018/0260384 A1 9/2018 Pasupalak et al.
2018/0276710 A1 9/2018 Tietzen et al.
2018/0280245 A1 10/2018 Khalid
2018/0308569 A1 10/2018 Luellen
2018/0315499 A1 11/2018 Appelbaum et al.
2018/0322469 A1 11/2018 Logtenberg
2018/0322947 A1 11/2018 Potts et al.
2018/0325470 A1 11/2018 Fountaine
2018/0336048 A1 11/2018 Zarlengo et al.
2018/0342329 A1* 11/2018 Rufo ...................... G16H 80/00
2018/0344215 A1 12/2018 Ohnemus et al.
2018/0357386 A1 12/2018 Sanjay-Gopal
2018/0365957 A1 12/2018 Wright et al.
2019/0028758 A1 1/2019 Talvensaari et al.
2019/0046039 A1 2/2019 Ramesh et al.
2019/0069154 A1 2/2019 Booth et al.
2019/0080056 A1 3/2019 Das et al.
2019/0083003 A1 3/2019 Lee et al.
2019/0095540 A1 3/2019 Antao et al.
2019/0108841 A1 4/2019 Vergyri et al.
2019/0122522 A1 4/2019 Stefanski et al.
2019/0122760 A1 4/2019 Wang
2019/0133445 A1 5/2019 Eteminan et al.
2019/0156944 A1 5/2019 Eriksson et al.
2019/0180868 A1 6/2019 Makram et al.
2019/0182299 A1 6/2019 Beatrice
2019/0198169 A1 6/2019 T et al.
2019/0205675 A1 7/2019 McGill
2019/0206533 A1 7/2019 Singh et al.
2019/0213557 A1 7/2019 Dotan-Cohen et al.
2019/0228657 A1 7/2019 Sean
2019/0267133 A1 8/2019 Schwarz et al.
2019/0279116 A1 9/2019 Caligor
2019/0279647 A1 9/2019 Jones et al.
2019/0281327 A1 9/2019 Li et al.
2019/0287376 A1 9/2019 Netscher et al.
2019/0287676 A1 9/2019 Kaplan et al.
2019/0318283 A1 10/2019 Kelly et al.
2019/0319813 A1 10/2019 Abu-Ghazaleh
2019/0320900 A1 10/2019 Majmudar
2019/0325502 A1 10/2019 Tovey et al.
2019/0334907 A1 10/2019 Rodden et al.
2019/0362319 A1 11/2019 Yen
2019/0362858 A1 11/2019 Valentino et al.
2019/0388017 A1 12/2019 Keating
2019/0392489 A1 12/2019 Tietzen et al.
2020/0005928 A1 1/2020 Daniel
2020/0019852 A1 1/2020 Yoon et al.
2020/0020165 A1 1/2020 Tran et al.
2020/0020454 A1 1/2020 McGarvey et al.
2020/0043077 A1 2/2020 Turner et al.
2020/0051573 A1 2/2020 Jones et al.
2020/0058381 A1 2/2020 Patel
2020/0074382 A1 3/2020 Olsen et al.
2020/0097131 A1 3/2020 Bowden et al.
2020/0121544 A1 4/2020 George et al.
2020/0126670 A1 4/2020 Bender et al.
2020/0143655 A1 5/2020 Gray et al.
2020/0151277 A1 5/2020 Fisher
2020/0160428 A1 5/2020 Calvo et al.
2020/0272998 A1 8/2020 Jameson et al.
2020/0286310 A1 9/2020 Carver et al.
2020/0302549 A1 9/2020 Jordan, II et al.
2020/0311682 A1 10/2020 Olshansky
2020/0311709 A1 10/2020 White, III et al.
2020/0312113 A1 10/2020 Victor
2020/0327791 A1 10/2020 Moon et al.
2020/0335183 A1 10/2020 Tommasi et al.
2020/0341593 A1 10/2020 Han et al.
2020/0349632 A1 11/2020 Xu et al.
2020/0365264 A1 11/2020 Girardeau et al.
2021/0019694 A1 1/2021 Dhesi et al.
2021/0035432 A1 2/2021 Moon et al.
2021/0042843 A1 2/2021 Bryant et al.
2021/0043058 A1 2/2021 Williams et al.
2021/0090188 A1 3/2021 Lai et al.
2021/0090300 A1 3/2021 Leppänen et al.
2021/0158671 A1 5/2021 Jordan, II et al.
2021/0174916 A1 6/2021 Ginsburg et al.
2021/0312528 A1 10/2021 Benkreira et al.
2021/0335115 A1 10/2021 Williams et al.
2021/0358618 A1 11/2021 Crocker
2022/0012999 A1 1/2022 Marotta et al.
2022/0013222 A1 1/2022 Marotta et al.
2022/0019518 A1 1/2022 Marcin et al.
2022/0031239 A1 2/2022 Curtis
2022/0092669 A1 3/2022 Abrahamian et al.
2022/0114210 A1 4/2022 Kessler
2022/0114640 A1 4/2022 Pawar
2022/0159344 A1 5/2022 Gutierrez
2022/0310079 A1 9/2022 Kalns et al.
2022/0353565 A1 11/2022 Chow et al.
2022/0355802 A1 11/2022 Chaves et al.
2022/0405856 A1 12/2022 Hedges et al.
2023/0023808 A1 1/2023 Wall et al.
2023/0153916 A1 5/2023 Little et al.
2023/0342732 A1 10/2023 Aspro et al.
2023/0342857 A1 10/2023 Gibson et al.
2023/0342858 A1 10/2023 Gibson et al.
2023/0342859 A1 10/2023 Gibson et al.
2023/0342862 A1 10/2023 Gibson et al.
2023/0342867 A1 10/2023 Gibson et al.
2023/0342868 A1 10/2023 Gibson et al.
2023/0342869 A1 10/2023 Gibson et al.
2023/0377070 A1 11/2023 Gibson et al.

(56) References Cited

U.S. PATENT DOCUMENTS

| | | | |
|---|---|---|---|
| 2024/0037680 | A1 | 2/2024 | Gibson et al. |
| 2024/0046366 | A1 | 2/2024 | Yager et al. |
| 2024/0087290 | A1 | 3/2024 | Hedges et al. |

FOREIGN PATENT DOCUMENTS

| | | | |
|---|---|---|---|
| JP | 2013179381 | A | 9/2013 |
| JP | 2014056423 | A | 3/2014 |
| JP | 2014142889 | A | 8/2014 |
| JP | 2017116994 | A | 6/2017 |
| WO | 2009061936 | A1 | 5/2009 |
| WO | 2011133628 | A1 | 10/2011 |
| WO | 2014106294 | A1 | 7/2014 |
| WO | 2019086849 | A1 | 5/2019 |
| WO | 2019246239 | A1 | 12/2019 |
| WO | 2020010217 | A1 | 1/2020 |

OTHER PUBLICATIONS

“Elderly Alexa’ helps families care for their loved ones via voice”, Perez, Sarah, techcrunch.com, May 14, 2017 (Year: 2017).

“Elderly Alexa’ helps families care for their remote loved ones via voice”, reposted by Northeastern Global News, May 14, 2017, 3 p.

“Elderly-Alexa”, TechCrunch video retrieved from https://techcrunch.com/unified-video/elderly-alexa/, May 14, 2017, 12 p.

“Eldery-Alexa” TechCrunch article retrieved from https://techcrunch.com/unified-video/elderly-alexa/, May 14, 2017, 7 p.

“How to use Alexa Care Hub to help monitor and contact older relatives or friends”, Dave Johnson, Business Insider, Jan. 14, 2021, https://www.businessinsider.com/how-to-use-alexa-care-hub.

Akl et al. Unobtrusive Detection of Mild Cognitive Impairment in Older Adults Through Home Monitoring. IEEE J Biomed Health Inform. Mar. 2017;21(2):339-348. doi: 10.1109/JBHI.2015.2512273. Epub Dec. 24, 2015. PMID: 26841424; PMCID: PMC4919247. 22 p.

Amazon’s Care Hub will see success due to swelling interest in aging at home“ and boosted smart speaker adoption”, Zoe LaRock, Nov. 13, 2020, https://www.businessinsider.com/amazon-care-hub-will-succeed-amid-growing-smart-speaker-adoption-2020-11.

Apple. (2018, Dec. 17). SilverSneakers GO. Retrieved from Itunes App Store: https://itunes.apple.com/US/app/ silversneakers-go/id1410437380?mt=8.

Apple. (Dec. 6, 2018). App Store. Retrieved from Apple Web Site: https://www.apple.com/ios/app-store/.

Apple. (Dec. 6, 2018). DVD Netflix. Retrieved from iTunes App Store Preview: https://itunes.apple.com/us/app/dvd-netflix/id1169772776?mt=8.

Austin et al., “A Smart-Home System to Unobtrusively and Continuously Assess Loneliness in Older Adults”, IEEE Journal of Translational Engineering in Health and Medicine, 2016, doi: 10.1109/JTEHM.2016.2579638. PMID: 27574577; PMCID: PMC4993148, 11 p.

Austin et al., “Variability in medication taking is associated with cognitive performance in nondemented older adults”, Alzheimers and Dementia: Diagnosis, Assessment and Disease Monitoring, 2017, doi: 10.1016/j.dadm.2017.02.003. PMID: 28349120; PMCID: PMC5358531, 4 p.

Austin, Daniel et al., “Unobtrusive monitoring of the longitudinal evolution of in-home gait velocity data with applications to elder care”, Conf Proc IEEE Eng Med Biol Soc., 2011; 2011:6495-8. doi: 10.1109/IEMBS.2011.6091603. PMID: 22255826; PMCID: PMC3402166. 9 p.

Banerjee et al., “Exploratory analysis of older adults’ sedentary behavior in the primary living area using kinect depth data”, Journal of Ambient Intelligence and Smart Environments, 9, 163-179, 10.3233/AIS-170428, 2017, 18 p.

Bouwer, Julia. Evaluating eWALL: Assessing and enhancing older adults’ acceptance of a protoype smart home technology, Jan. 2015, retrieved from <https://essay.utwente.nl/69042/1/Bouwer_BA_BMS.pdf>, 59 p.

C. R. Costa, L. E. Anido-RifOn and M. J. Fernandez-Iglesias, “An Open Architecture to Support Social and Health Services in a Smart TV Environment,” in IEEE Journal of Biomedical and Health Informatics, vol. 21, No. 2, pp. 549-560, Mar. 2017, doi: 10.1109/JBHI.2016.2525725 (Year: 2017).

Canary Care How It Helps page retrieved from https://web.archive.org/web/20190322142707/canarycare.co.uk/how-it-helps/, Mar. 22, 2019, 10 p.

Canary Care How it works page retrieved from https://web.archive.org/web/20190322142414/https://www.canarycare.co.uk/how-it-works/, Mar. 22, 2019, 9 p.

Chung et al., “Feasibility testing of a home-based sensor system to monitor mobility and daily activities in Korean American older adults”, Int J Older People Nurs. Mar. 2017; 12(1). doi: 10.1111/opn. 12127. PMID: 27431567. 31 p.

“Amazon Announces HIPAA-Compliant Alexa Skills, Opening Possibilities for Senior Living,” available at https://seniorhousingnews.com/2019/04/04/amazon-announces-hipaa-compliant-alexa-skills-opening-possibilities-for-senior-living/; Apr. 4, 2019; 4 pp.

Ask My Buddy, available at https://www.amazon.com/Beach-Dev-Ask-My-Buddy/dp/B017YAF22Y; 2 pp.

OnGuardian Wins Top Prize, available at https://www.onguardian.io/test-post/; 1 p.

“OnGuardian Selected as Finalist at Aging2.0 Global Startup Search,” available at https://www.onguardian.io/new- post/; 2 pp.

“Exciting Update: Unveiling Our Latest Video Overview of OnGuardian for Communities!”; available at https://www.onguardian.io/category/news/; 1 p.

OnGuardian by OnGuardian Apps LLC; https://www.amazon.com/OnGuardian-Apps-LLC/dp/B06XGTJ549; 3 pp.

User Guide-Registration and Setup; https://www.onguardian.io/new-post-2/; 2 pp.

“Exciting Update: Unveiling Our Latest Video Overview of OnGuardian for Communities!”; available at https://www.onguardian.io/exciting-update-unveiling-our-latest-video-overview-of-onguardian-for-communities/; 6 pp.

How to Protect Personal Information Online; Jun. 29, 2020; Carnegie Mellon University Information Security Office Computing Services (Year: 2020).

Ho, Annabell Suh; Understanding the Impact of Conversational AI on Supportive Interactions: Towards the Care (Conversational AI and Response Effects) Model; Stanford University, ProQuest Dissertations & Theses, 2018. 28330492. ; (Year: 2018).

Adobe. Adobe Premiere Elements Help. Sep. 15, 2015. 273 pages. https://helpx.adobe.com/archive/en/premiere-elements/14/ premiere-elements_reference.pdf (Year: 2015).

Reddit question How to replace 5 seconds of video with a still image? (Premiere Elements 14) asked by jasonrumohrlmt. 2 pages https://www.reddit.com/r/VideoEditing/comments/jeu391/how_to_replace_5_seconds_of_video_with_a_still/ (Year: 2021).

Microsoft Community, “How to replace a video section but retain the audio in Windows Movie Maker?”, Apr. 19, 2009, <https://answers.microsoft.com/en-US/windows/forum/all/how-to-replace-a-video-section-but-retain-the/a79384d0-64cf-40b1-8f25-a1091a4267fd> (Year: 2009).

D. J. Cook et al., “MavHome: an agent-based smart home,” Proceedings of the First IEEE International Conference on Pervasive Computing and Communications, 2003 (PerCom 2003), Fort Worth, TX, pp. 521-524, doi: 10.1109/PERCOM.2003.1192783, 15 p.

Dawadi et al., “Automated Cognitive Health Assessment From Smart Home-Based Behavior Data”, IEEE J Biomed Health Inform. Jul. 2016;20(4): 1188-94. doi: 10.1109/JBHI.2015.2445754, PMID: 26292348; PMCID: PMC4814350, 38 p.

E. Leinonen, A. Firouzian, C. Partanen and P. Pulli, “Visual validation services with time coordination for senior citizens social events—OldBirds digital twin platform,” 2019 IEEE International Conference on Engineering, Technology and Innovation (ICE/ITMC), 2019, pp. 1-7, doi: 10.1109/ICE.2019.8792663.

Edison et al. (2017). Challenges and Opportunities in Automated Detection of Eating Activity. In: Rehg, J., Murphy, S., Kumar, S. (eds) Mobile Health. Springer, Cham. 24 p.

(56) References Cited

OTHER PUBLICATIONS

EWall for Active Long Living, Initial Scenarios and Use-Cases, Deliverable D2.2 version 1 retrieved from <https://cordis.europa.eu/docs/projects/cnect/8/610658/080/deliverables/001-eWALLD22v10.pdf>, Feb. 28, 2014, 74 p.
Facilitating Elders Aging in Place: The 2017 Enterprise Management Hackathon, retrieved from https://mitsloan.mit.edu/sites/default/files/inline-files/2017_EMTrack_Hackathon_article.pdf, 4 p.
Fritz et al., "Identifying Varying Health States in Smart Home Sensor Data : An Expert-Guided Approach", 2017, 6 p.
H. Wang, Q. Zhang, M. IP and J. T. Fai Lau, "Social Media-based Conversational Agents for Health Management and Interventions," in Computer, vol. 51, No. 8, pp. 26-33, Aug. 2018, doi: 10.1109/MC.2018.3191249 (Year: 2018).
Hellmers et al., "Towards a minimized unsupervised technical assessment of physical performance in domestic environments", In Proceedings of the 11th EAI International Conference on Pervasive Computing Technologies for Healthcare (PervasiveHealth 2017), Association for Computing Machinery, New York, NY, USA, 207-216. 10 p.
J. Anish Dev, "Bitcoin mining acceleration and performance quantification," 2014 IEEE 27th Canadian Conference on Electrical and Computer Engineering (CCECE), 2014, pp. 1-6 (Year: 2014).
Jeff Johnson, "Designing User Interfaces for an Aging Population", Feb. 2017 | Talks at Google. Retrieved from Youtube: https://www.youtube.com/watch?v=czjksAESHAo, Abstract only.
Kaye JA et al., "Intelligent Systems For Assessing Aging Changes: home-based, unobtrusive, and continuous assessment of aging", The Journals of Gerontology, Series B: Psychological Sciences and Social Sciences, 2011 i180-90, doi: 10.1093/geronb/gbq095, PMID: 21743050; PMCID: PMC3132763, 11 p.
Kyriazakos, S., Prasad, R., Mihovska, A. et al. eWALL: An Open-Source Cloud-Based eHealth Platform for Creating Home Caring Environments for Older Adults Living with Chronic Diseases or Frailty. Wireless Pers Commun 97, 1835 1875 (2017). 65 p.
Marcelino I, Lopes D, Reis M, Silva F, Laza R, Pereira A. Using the eServices platform for detecting behavior patterns deviation in the elderly assisted living: a case study. Biomed Res Int. 2015;2015:530828. doi: 10.1155/2015/530828. Epub Mar. 22, 2015. PM ID: 25874219; PMCID: PMC4385593. (Year: 2015).
Marscarenhas, Natasha, "BostonInno Approved: The Week's Top Tech & Startup Events in Boston", Mar. 17, 2017, 5 p.
Mengxuan, Ma et al., "VicoVR-Based Wireless Daily Activity Recognition and Assessment System for Stroke Rehabilitation," 2018 IEEE International Conference on Bioinformatics and Biomedicine (BIBM), Madrid, Spain, 2018, pp. 1117-1121, doi: 10.1109/BIBM.2018.8621151, 5 p.
Mozer, Michael C . . . "The Neural Network House: An Environment that Adapts to its Inhabitants." Proceedings of the American Association for Artificial Intelligence Spring Symposium on Intelligent Environments, (1998), 5 p.
Nashville Post, "Seniors have increasingly become more tech savvy", Aug. 28, 2017, available at https://www.nashvillepost.com/business/people/seniors-have-increasingly-become-more-tech-savvy/article_2e047f87-8872-5d1e-b2cb-5be6392f9efd.html, 4 p.
Newland et al., "Continuous In-Home Symptom and Mobility Measures for Individuals With Multiple Sclerosis: A Case Presentation", Journal of Neuroscience Nurses, Aug. 2017; 49(4):241-246. doi: 10.1097/JNN.0000000000000299. PMID: 28661948. 6 p.
Nunez-Marcos et al., Vision-based fall detection with convolutional neural networks, Wireless and Communications and Mobile Computing, vol. 2017, Article ID 9474806, 16 pgs.
ORCATECH Research Studies available at https://www.ohsu.edu/oregon-center-for-aging-and-technology/orcatech-research-studies, retrieved on Jul. 2, 2023, 4 p.
P. Kuryloski, S. Pai, S. Wicker, Y. Xue, "MedSN System for In-Home Patient Monitoring: Architecture, Privacy and Security" Proceedings of the Joint Conference on High Confidence Medical Devices, Software, and Systems (HCMDSS07) and Medical Device Plug-and-Play Interoperability (MD PnP07), Jun. 25-27, 2007, Boston, MA.
Parde, Natalie; Reading with Robots: A Platform to Promote Cognitive Exercise Through Identification and Discussion of Creative Metaphor in Books; : University of North Texas. ProQuest Dissertations Publishing, 2018. 11005488. (Year: 2018).
Perez, Sarah, 'Elderly Alexa' helps families care for their remote loved ones via voice, TechCrunch, May 14, 2017, 8 p.
Petersen et al., "Time Out-of-Home and Cognitive, Physical, and Emotional Wellbeing of Older Adults: A Longitudinal Mixed Effects Model", PLoS One. Oct. 5, 2015;10(10): e0139643. doi: 10.1371/journal.pone.0139643. PMID: 26437228; PMCID: PMC4593630. 16 p.
Pirzada et al., Sensors in Smart Homes for Independent Living of the Elderly, 2018, 2018 5th International Multi-Topic ICT Conference (IMTIC) (Year: 2018).
Pradhan et al. ; "Accessibility Came by Accident'—Use of Voice-Controlled Intelligent Personal Assistants by People with Disabilities." Proceedings of the 2018 CHI Conference on human factors in computing systems; 2018.
PubNub, "4 Game Changers from the TechCrunch Disrupt Hackathon", May 5, 2017, 15 p.
Rantz et al., "Randomized Trial of Intelligent Sensor System for Early Illness Alerts in Senior Housing", J Am Med Dir Assoc. Oct. 1, 2017;18(10):860-870. doi: 10.1016/j.jamda.2017.05.012. Epub Jul. 12, 2017. PMID: 28711423; PMCID: PMC5679074. 28 p.
Riboni et al., "Fine-grained recognition of abnormal behaviors for early detection of mild cognitive impairment," 2015 IEEE International Conference on Pervasive Computing and Communications (PerCom), St. Louis, MO, USA, 2015, pp. 149-154, doi: 10.1109/PERCOM.2015.7146521. 10 p.
Robben et al. (2016). Delta Features From Ambient Sensor Data are Good Predictors of Change in Functional Health. IEEE Journal of Biomedical and Health Informatics. 21. 1-1. 10.1109/JBHI.2016.2593980. 8 p.
Robben et al. (2012). How Is Grandma Doing? Predicting Functional Health Status from Binary Ambient Sensor Data. AAAI Fall Symposium: Artificial Intelligence for Gerontechnology. 6 p.
Robben et al. (2014). Expert knowledge for modeling the relation between functional health and data from ambient assisted living sensor systems. Poster session presented at 10th Congress of the European Union of Geriatric Medicine Society (EUGMS) 2014, Rotterdam. https://www.thieme-connect.com/products/ejournals/abstract/10.3414/ME15-01-0072, 1 p.
S. A. Becker and F. Webbe, "Use of Handheld Technology by Older Adult Caregivers as Part of a Virtual Support Network," 2006 Pervasive Health Conference and Workshops, 2006, pp. 1-10, doi: 10.1109/PCTHEALTH.2006.361697.
S. Jiang, Y. Cao, S. Iyengar, P. Kuryloski, R. Jafari, Y. Xue, R. Bajcsy, S. Wicker. "CareNet: An Integrated Wireless Sensor Networking Environment for Remote Healthcare," Proceedings of the 3rd International Conference on Body Area Networks (BODYNETS 2008), Mar. 13-15, 2008.
Seelye et al., "Passive Assessment of Routine Driving with Unobtrusive Sensors: A New Approach for Identifying and Monitoring Functional Level in Normal Aging and Mild Cognitive Impairment", Journal of Alzheimer's Disease, 59, 10.3233/JAD-170116., 2017, 19 p.
Sprint et al. (2016). Using Smart Homes to Detect and Analyze Health Events. Computer. 49. 29-37. 10.1109/MC.2016.338. 12 p.
Sprint et al. Analyzing Sensor-Based Time Series Data to Track Changes in Physical Activity during Inpatient Rehabilitation. Sensors (Basel). Sep. 27, 2017;17(10):2219. doi: 10.3390/s17102219. PMID: 28953257; PMCID: PMC5677114. 20 p.
Su et al., "Radar placement for fall detection: Signature and performance", Journal of Ambient Intelligentce and Smart Environments, 2018, 10.3233/AIS-170469, 14 p.
Tesla. (Dec. 6, 2018). Discover Software Version 9.0. Retrieved from Tesla Corporation Website: https://www.tesla.com/support/software-v9.
The Accuracy Of Self-Reported Data Of An Aging Population Using A Telehealth System In A Retirement Community Setting

(56) References Cited

OTHER PUBLICATIONS

Based On The User's Age, Gender, Employment Status And Computer Experience, Gurley, Kelley Anne. University of Maryland, Baltimore.
Yildirim et al., Fall detection using smartphone-based application, International Journal of Applied Mathmatics Electronics and Computers 4, No. 4, 2016.
Yu et al. A posture recognition-based fall detection system for monitoring an elderly person in a smart home environment, IEEE transactions on Information Technology in Biomedicine 16, No. 6: 1274-1286.
Mengxuan et al., "Assistive Adjustable Smart Shower System," 2017 IEEE/ACM International Conference on Connected Health: Applications, Systems and Engineering Technologies (CHASE), Philadelphia, PA, USA, 2017, pp. 253-254, doi: 10.1109/CHASE.2017.89, 2 p.
Riboni et al., "Extended Report: Fine-grained recognition of abnormal behaviors for early detection of mild cognitive impairment," 2015 IEEE International Conference on Pervasive Computing and Communications (PerCom), St. Louis, MO, USA, 2015, pp. 149-154, doi: 10.1109/PERCOM.2015.7146521. 10 p.
Dawadi et al., "Automated Clinical Health Assessment From Smart Home-Based Behavior Data", IEEE J Biomed Health Inform. Jul. 2016;20(4): 1188-94. doi: 10.1109/JBHI.2015.2445754, PMID: 26292348; PMCID: PMC4814350, 38 p.
Alpaydin, Ethem "Introduction to Machine Learning" (3d ed. 2014) 640 p.
"Amazon Introduces the Alexa Skills Kit—A Free SDK for Developers," available at https://press.aboutamazon.com/2015/6/amazon-introduces-the-alexa-skills-kit-a-free-sdk-for-developers; Jun. 25, 2015; 7 pp.
"Announcing New Alexa Skills Kit (ASK) Features: Account Linking and Service Simulator," available at https://developer.amazon.com/en-US/blogs/alexa/post/Tx7MF6PV44SOXU/announcing-new-alexa-skills-kit-ask-features-account-linking-and-service-simulato.html; Sep. 4, 2015; 3 pp.
"2015 Year in Review: More than 130 Skills On Alexa [Infographic]," available at https://developer.amazon.com/en-US/blogs/alexa/post/Tx2V9VQZDG9IXX/2015-year-in-review-more-than-130-skills-on-alexa-infographi.html; Jan. 7, 2016; 2 pp.
Easton, Katherine et al.; A Virtual Agent to Support Individuals Living With Physical and Mental Comorbidities: Co-Design and Acceptability Testing; J Med Internet Res. May 30, 2019;21(5): e12996 (Year: 2019).
Pradhan et al. ("Accessibility Came by Accident' Use of Voice-Controlled Intelligent Personal Assistants by People with Disabilities." Proceedings of the 2018 CHI Conference on human factors in computing systems. 2018) (Year: 2018).

* cited by examiner

FIG. 11J
1170
Check-In
CHECK-IN SHARED
Okay, your message has been shared.
Try, "Go-to my dashboard"

SENIOR LIVING ENGAGEMENT AND CARE SUPPORT PLATFORMS

CROSS-REFERENCE TO RELATED APPLICATIONS

This application is a continuation of U.S. patent application Ser. No. 18/417,752, filed Jan. 19, 2024, entitled "SENIOR LIVING ENGAGEMENT AND CARE SUPPORT PLATFORMS," which is a continuation of U.S. patent application Ser. No. 17/461,627, filed Aug. 30, 2021, entitled "SENIOR LIVING ENGAGEMENT AND CARE SUPPORT PLATFORMS," which issued as U.S. Pat. No. 11,901,071 on Feb. 13, 2024, which is a continuation of U.S. patent application Ser. No. 17/324,993, filed May 19, 2021, entitled "SENIOR LIVING ENGAGEMENT AND CARE SUPPORT PLATFORMS," which issued as U.S. Pat. No. 11,107,581 on Aug. 31, 2021, which is a continuation of U.S. patent application Ser. No. 17/038,738, filed Sep. 30, 2020, entitled "SENIOR LIVING ENGAGEMENT AND CARE SUPPORT PLATFORMS," which issued as U.S. Pat. No. 11,056,235 on Jul. 6, 2021, which is a continuation of U.S. patent application Ser. No. 16/996,592, filed Aug. 18, 2020, entitled "SENIOR LIVING ENGAGEMENT AND CARE SUPPORT PLATFORMS," which claims the benefit of priority to U.S. Provisional Patent Application Ser. No. 63/041,409, filed Jun. 19, 2020, entitled "SENIOR LIVING ENGAGEMENT AND CARE SUPPORT PLATFORMS," U.S. Provisional Patent Application Ser. No. 62/935,854, filed Nov. 15, 2019, entitled "SENIOR LIVING ENGAGEMENT AND CARE SUPPORT PLATFORMS," U.S. Provisional Patent Application Ser. No. 62/935,860, filed Nov. 15, 2019, entitled "SENIOR LIVING ENGAGEMENT AND CARE SUPPORT PLATFORMS," U.S. Provisional Patent Application Ser. No. 62/888,746, filed Aug. 19, 2019, entitled "SENIOR LIVING ENGAGEMENT AND CARE SUPPORT PLATFORMS," and U.S. Provisional Patent Application Ser. No. 62/892,207, filed Aug. 27, 2019, entitled "SENIOR LIVING ENGAGEMENT AND CARE SUPPORT PLATFORMS," the entire contents and disclosures of which are hereby incorporated herein by reference in their entirety.

FIELD OF THE INVENTION

The present disclosure relates to senior living computer platforms and, more particularly, to systems and methods for using a senior living computer platform to facilitate senior engagement with their daily schedule and caregivers associated with the seniors, and coordinate care between caregivers.

BACKGROUND

At least some conventional computer networks have enabled caregivers (e.g., family members, friends, and care service providers) associated with senior users to coordinate care for the senior user. However, conventional systems usually merely keep a schedule of the coordinated care, and may not provide additional functionality. Further, known systems may not facilitate senior engagement in their daily schedules, and may therefore not provide information on such engagement to caregivers. Known systems may have other drawbacks as well.

BRIEF SUMMARY

The present embodiments may relate to systems and methods for facilitating senior engagement in their daily schedules and coordinating care between caregivers of the senior. The system may include an engagement and care support computing device, one or more client devices, one or more third party servers, and/or one or more databases.

In one aspect, an engagement and care support platform computer system for facilitating senior user engagement may be provided. The computer system may include at least one processor in communication with at least one memory device. The at least one processor may be programmed to: (i) register a user through an application, wherein the user inputs personal and scheduling data into the application, (ii) register a caregiver associated with the user through the application, (iii) generate a senior profile based upon the user personal and scheduling data, (iv) build a daily interactive user interface that reflects the senior profile, (v) display the daily interactive user interface at a first client device associated with the user, (vi) cause the first client device to initiate a daily interaction prompt to the user, (vii) determine whether any user interaction was received at the first client device in response to the daily interaction prompt, and (viii) transmit a daily update message to a second client device associated with the caregiver, the daily update message including an indication of whether any user interaction was received at the first client device. The care coordination support platform computer system may include additional, less, or alternate functionality, including that discussed elsewhere herein.

In another aspect, a computer-implemented method for facilitating senior user engagement may be provided. The computer-implemented method may be performed by an engagement and care support platform computer system including at least one processor in communication with at least one memory device. The computer-implemented method may include: (i) registering a user through an application, wherein the user inputs personal and scheduling data into the application, (ii) registering a caregiver associated with the user through the application, (iii) generating a senior profile based upon the user personal and scheduling data, (iv) building a daily interactive user interface that reflects the senior profile, (v) displaying the daily interactive user interface at a first client device associated with the user, (vi) causing the first client device to initiate a daily interaction prompt to the user, (vii) determining whether any user interaction was received at the first client device in response to the daily interaction prompt, and/or (viii) transmitting a daily update message to a second client device associated with the caregiver, the daily update message including an indication of whether any user interaction was received at the first client device. The method may include additional, less, or alternate actions, including those discussed elsewhere herein.

In yet another aspect, a non-transitory computer-readable media having computer-executable instructions embodied thereon may be provided. When executed by an engagement and care support platform computer system including a processor in communication with a memory device, the computer-executable instructions may cause the processor to (i) register a user through an application, wherein the user inputs personal and scheduling data into the application, (ii) register a caregiver associated with the user through the application, (iii) generate a senior profile based upon the user personal and scheduling data, (iv) build a daily interactive user interface that reflects the senior profile, (v) display the daily interactive user interface at a first client device associated with the user, (vi) cause the first client device to initiate a daily interaction prompt to the user, (vii) determine whether any user interaction was received at the first client device in response to the daily interaction prompt, and (viii) transmit a daily update message to a second client device associated with the caregiver, the daily update message including an indication of whether any user interaction was received at the first client device.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein.

Figure 1:
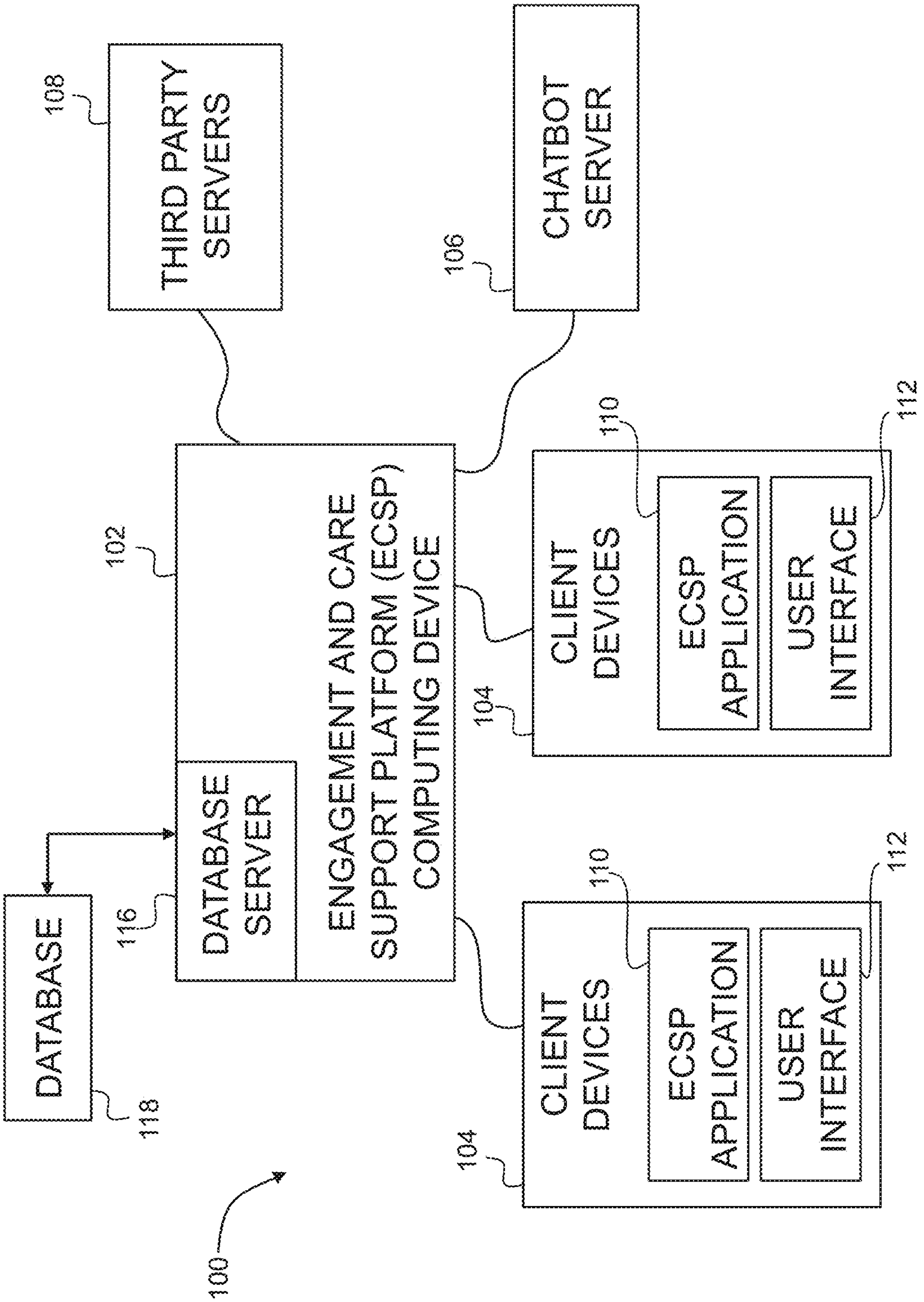
FIG. 1 illustrates an exemplary engagement and care support computer system for facilitating engagement of a user and caregivers with a care schedule of the user.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

The present embodiments may relate to, inter alia, systems and methods for facilitating engagement of a senior user (also referred to herein as a "user") in a care schedule of the user and coordinating care between caregivers associated with the user. In one exemplary embodiment, the process may be performed by an engagement and care support platform ("ECSP") computer system (also referred to herein as an "ECSP platform" and an "ECSP server"). In another embodiment, the process may be performed by a digital care circle platform, which may be configured to perform steps that are substantially similar to those described herein for the ECSP computer system.

As described below, the systems and methods described herein may leverage different types of data (e.g., user and caregiver data, user events including tasks, activities, and appointments, caregiver schedules, smart device data, and mobile device data) to facilitate independent engagement of a user (e.g., a senior user) and provide information associated with that information to a caregiver.

The caregivers associated with the user may include people who normally take care of the user (e.g., family members, friends, paid caregivers, etc.) and service providers of the user (e.g., health care professionals, such as doctors, nurses, physical therapists, occupational therapists, etc.). The caregivers often have busy schedules, and it may be difficult for the caregivers to coordinate caring for the user. Accordingly, friction between caregivers may arise from constantly trying to coordinate care and scheduling to take care of the user. Moreover, it can be unclear whether or when certain tasks have been completed, which may lead to redundancy in task completion and/or incomplete tasks.

In addition, some senior users may desire a level of independence from their caregivers, and may only want or need assistance for certain tasks. Accordingly, the user may grow frustrated with unpredictable caregiver schedules and/or unnecessary caregiver presence.

The systems and methods described herein ensure that the user is actively engaged in their care schedule and that each caregiver is informed about the status of the user and their assigned tasks of the care schedule. In addition, caregivers are able to care for the user and/or carry out tasks for the user and may reduce friction between caregivers by providing a platform that automatically assigns care duties to caregivers based upon information (e.g., scheduling and calendar information) input by the caregivers and ensures that the caregivers complete their assigned duties. Further, the systems and methods described herein may learn about the user and associated caregivers and adjust interactions with the user and associated caregivers and the coordinating of the care schedule of the user as well as engagement of the user based upon the learning. Moreover, the systems and methods herein facilitate independent senior engagement with an interface that enables caregivers to remotely view the user's interactions with the interface. Therefore, the caregivers can be assured of the senior user's state.

Exemplary User and Caregiver Data Collection

In the exemplary embodiment, an engagement and care support platform (e.g., provided by an engagement and care support platform server) may leverage different kinds of data (e.g., user and caregiver data, user events, caregiver schedules, sensor data, and mobile device data) to coordinate a care schedule of a user between one or more caregivers associated with the user and/or promote user engagement with the engagement and care support platform. In the exemplary embodiment, a primary caregiver (e.g., an admin caregiver) may register for the engagement and care support platform ("ECSP") service provided by an ECSP server through an application (e.g., a ECSP application) on a mobile device associated with the admin caregiver, or any other suitable device that may access the ECSP application and/or a website associated with the ECSP application. The user may also register for the ECSP application for himself or herself.

In registering for the ECSP service, the admin caregiver may provide the ECSP server with information associated with the user. The information associated with the user may include user data (e.g., name, birthdate, height, weight, etc.), user tasks (e.g., taking medicine, bathing, eating, paying bills, getting groceries, car maintenance, home maintenance, etc.), user activities (e.g., social activities, like bingo and golfing, physical activities, like working out and keeping active, etc.), user interests and hobbies (e.g., fishing, home improvement, gardening, etc.) user appointments (e.g., recurring appointments like yearly physicals and bimonthly haircuts, etc.), user alert preferences (e.g., when and through which method users prefer to be alerted), and any other information associated with the user that may be useful to the ECSP server. This information associated with the user may be stored in a "senior profile," which may be leveraged to generate activity schedules, provide relevant content (e.g., articles or games), and the like. In other embodiments, the user may register for the service and provide the ECSP server with information for the senior profile themselves. In some embodiments, the admin caregiver and/or the user may provide contact information for users that may not be caregivers, such as non-caregiver family members, social groups (e.g., member of a book club), etc. The contact information for these users may be identified and stored using "shortcut" names or phrases that identify the group. For example, contact information for a user's three children may be identified collectively as a "Kids" group.

Further, in registering for the ECSP service, the admin caregiver may invite other caregivers to be a part of a care team for the user and/or the user may invite other caregivers himself or herself. For example, the admin caregiver may provide the ECSP server with a list of emails and/or phone numbers of other caregivers who are associated with the user. The ECSP server may send an invitation link and/or code to the other caregivers instructing the other caregivers on how to sign up for the care team for the user associated with the admin caregiver.

Each caregiver, including the admin caregiver, may register themselves for the ECSP service. In registering for the ECSP service, the caregivers may provide the ECSP server with caregiver information (e.g., name, contact information, relationship to the user), caregiver schedule information (e.g., known work and/or activity schedules of the caregivers), caregiver alert preferences (e.g., when and through which method caregivers prefer to be alerted), and/or any other caregiver information that may be useful to the ECSP server. In some embodiments, the caregivers may link their digital calendars (e.g., provided on a mobile device associated with the caregiver) to the ECSP server such that the caregivers do not have to manually input scheduling data available to the ECSP server into the digital calendar. The user and the caregivers may update and/or edit the user and caregiver data at any time (e.g., through the ECSP application). Further, the admin caregiver and/or the user may require that each registered caregiver be approved before the caregivers are officially added to the caregivers of the user by the ECSP application. For example, the ECSP application may push a notification to the mobile device associated with the admin caregiver and/or a user device associated with the user each time a new caregiver is registered. The notification may prompt the admin caregiver and/or the user to accept or deny (e.g., through a push notification or voice command) the new caregiver. If the new caregiver is accepted by the user and/or the admin caregiver, the new caregiver may be automatically added to the caregivers associated with the user by the ECSP application.

In the exemplary embodiment, if the caregiver is a person who normally takes care of the user and needs to view and/or be notified of the schedule of the user, the caregiver may fully register for the ECSP service. If the caregiver is a person who only provides certain services to the user (e.g., a doctor, nurse, physical therapist, occupational therapist, etc.) and/or is socially involved with the user for specific activities (e.g., a garden club member, a book club member, etc.), the caregiver may have very limited access to the ECSP service, and the ECSP server may have very limited access to the caregiver data (e.g., the ECSP server may simply receive calendar updates from the caregiver if an event related to the user is scheduled).

In the exemplary embodiment, the ECSP server may also be configured to receive sensor data from sensors associated with the user and/or the caregivers. For example, sensors may include smart home device sensors (e.g., AMAZON ALEXA, GOOGLE HOME, and/or RING doorbells), wearable device sensors (e.g., APPLE WATCH and FITBIT), smart device sensors (e.g., smart pillboxes), sensors associated with a mobile device of the user and caregivers (e.g., GPS sensors), and any other sensors. In the exemplary embodiment, the ECSP server may be configured to store the received data (e.g., user data, caregiver data, sensor data, etc.) in a memory.

Exemplary Care Coordination

In the exemplary embodiment, the ECSP server may be configured to process all of the user and caregiver data (e.g., events of the user, and schedules and preferences of the caregivers) the ECSP server receives from the user and caregivers (e.g., through the ECSP application) and coordinate a care schedule of the user between the caregivers and/or promote user engagement with the ECSP application. The ECSP server may automatically assign each task, activity, and/or appointment of the user to the caregivers based upon the received caregiver data, and the received caregiver data may include caregiver preferences and schedules. The ECSP server may also promote user engagement with the ECSP server by "learning" about the user from the received user data and suggest different types of media (e.g., articles, videos, movies, TV shows, etc.) that may interest the user. The ECSP server may further suggest different activities based on the "learning" about the user. For example, the ECSP server may suggest and/or send a link to an online invite for a new gardening club if the user typically reads about gardening.

The ECSP server may allow caregivers to easily assign tasks, activities, and events of the user amongst themselves such that each caregiver is informed about the care schedule of the user, including which caregiver is assigned to each task of the care schedule. For example, the primary caregiver of the user may assign tasks that the primary caregiver knows each caregiver can handle and/or the caregivers can assign tasks to themselves as the tasks are created (e.g., through the ECSP application). The ECSP server may also process the caregiver data associated with the caregivers and compare the caregiver data to the task, activity, and appointment schedule of the user. Based upon the compared data, the ECSP server may assign each task, activity, and appointment of the user to each of the caregivers. For example, the ECSP server may assign the events to the primary caregiver first (based upon a schedule of the primary caregiver) and then assign the rest of the events not assigned to the primary caregiver to other caregivers based upon the schedules of the other caregivers.

Further, the user and/or caregivers may assign some events to the user to carry out when the user does not need assistance with the events (e.g., taking medication, doing nightly security checks, and/or doing daily exercises). Once the events have been assigned to the user and/or the caregivers, the ECSP server may create a care schedule of the user. The care schedule may include all of the user's events, and the user and/or caregiver assigned to the events. The care schedule may be stored in, for example, a care database, in a memory device associated with the ECSP server.

The ECSP server may determine if events of the care schedule of the user are taken care of by the assigned caregiver through, for example, sensor data received by the ECSP server. For instance, if a user is scheduled to take medicine at a certain time two times a day, the ECSP server may receive data from a sensor (e.g., a smart pillbox) associated with the user to determine if the pill box was opened at the certain scheduled times. Further, for example, if a caregiver is scheduled to take the user to a doctor's appointment at a certain time, the ECSP server may receive location data of the user and the caregiver (e.g., from mobile devices of the user and/or caregiver) to determine if the caregiver took the user to the doctor's appointment. Additionally, if the user is scheduled to receive a grocery delivery at a certain time, the ECSP server may receive data (e.g., from a smart home device like a smart doorbell) to determine if the groceries were delivered for the user (e.g., through determining if the doorbell was rung and/or a delivery person showed up around the scheduled time).

If the ECSP server determines that a task, activity, and/or appointment has not been carried out, the ECSP server may alert (e.g., through the ECSP application) the user and/or caregivers based upon the user and caregiver data (e.g., alert preferences). Further, the ECSP server may notify the caregivers, based on the alert preferences of the caregivers, when a scheduled event has been carried out by the caregiver and/or others (e.g., service providers). In other embodiments, the user and caregivers may manually enter that the events of the user have been taken care of by the caregiver.

Exemplary Care Coordination Support Application

In the exemplary embodiment, an ECSP application is associated with the ECSP server. The ECSP application may be configured to receive user and caregiver data, display the care schedule of the user to the caregivers, and/or alert and/or notify the user and caregivers of assigned events. The ECSP application may be run on a device associated with the user and/or caregiver (e.g., a mobile device and/or laptop of the user or caregiver). The ECSP application may be configured to display the care schedule of the user based upon the preference of the user and caregivers. For example, the ECSP application may display a list of daily, weekly, and/or monthly tasks assigned to the user and/or caregivers, a calendar that marks when the user and/or caregiver has assigned events, and any other display method that allows the user and caregivers to easily see and interact with the care schedule of the user.

In the exemplary embodiment, the ECSP server may include a chatbot that is embedded in the ECSP application and has access to the information stored by the ECSP server (e.g., scheduled/assigned events, user data, caregiver data, etc.). The chatbot may be any suitable chatbot and/or robo-assist device that functions as described herein. The chatbot may assist the user in interacting with the ECSP application (e.g., the chatbot may recognize voice commands and/or typed commands from the user), the user and caregivers in adding, editing, and/or deleting user and caregiver data, coordinating care of the user between the caregivers, receiving information about the assigned care schedule, and/or receiving information about how the user and caregivers are carrying out the care schedule. For example, instead of a user having to physically check-in with the ECSP application (e.g., through a user interface of the device associated with the user) and/or the user and/or caregiver having to manually input each event of the user, each notification request of the user and caregivers, and/or each schedule item of the caregivers, the user and caregivers may give instructions to the chatbot (e.g., through typing and/or speaking commands and/or questions using plain or colloquial language, rather than structured commands, into the chatbot through the ECSP application). For example, the chatbot may interpret the user and/or caregivers saying, "Go home," "Go to my dashboard," "Go to my home screen," or "Return home" all as commands to navigate to a dashboard of the ECSP application. Additionally, "Show me my care circle," "View my care circle," "Who's in my care circle," and "Show people in my care circle" may be interpreted by the chatbot as commands to view the care circle, "Help," "Help me," "Show me the customer support number," and "Contact customer support" may be interpreted by the chatbot as commands to get help from customer service associated with the ECSP application, "Approve," "I want to approve [name of caregiver]," "Allow," and "Allow [name of caregiver] to join" may be interpreted by the chatbot as commands to approve new caregivers, etc. Accordingly, the chatbot may be able to commands in the form of plain and colloquial language from the user and garegivers into actions. Also, for example, if the user just added a daily medication to their routine, the user may instruct the chatbot to add the medication to the daily list of tasks for the user to carry out. Further, a caregiver may instruct the chatbot that the user's lawn needs to be mowed every week in the summer.

The ECSP application may be configured to passively assist in coordinating care for the user between the caregivers. For example, if the caregivers mostly have the care schedule of the user figured out and scheduled, the chatbot may be configured to monitor what the users and caregivers input into the chatbot and provide assistance if necessary. For instance, if one caregiver inputs into the chatbot that the caregiver is taking the user to an appointment on Monday at 2 p.m., the chatbot may respond to the caregiver that the appointment is on their calendar. If another caregiver says that the caregiver is taking the user to breakfast on Tuesday at 10 a.m., the chatbot may respond to the caregiver that the event is not in their calendar and ask the caregiver if the caregiver would like the event added to their calendar. If the caregiver responds that the caregiver would like the event added to their calendar, the chatbot may cause the event to be added to the calendar of the caregiver.

The user and caregivers may also ask the ECSP application questions (e.g., through the chatbot), and the ECSP application may, for example, convert the natural-language question of the user and caregivers into a query, run the query against a database (e.g., an event database stored in a memory device), and transmit a response to the question to the processor including an answer to the question, in response to the query returning the at least one event. For example, the user may ask the ECSP application who is taking them to a haircut appointment or oil change appointment, and the caregiver may ask the ECSP application to identify the last time the user had a bath.

The ECSP application may also notify and/or send alerts to the user and caregivers based upon the user and caregiver alert preferences. For example, the ECSP application may notify a caregiver that a user has not yet taken their medicine, and the ECSP application t may ask the caregiver if the caregiver would like the ECSP application to send a reminder to the user to take their medicine (e.g., through an audible alert, such as via a chatbot). If the caregiver says yes, the ECSP application may automatically cause the reminder to be sent to the user.

In the exemplary embodiment, the ECSP application may further be configured to learn from the user and caregiver requests, responses, and/or questions. For example, if the ECSP application often notifies a caregiver that the user forgets to take a nightly dose of medication, and the caregiver typically tells the ECSP application to remind the user to take their medication in response to the notification from the ECSP application, the ECSP application may automatically cause the ECSP computing device to start reminding the user to take their nightly medicine dosage without input from the caregiver.

Further, the ECSP application may be configured to verbally explain scheduled events, scheduling conflicts, and/or missed scheduled events that may arise to the user and/or caregivers. For example, if the ECSP application determines that a scheduling conflict has arisen (e.g., the caregiver and/or the user are double-booked), the ECSP application may verbally engage with the user and/or caregiver to explain the scheduling conflict. In verbally engaging with the user and/or caregiver, the ECSP application may be configured to converse with the user and/or caregiver to resolve the scheduling conflict. Further, if the ECSP application determines that a scheduled event was missed, the ECSP application may verbally alert the user and/or caregiver of the missed event. In verbally alerting the user and/or caregiver, the ECSP application may also be configured to converse with the user and/or caregiver to resolve and/or reschedule the missed event.

In one exemplary embodiment, the ECSP server may be configured to use the ECSP application to facilitate engagement from the user. In particular, the ECSP server may leverage the ECSP application to encourage interaction and "check-ins" by the user. For example, the ECSP application may provide a daily interactive user interface to the user, may prompt the user to check-in proactively (e.g., through providing a prompt that the user answers), and/or may determine that the user has not checked-in and respond in a reactive manner (e.g., by notifying one or more caregivers that the user has not checked-in in a certain amount of days). As described herein, the daily interactive user interface may include any scheduled activities the user has in their calendar. In addition, the daily interactive user interface may display pictures or content provided by one or more caregivers. For example, a caregiver may provide a picture or article for display within the daily interactive user interface. The ECSP application may further provide an interaction prompt to the user that encourages the user to interact therewith. The interaction prompt may be visual, such as encouraging the user to "tap" a picture or to access a content item (e.g., read an article). The interaction prompt may additionally or alternatively be an audio prompt. For example, the audio prompt may be a question posed to the user (e.g., "How are you feeling today?") or may be related to a past or future scheduled activity (e.g., "Did you enjoy your Garden Club meeting yesterday?", "Are you looking forward to seeing the kids for dinner?"). The interaction prompt may additionally or alternatively encourage the user to perform an activity (e.g., "Why don't you take a five-minute walk around?") The ECSP server may leverage sensor data (e.g., from a wearable device or camera) to determine whether the user completes the suggested activity.

The ECSP server may then transmit messages to a caregiver that provide information about whether and how the user is responding to the interaction prompts. For example, the ECSP server determines whether the user responded to the interaction prompt and includes an indication of any response in daily messages to the caregiver. In this way, the caregiver may be assured that the user is in a positive physical and/or mental state. If the user does not respond to the interaction prompts for a threshold number of days (e.g., two days), the ECSP server may transmit an alert to the caregiver. The alert includes an indication that the user has not responded to interaction prompts for the threshold number of days, which may indicate that the user is hurt, confused, or otherwise in need of a more personal check-in.

The ECSP server may further be configured to generate caregiver analytics, and the ECSP application may be configured to display the generated analytics to the user and caregivers. The ECSP server may generate activity hour, effort hour, and task distribution analytics for each caregiver and compare the analytics to the other caregivers. For example, the ECSP server may generate a chart of the time each caregiver spends caring for the user and/or the time each caregiver spends putting in effort to the care of the user for a predetermined period of time. The ECSP server may further generate a chart of a percentage of tasks for the user that each caregiver handles over the predetermined period of time.

Exemplary Care Coordination Support System

FIG. 1 depicts a view of an exemplary engagement and care support platform ("ECSP") system 100 that may be used in facilitation engagement of a user and coordinating care of the user between caregivers associated with the user. ECSP system 100 may include a care coordination support platform ("ECSP") computing device 102. In the exemplary embodiment, ECSP computing device 102 is in communication with client devices 104, a chatbot server 106, and third party servers 108. ECSP computing device 102 is also in communication with a database 118 and may communicate with database 118 through a database server 116.

In some embodiments, database server 116 is a component of ECSP computing device 102. In other embodiments, database server 116 is separate from ECSP computing device 102. In some embodiments, ECSP system 100 may include a plurality of ECSP computing devices 102, client devices 104, third party servers 108, and/or databases 118.

In the exemplary embodiment, ECSP computing device 102 may be configured to store user and caregiver data, generate and/or store a care schedule for the user, and facilitate user engagement with the care schedule (e.g., by prompting the user to check in daily with the caregivers, displaying the care schedule in a user-friendly way, allowing the user to interact with the care schedule, etc.). ECSP computing device 102 may receive user and caregiver data from client devices 104 and use the user and caregiver data to register users and caregivers and generate care schedules for the user and caregivers. For example, a user and a caregiver may download an ECSP application 110 to a device (e.g., client device 104) and input data into ECSP application 110 for registration with a service provided by ECSP computing device 102. The user and caregivers may also access a website of ECSP system 100 using a web browser, and input user data into the website to register with ECSP system 100.

The user data may include personal data (e.g., name, birthdate, height, weight, etc.), user tasks (e.g., taking medicine, bathing, eating, paying bills, getting groceries, car maintenance, home maintenance, etc.), user activities (e.g., social activities, like bingo and golfing, physical activities, like working out and keeping active, etc.), user appointments (e.g., recurring appointments like yearly physicals and bimonthly haircuts, etc.), and any other information associated with the user that may be useful to ECSP computing device 102.

The caregiver data may include personal information (e.g., name, contact information, relationship to the user, role in caring for the user, etc.), caregiver schedule information (e.g., known work and/or activity schedules of the caregivers), caregiver preferences (e.g., which events the caregiver prefers to assist the user with), and any other information associated with the caregivers that may be useful to ECSP computing device 102.

ECSP application 110 may also receive other data from the user and caregivers including notification preferences of the user and caregivers (e.g., preferences of when the user and caregivers would like to be notified and how the user and caregivers would like to be notified, such as receiving a text notification and/or a push button notification from ECSP application 110).

In the exemplary embodiment, users and caregivers may update the user and caregiver data at any time through ECSP application 110. For example, user data that may need to be updated may include a change in and/or newly scheduled events of the user, and a change in a daily medication schedule of the user. For example, caregiver data that may need to be updated may include a change in and/or a new availability schedule of the caregiver and a new activity scheduled by the caregiver.

ECSP application 110 may be in communication with other applications of client device 104 and may import user and caregiver data from the other applications. For example, caregivers may allow ECSP application 110 to retrieve data from a calendar application of the caregivers such that the caregivers may only need to update the schedule associated with the caregiver in one application (e.g., a calendar application).

In the exemplary embodiment, ECSP computing device 102 may be configured to process all of the user and caregiver data ECSP computing device 102 receives from the user and caregivers (e.g., through ECSP application 110) and coordinate a care schedule of the user between the caregivers and facilitate user engagement in the care schedule. In the exemplary embodiment, the caregivers may manually assign tasks to themselves and/or other caregivers through ECSP computing device 102, and ECSP computing device 102 may store the assigned tasks of the care schedule for each caregiver. In some embodiments, ECSP computing device 102 may automatically assign each task, activity, and/or appointment of the user to the caregivers based upon the received caregiver data.

In the exemplary embodiment, client devices 104 may be computers that include a web browser or a software application, which enables client devices 104 to access remote computer devices, such as ECSP computing device 102, using the Internet or other network. More specifically, client devices 104 may be communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem. Client devices 104 may be any device capable of accessing the Internet including, but not limited to, a desktop computer, a laptop computer, a personal digital assistant (PDA), a cellular phone, a smartphone, a tablet, a smart home device (e.g., AMAZON ALEXA, AMAZON ECHO, GOOGLE HOME, and/or RING doorbells), a phablet, wearable electronics (e.g., LIFE ALERT and/or FITBIT), smart watch (e.g., APPLE WATCH), or other web-based connectable equipment or mobile devices.

Further, ECSP computing device 102 may be communicatively coupled to client devices 104 and may receive information from client devices 104. Client device 104 associated with the user may be different from client device 104 associated with the caregiver. For example, client device 104 associated with the user may be a smart home device (e.g., AMAZON ALEXA) because the user may prefer interacting with client device 104 through audio commands rather than physically interacting with client device 104. Client device 104 associated with the caregiver may be a smartphone.

In the exemplary embodiment, some client devices 104 include ECSP application 110 and a user interface 112. User interface 112 may be used, for example, to receive notifications from ECSP computing device 102 and/or to input and verify information to be sent to ECSP computing device 102. ECSP application 110 may be, for example, a program or application that runs on client device 104. Further, ECSP application 110 associated with the user client device 104 may have different functionality as ECSP application 110 associated with the caregiver client devices 104, as is explained in further detail herein, especially with regard to the screenshots of the ECSP application 110.

ECSP computing device 102 may be configured to facilitate user engagement with the care schedule and the caregivers. For example, ECSP computing device 102 (e.g., through ECSP application 110) may display the daily care schedule of the user such that the user is made aware of, and can interact with, their care schedule. ECSP computing device 102 may prompt the user to check-in with the caregivers through ECSP computing device 102. For example, ECSP computing device 102 may display a "Check-In" box that the user may press so that the caregivers know that the user is doing okay and has interacted with their care schedule. For further example, ECSP computing device 102 may keep track of how often the user interacts with ECSP computing device 102 instead of, or in addition to, the user manually checking in. Accordingly, the caregivers are assured that the user is okay, and the user plays an active part in their care schedule.

In some embodiments, ECSP computing device 102 may be configured to display (e.g., through ECSP application 110) the generated care schedule to the user and/or caregivers. ECSP computing device 102 may display the generated care schedule to the user and caregivers through task lists, graphs, calendars, and any other suitable interface that allows the user and caregiver to easily take in and interact with the care schedule of the user.

ESCP computing device 102 may be in communication with chatbot server 106 and leverage the chatbot functionality thereof to implement at least some of the functionality disclosed herein (e.g., to transmit information to and/or receive information from a user and/or one or more caregivers).

Database server 116 may be communicatively coupled to database 118 that stores data. In one embodiment, database 118 may include user data, caregiver data, device data, mobile device data, assignment data, and notification data. In the exemplary embodiment, database 118 may be stored remotely from ECSP computing device 102. In some embodiments, database 118 may be decentralized. In the exemplary embodiment, a user and/or caregiver, may access database 118 via their respective client devices 104 by logging onto ECSP computing device 102, as described herein.

Third party server 108 may be any third party server that ECSP computing device 102 is in communication with that provides additional functionality of ECSP computing device 102 and/or ECSP application 110. For example, third party server 108 may be servers associated with third parties including online retailers/delivery services (e.g., AMAZON, grocery delivery services, food deliver services flower delivery servicers, etc.), ride sharing services (e.g., UBER and LYFT), and hospital/doctor's offices servers. Because ECSP computing device 102 is in communication with third party server 108, the user and/or caregivers may directly access third party servers 108 through ECSP application 110. For example, if a caregiver wants to order flowers for the user, the caregiver may be able to order the flowers from a third party service (e.g., AMAZON) directly through ECSP computing device 102. In some embodiments, third party server 108 may provide updates to the user and/or caregivers through the ECSP application 110 (e.g., notifying the user that their ride is on their way and/or updating the caregiver on the status of their delivery to the user).

Exemplary User Computer Device

Figure 2:
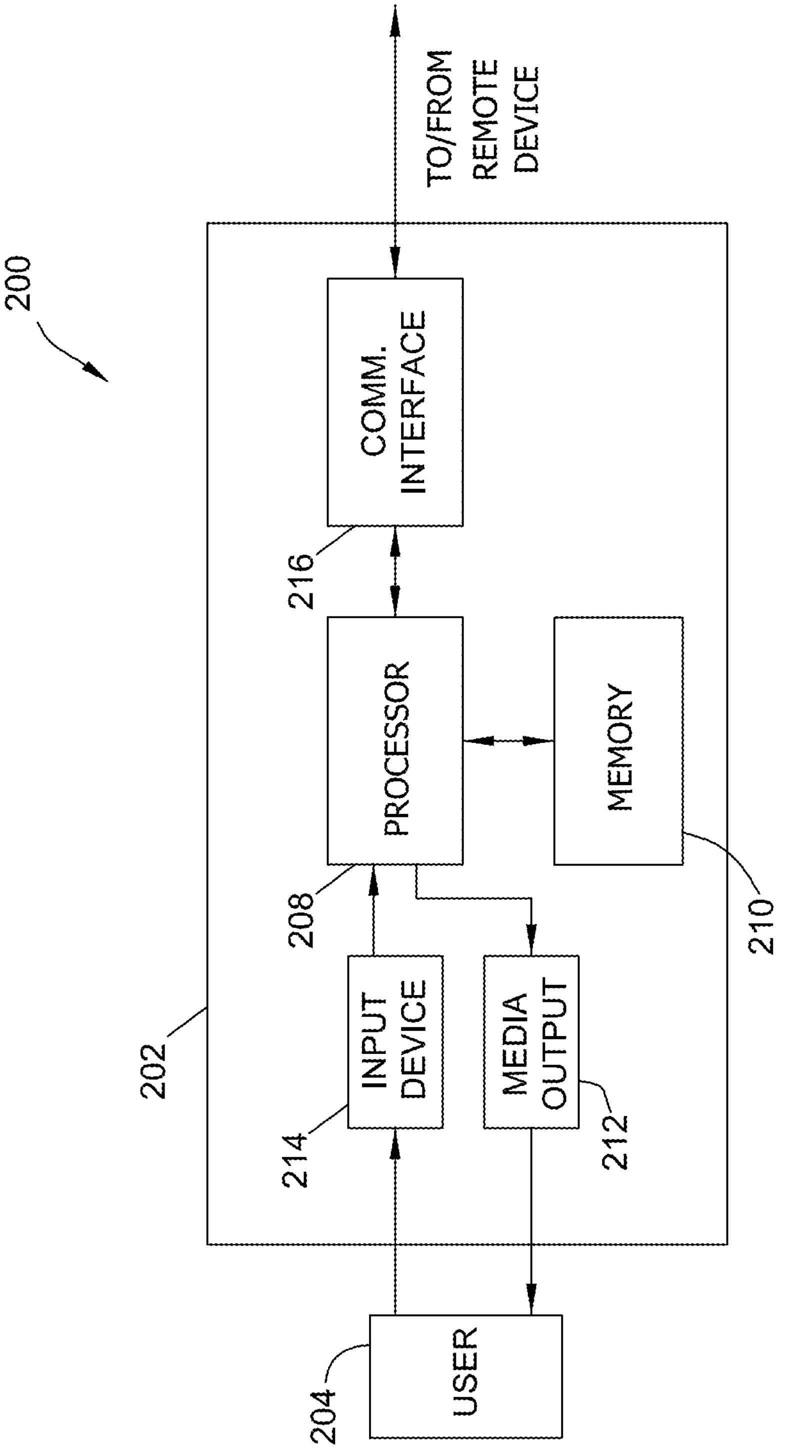
FIG. 2 illustrates an exemplary configuration of an exemplary user computing device that may be used in the engagement and care support computer system illustrated in FIG. 1.

FIG. 2 illustrates an exemplary configuration 200 of an exemplary user computing device 202. In some embodiments, user computing device 202 may be in communication with a care coordination support platform computing device (such as ECSP computing device 102, shown in FIG. 1). User computing device 202 may be representative of, but is not limited to client devices 104 and/or sensor servers 108. For example, user computing device 202 may be a mobile device, smartphone, tablet, smartwatch, wearable electronic, laptop, desktop, or another type of computing device associated with an account holder (e.g., the user and/or the associated caregivers).

User computer device 202 may be operated by a user 204 (e.g., a user of ECSP system 100, shown in FIG. 1 and substantially similar to the user and/or the caregivers described herein). User computer device 202 may receive input from user 204 via an input device 214. User computer device 202 includes a processor 208 for executing instructions. In some embodiments, executable instructions may be stored in a memory area 210. Processor 208 may include one or more processing units (e.g., in a multi-core configuration) . Memory area 210 may be any device allowing information such as executable instructions and/or user and registration data to be stored and retrieved. Memory area 210 may include one or more computer-readable media.

User computer device 202 also may include at least one media output component 212 for presenting information to user 204. Media output component 212 may be any component capable of conveying information to user 204 and may be used to at least partially implement user interface 112 (shown in FIG. 1). In some embodiments, media output component 212 may include an output adapter (not shown), such as a video adapter and/or an audio adapter. An output adapter may be operatively coupled to processor 208 and operatively coupleable to an output device, such as a display device (e.g., a cathode ray tube (CRT), liquid crystal display (LCD), light emitting diode (LED) display, or "electronic ink" display) or an audio output device (e.g., a speaker or headphones).

In some embodiments, media output component 212 may be configured to present a graphical user interface (e.g., a web browser and/or a client application) to user 204. A graphical user interface may include, for example, care calendars for the user and/or associated caregivers, lists of assigned tasks of the care schedule for the user and/or caregivers, notifications for the user and/or associated caregivers, assigned tasks of the caregivers, an activity analytics of the caregivers, and/or a messaging page for interacting with the user and/or caregivers. The graphical user interface may additionally include visual interaction prompts that are periodically (e.g., daily, twice daily, every other day, etc.) provided to the user. Visual interaction prompts may include instructions, images, content (e.g., articles or other text), and the like. Media output component 212 may additionally or alternatively provide audible interaction prompts (e.g., via an audio output device).

In some embodiments, user computer device 202 may include input device 214 for receiving input from user 204. User 204 may use input device 214 to, without limitation, interact with ECSP system 100 (e.g., using ECSP application 110), ECSP computing device 102, or any of client devices 104 and third party servers 108 (shown in FIG. 1). Input device 214 may include, for example, a keyboard, a pointing device, a mouse, a stylus, and/or a touch sensitive panel (e.g., a touch pad or a touch screen) and may be used to at least partially implement user interface 112 (shown in FIG. 1). A single component, such as a touch screen, may function as both an output device of media output component 212 and input device 214. User computer device 202 may further include at least one sensor, including, for example, a gyroscope, an accelerometer, a position detector, a biometric input device, and/or an audio input device. In some embodiments, at least some data collected by user computer device 202 may be transmitted to ECSP computing device 102. In the exemplary embodiment, data collected by user computer device 202 may be included in user and caregiver data.

User computer device 202 may also include a communication interface 216, communicatively coupled to any of ECSP computing device 102, client devices 104, and third party servers 108. Communication interface 216 may include, for example, a wired or wireless network adapter and/or a wireless data transceiver for use with a mobile telecommunications network.

Stored in memory area 210 may be, for example, computer-readable instructions for providing a user interface to user 204 via media output component 212 and, optionally, receiving and processing input from input device 214. The user interface may include, among other possibilities, a web browser and/or a client application. Web browsers enable users, such as user 204, to display and interact with media and other information typically embedded on a web page, a website, or an application hosted by ECSP computing device 102 and/or client device 104. A client application may allow user 204 to interact with, for example, any of ECSP computing device 102, client devices 104, and third party servers 108. For example, instructions may be stored by a cloud service and the output of the execution of the instructions sent to the media output component 212. User computing device 200 may include additional, less, or alternate functionality, including that discussed elsewhere herein.

Exemplary Server Device

Figure 3:
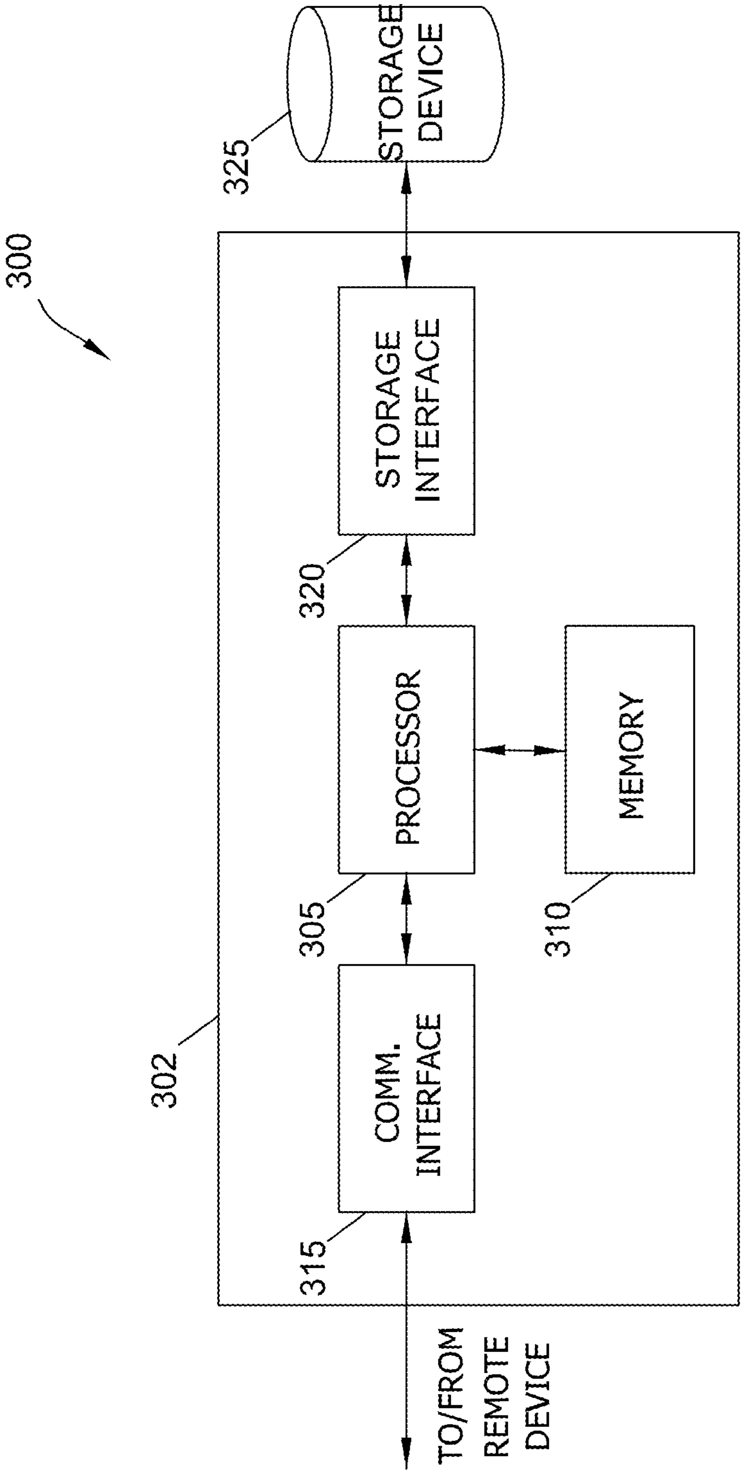
FIG. 3 illustrates an exemplary configuration of an exemplary server computing device that may be used in the engagement and care support computer system illustrated in FIG. 1.

FIG. 3 depicts an exemplary configuration 300 of an exemplary server computer device 302, in accordance with one embodiment of the present disclosure. Server computer device 302 may include, but is not limited to, ECSP computing device 102 (shown in FIG. 1). Server computer device 302 may include a processor 305 for executing instructions. Instructions may be stored in a memory area 310. Processor 305 may include one or more processing units (e.g., in a multi-core configuration).

Processor 305 may be operatively coupled to a communication interface 315 such that server computer device 302 may be capable of communicating with a remote device such as another server computer device 302 or a user computing device, such as client device 104 (shown in FIG. 1). For example, communication interface 315 may receive requests from or transmit requests to client devices 104 via the Internet.

Processor 305 may also be operatively coupled to a storage device 325. Storage device 325 may be any computer-operated hardware suitable for storing and/or retrieving data, such as, but not limited to, data associated with database 118 (shown in FIG. 1). In some embodiments, storage device 325 may be integrated in server computer device 302. For example, server computer device 302 may include one or more hard disk drives as storage device 325. In other embodiments, storage device 325 may be external to server computer device 302 and may be accessed by a plurality of server computer devices 302. For example, storage device 325 may include a storage area network (SAN), a network attached storage (NAS) system, and/or multiple storage units such as hard disks and/or solid state disks in a redundant array of inexpensive disks (RAID) configuration.

In some embodiments, processor 305 may be operatively coupled to storage device 325 via a storage interface 320. Storage interface 320 may be any component capable of providing processor 305 with access to storage device 325. Storage interface 320 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 305 with access to storage device 320.

Processor 305 executes computer-executable instructions for implementing aspects of the disclosure. In some embodiments, processor 305 may be transformed into a special purpose microprocessor by executing computer-executable instructions or by otherwise being programmed.

Exemplary Computer-Implemented Method

Figure 4:
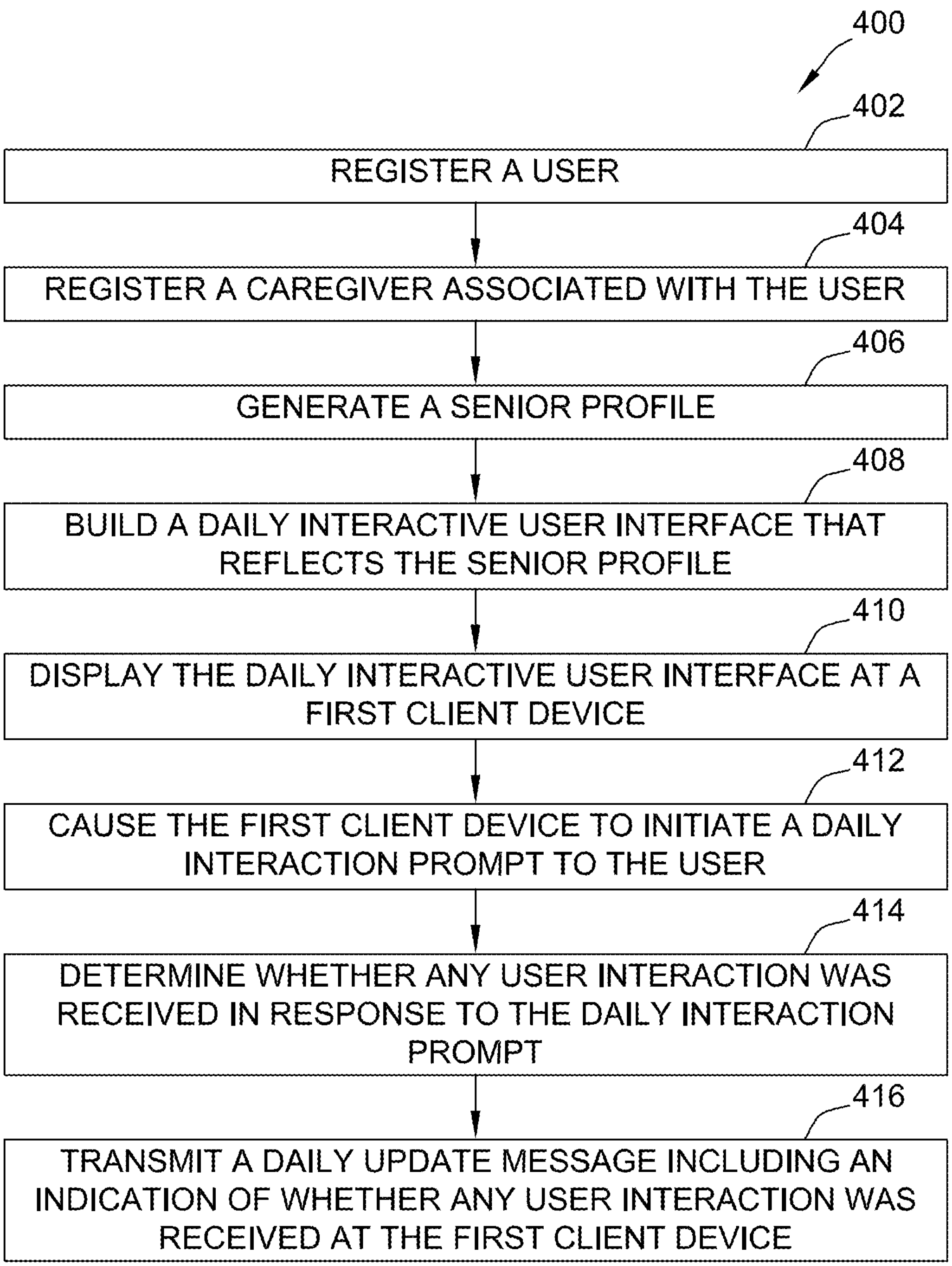
FIG. 4 illustrates a flow chart of an exemplary computer-implemented method implemented by the exemplary engagement and care support computer system shown in FIG. 1.

FIG. 4 depicts a flow chart illustrating a computer-implemented method 400 for facilitating engagement of a senior user. In the exemplary embodiment, method 400 may be implemented by a care coordination support platform computer system such as ECSP computing device 102 (shown in FIG. 1).

Method 400 may include registering 402 a user and registering 404 at least one caregiver associated with the user for a care coordination support platform service (e.g., provided by ECSP computer system shown in FIG. 1). Method 400 may also include generating 406 a senior profile based upon user personal and scheduling data provided during registering 402. Method 400 may further include building 408 a daily interactive user interface that reflects the senior profile.

Method 400 may also include displaying 410 the daily interactive user interface at a first client device associated with the user, for example, via an application associated with ECSP computing device 102, shown in FIG. 1. Method 400 may further include causing 412 the first client device to initiate a daily interaction prompt to the user, and determining 414 whether any user interaction was received at the first client device in response to the daily interaction prompt. In addition, method 400 may include transmitting 416 a daily update message to a second client device associated with the caregiver, the daily update message including an indication of whether any user interaction was received at the first client device.

Exemplary Computer Device

Figure 5:
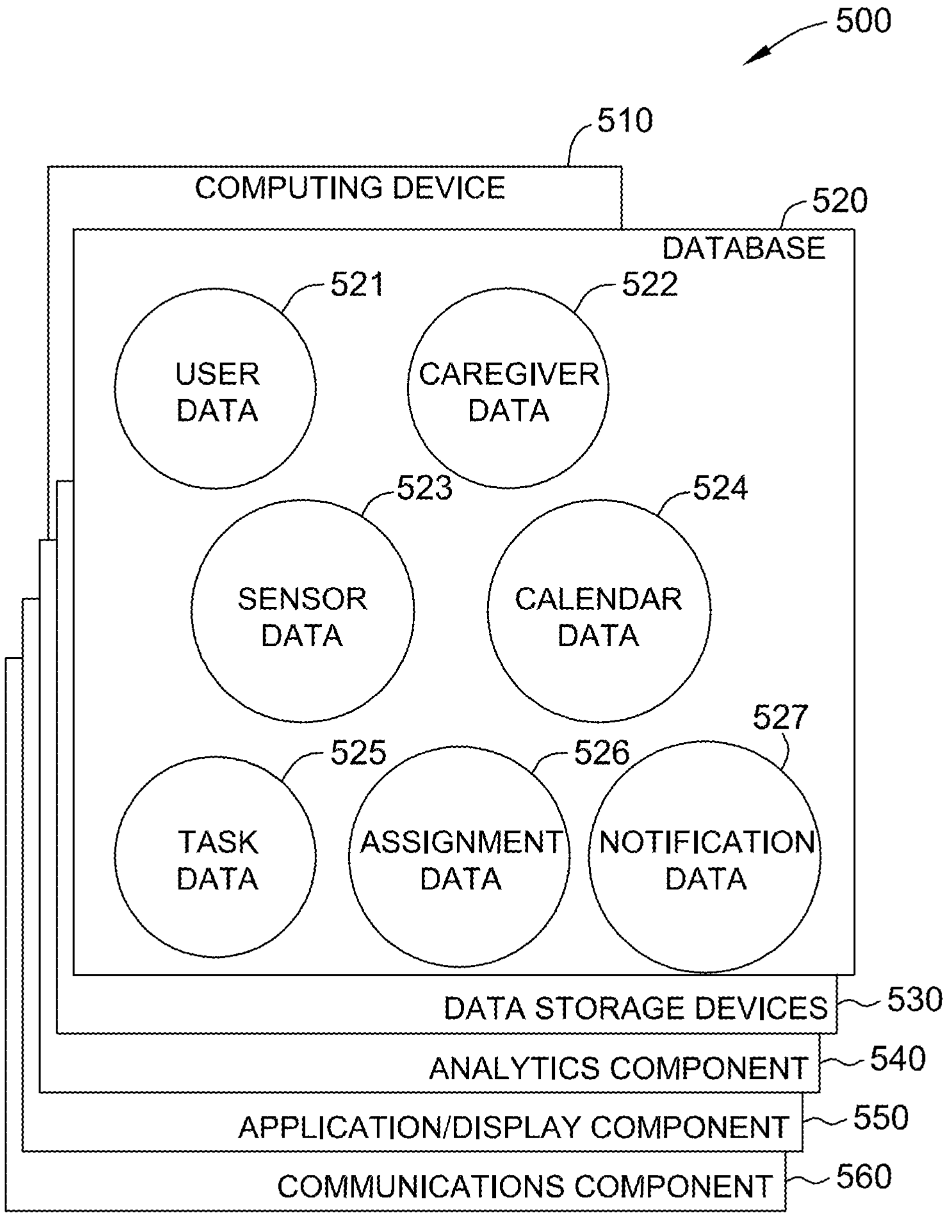
FIG. 5 illustrates a diagram of components of one or more exemplary computing devices that may be used in the engagement and care support computer system shown in FIG. 1.

FIG. 5 depicts a diagram 500 of components of one or more exemplary computing devices 510 that may be used in care coordination support platform system 100 (shown in FIG. 1). In some embodiments, computing device 510 may be similar to ECSP computing device 102 (shown in FIG. 1). Database 520 may be coupled with several separate components within computing device 510, which perform specific tasks. In this embodiment, database 520 may include user data 521, caregiver data 522, sensor data 523, calendar data 524, task data 525, assignment data 526, and notification data 527. In some embodiments, database 520 is similar to database 118 (shown in FIG. 1).

Computing device 510 may include database 520, as well as data storage devices 530. Computing device 510 may also include an analytics component 540 for analyzing received user data to generate a senior profile based upon the received data. The senior profile may be used to recommend activities, provide content of interest (e.g., articles), track schedules, and the like. Analytics component 540 may be further configured to analyze received data to determine whether a user has responded to an interaction prompt, as described herein. Computing device 510 may further include application/display component 550 for generating and displaying information (e.g., interaction prompts) to users, such as through ECSP application 110 (shown in FIG. 1), and supporting ECSP application 110. Moreover, computing device 510 may include communications component 560 for receiving and transmitting data (e.g., to and from client devices 104), such as user data 521, caregiver data 522, sensor data 523, calendar data 524, task data 525, assignment data 526, and notification data (e.g., daily update messages) 527, as well as responses to interaction prompts. Computing devices 510 may include additional, less, or alternate functionality, including that discussed elsewhere herein.

Exemplary Care Coordination Support Application

FIGS. 6-18 include screenshots of one example embodiment of an application (e.g., ECSP application 110, shown in FIG. 1) executable as part of an engagement and care support platform system (e.g., engagement and care support platform system 100, shown in FIG. 1). The application may be accessible on any suitable electronic device, such as a mobile phone, tablet, smart home device, watch, or any other computing device. The application enables a user to check in and interact with the application, determine what tasks caregivers need to complete, view a care schedule of the user, and enables one or more caregivers to add tasks for the user, view the tasks that the one or more caregivers have to complete for and/or with the user, and coordinate the care schedule between the one or more caregivers.

In some embodiments, the application may enable the user and the one or more caregivers to subscribe to alerts, notifications, and/or reminders.

The application may be configured to communicate with various other software and/or applications on the computing devices of the users and/or the one or more caregivers. For example, the application may be able to access or otherwise communicate with calendar applications and/or contact applications. The application may be configured to retrieve data from and/or report data to these other applications. In addition, the application may be configured to track, monitor, and/or record application utilization metrics for the user and/or the caregivers, such as how often the user and/or the caregivers access the application, and the various features of the application used by the user and/or the caregivers.

In one embodiment, the application, once downloaded onto the computing device of the user and/or the caregivers, may not require internet connectivity to perform some or all of the functionality of the application (e.g., setting alerts and notifying the user and/or caregivers of the alerts). In some embodiments, all or a portion of the data input by the user and/or caregivers into the application (including, for example, application utilization metrics, task logs, etc.) may be electronically transmitted to a server (e.g., ECSP server 102) for processing, and the processed data may be transmitted back for further processing and/or display by the application.

In the exemplary embodiment, the application can be configured to, inter alia, allow the user to quickly and easily check-in with the caregivers, giving the caregivers peace of mind, proactively allowing the user to check-in (e.g., by prompting the user to answer a question like "How are you feeling today?"), providing a reactive response if/when the user does not check in (e.g., by notifying one or more of the caregivers), providing an interactive display for the user and the caregivers, provide tools for the user and the caregivers to coordinate key tasks associated with the care schedule of the user, providing smart suggestions of media for the user to increase user engagement with the application, allowing caregivers to easily share photos and videos with the user, allowing the user to easily view the shared photos and videos, allowing the user to view their care schedule with audio commands and/or through interacting with the digital display of the application, and providing social features that help the user and caregivers stay and feel connected.

Figure 6:
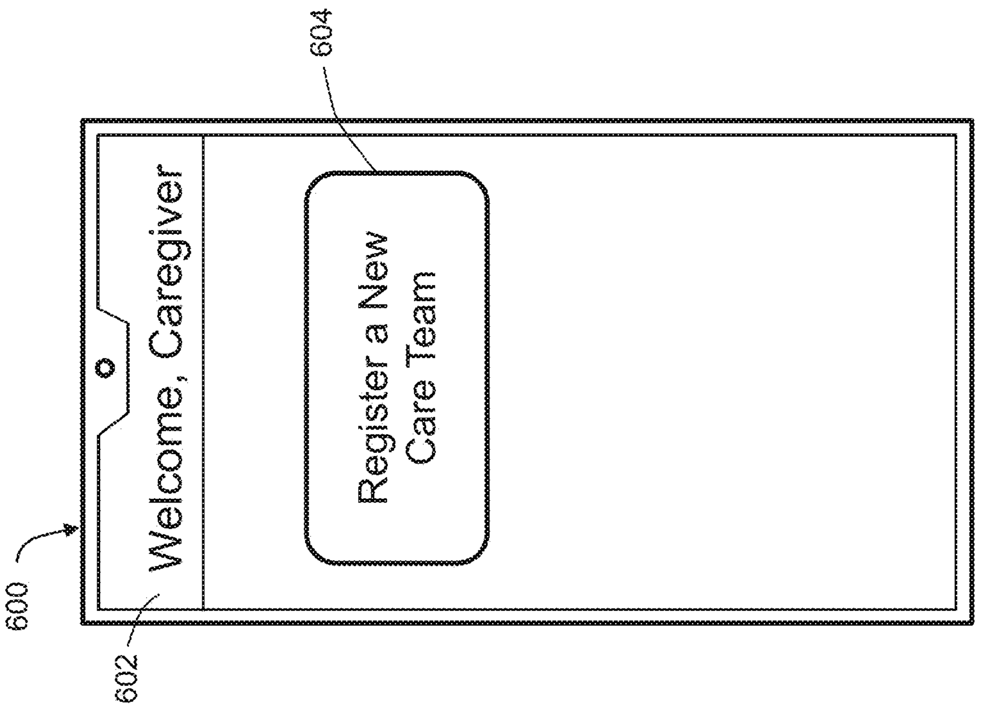
FIG. 6 is a screenshot of one example initial welcome page of an engagement and care support application illustrated in FIG. 1.

FIG. 6 illustrates an initial welcome page 600 that may include a header 602. Although not specifically shown, header 602 may include a home button, a back button, and any other buttons to help the user and/or the caregivers navigate the application. In some embodiments, initial welcome page 600 may further include a footer (not specifically shown) that may include additional buttons to help the user and/or the caregiver navigate the application. Initial welcome screen 600 may also include a "Register a New Care Team" button 604 that, when clicked, may cause the application to display a user registration screen 700.

Figure 7:
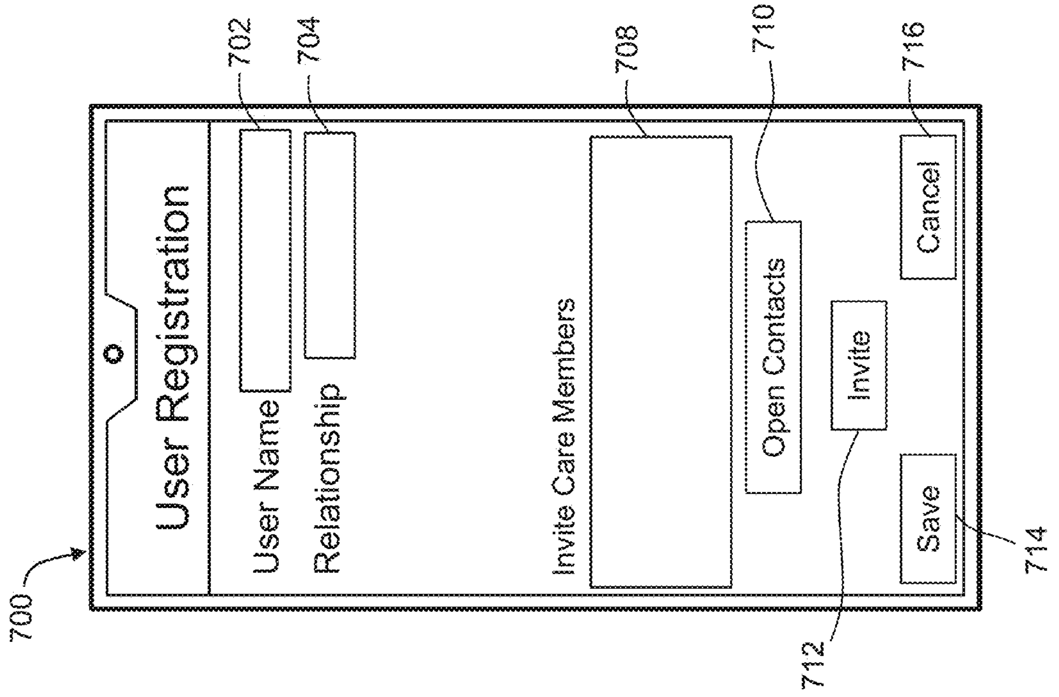
FIG. 7 is a screenshot of one example user registration page of an engagement and care support application illustrated in FIG. 1.

FIG. 7 illustrates user registration page 700 for the application. User registration page 700 may include a first field 702 for the user and/or an administrative caregiver (e.g., "admin caregiver") to enter the name of the user and a second field 704 to, if user registration page 700 is filled out by the admin caregiver, enter the relationship of the admin caregiver to the user.

Further, user registration page 700 may include a third field 708 for the user and/or admin caregiver to enter email addresses, phone numbers, and/or other contact information of other caregivers such that the application may invite the other caregivers to download the application. User registration page 700 may include a button 710 that, when clicked, may cause the application to open a contacts list of the user such that the user can choose contacts to invite instead of manually filling out third field 708.

User registration page may include an "Invite" button 712, that, when clicked, may cause the application to invite the other caregivers to download the application and/or show a caregiver registration page 800, a "Save" button 714 that, when clicked, may cause the application to save the information in fields 702, 704, and 708, and a "Cancel" button 716 that, when clicked, may cause the application to go back to initial welcome page 600. Once other caregivers download the application, the other caregivers may be directly navigated to caregiver registration page 800 and may bypass initial welcome page 600 and/or user registration page 700.

Figure 8:
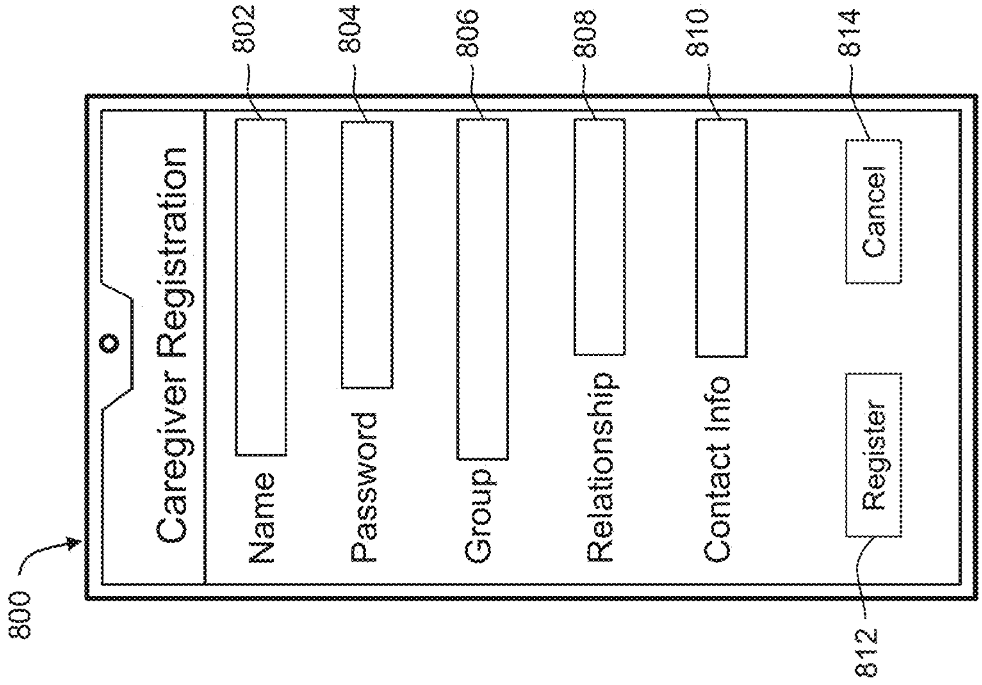
FIG. 8 is a screenshot of one example caregiver registration page of an engagement and care support application illustrated in FIG. 1.

FIG. 8 illustrates caregiver registration page 800 for the application that allows the admin caregiver and/or the other caregivers to register for the application. Caregiver registration page 800 may include a first field 802 for the caregiver to enter the name of the caregiver, a second field 804 for the caregiver to enter a password for the application, a third field 806 for the caregiver to enter a group that the caregiver belongs to (e.g., "Kids," "Grandkids," etc.), a fourth field 808 for the caregiver to enter a relationship of the caregiver to the user, and a fifth field 810 for the caregiver to enter contact information (e.g., phone number (s), email address, and/or home address).

Caregiver registration page 800 may further include a "Register" button 812 that, when clicked, may cause the application to save and store the information that caregiver entered into fields 802, 804, 806, 808, and/or 810, and display a welcome screen 900, and caregiver registration page 800 may include a "Cancel" button 814 that, when clicked, may cause the application to close and show a different screen (e.g., a home screen) of the device running the application.

Figure 9:
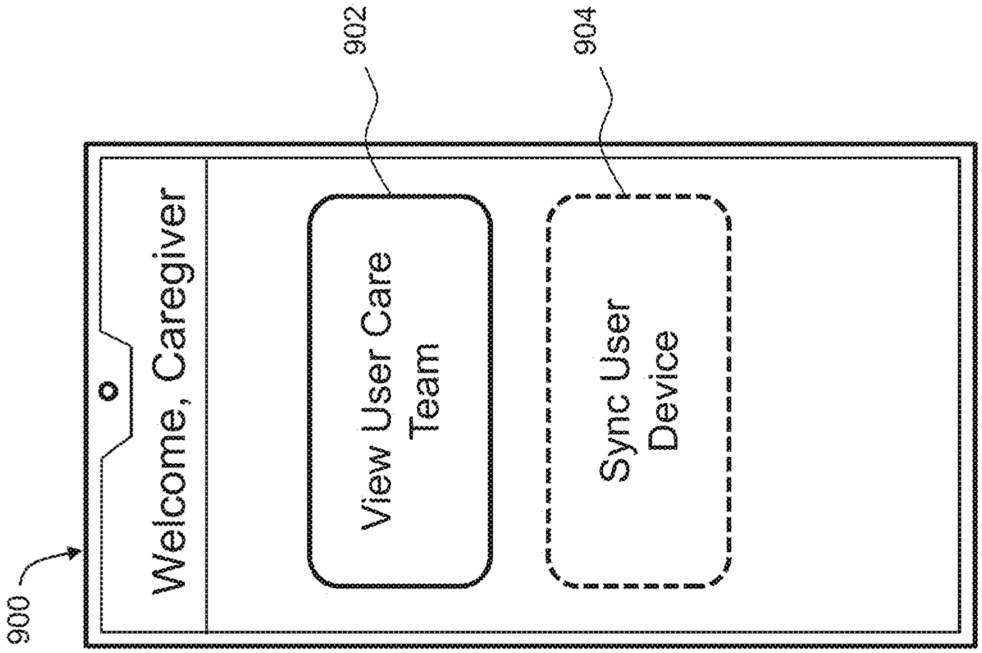
FIG. 9 is a screenshot of one example welcome page of an engagement and care support application illustrated in FIG. 1.

FIG. 9 illustrates welcome page 900 that may be the first page that the user and/or the admin caregiver are directed to until a user care team is complete (e.g., the user and all caregivers associated with the user are registered through the application). Welcome page 900 may include a "View User Care Team" button 902 that, when pressed, may cause the application to display a user care team page 1000. Welcome page 900 may further include a "Sync User Device" button 904 (e.g., if the device of the user has not been synced with the application) that, when pressed, may cause the application to display instructions for syncing the user device with the application (not specifically shown).

Figure 10:
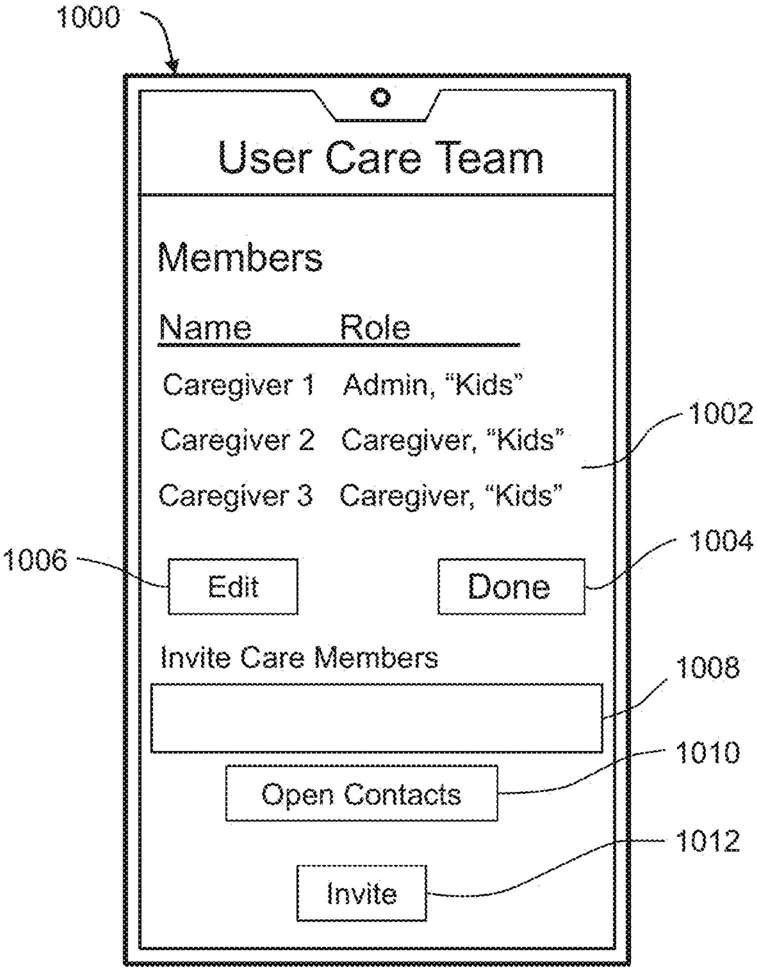
FIG. 10 is a screenshot of one example user care team page of an engagement and care support application illustrated in FIG. 1.

FIG. 10 illustrates user care team page 1000 that may allow the user and/or the admin caregiver to view and/or edit the care team associated with the user. User care team page 1000 may include a list 1002 of registered members of the care team including the names of the caregivers (e.g., entered by the caregivers in first field 802 of caregiver registration page 800, shown in FIG. 8) and groups of the caregivers (e.g., entered by the caregivers in third field 806 of caregiver registration page 800, shown in FIG. 8).

User care team page 1000 may also include an "Edit" button 1006 that, when clicked, allows the user and/or admin caregiver to edit list 1002 and a "Done" button 1004 that, when clicked, causes the application to save the care team and store the care team as fully registered. User care team page 1000 may also include a first field 1008 where the user and/or the admin caregiver may manually enter contact information of additional caregivers to add to the care team.

Additionally or alternatively, the user and/or the admin caregiver may press a "Open Contacts" button 1010 that, when pressed, causes the application to open the contacts of the user and/or admin caregiver and allow the user and/or admin caregiver to automatically choose which contacts the user and/or admin caregiver would like to invite to the care team. When the user and/or admin caregiver is done adding contact information of additional caregivers, the user and/or admin caregiver may press an "Invite" button 1012 that, when clicked, causes the application to invite the additional caregivers to register for the application.

Figure 11A:
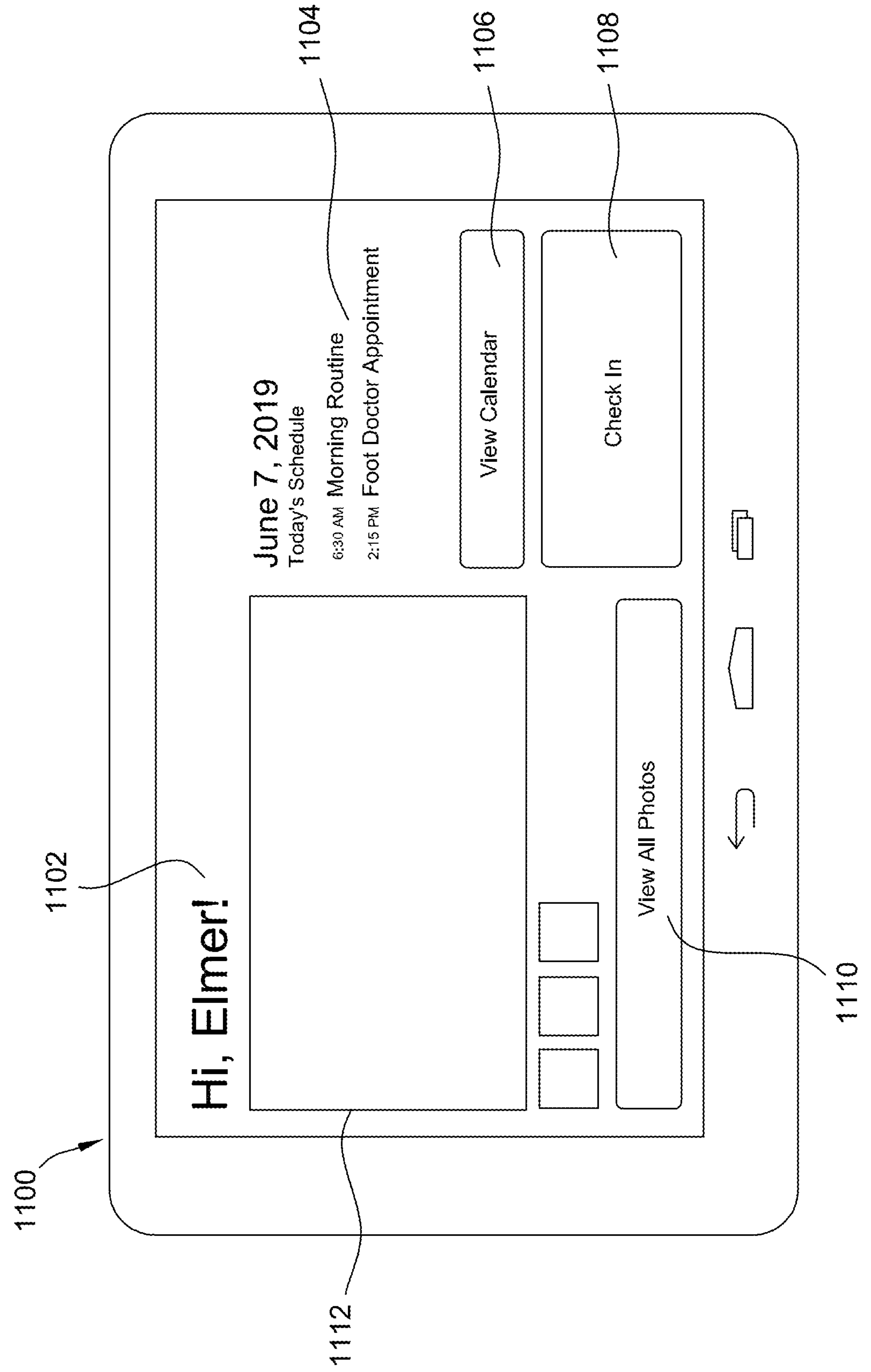
FIG. 11A is a screenshot of one example user home page of an engagement and care support application illustrated in FIG. 1.

FIG. 11A shows an example user home page 1100 displayed on a device associated with the user that the user may be directed to when the device is synced with the application. User home page 1100 may include a welcome greeting 1102 and a list 1104 of daily tasks scheduled for the user. User home page 1100 may further include a "View Calendar" button 1106 that, when pressed, may cause the application to display a detailed calendar of the user (not specifically shown). User home page 1100 may further include a "Check In" button that, when pressed, may notify the caregivers (e.g., in message 1202 and 1302 of user home screen 1200 and 1300, shown in FIGS. 12 and 13, respectively) that the user has checked in. User home page 1100 may also include media 1112 shared with the user by the caregivers and a "View All Photos" button 1110 that, when pressed, causes the application to display all media 1112 shared with the user.

Figure 11B:
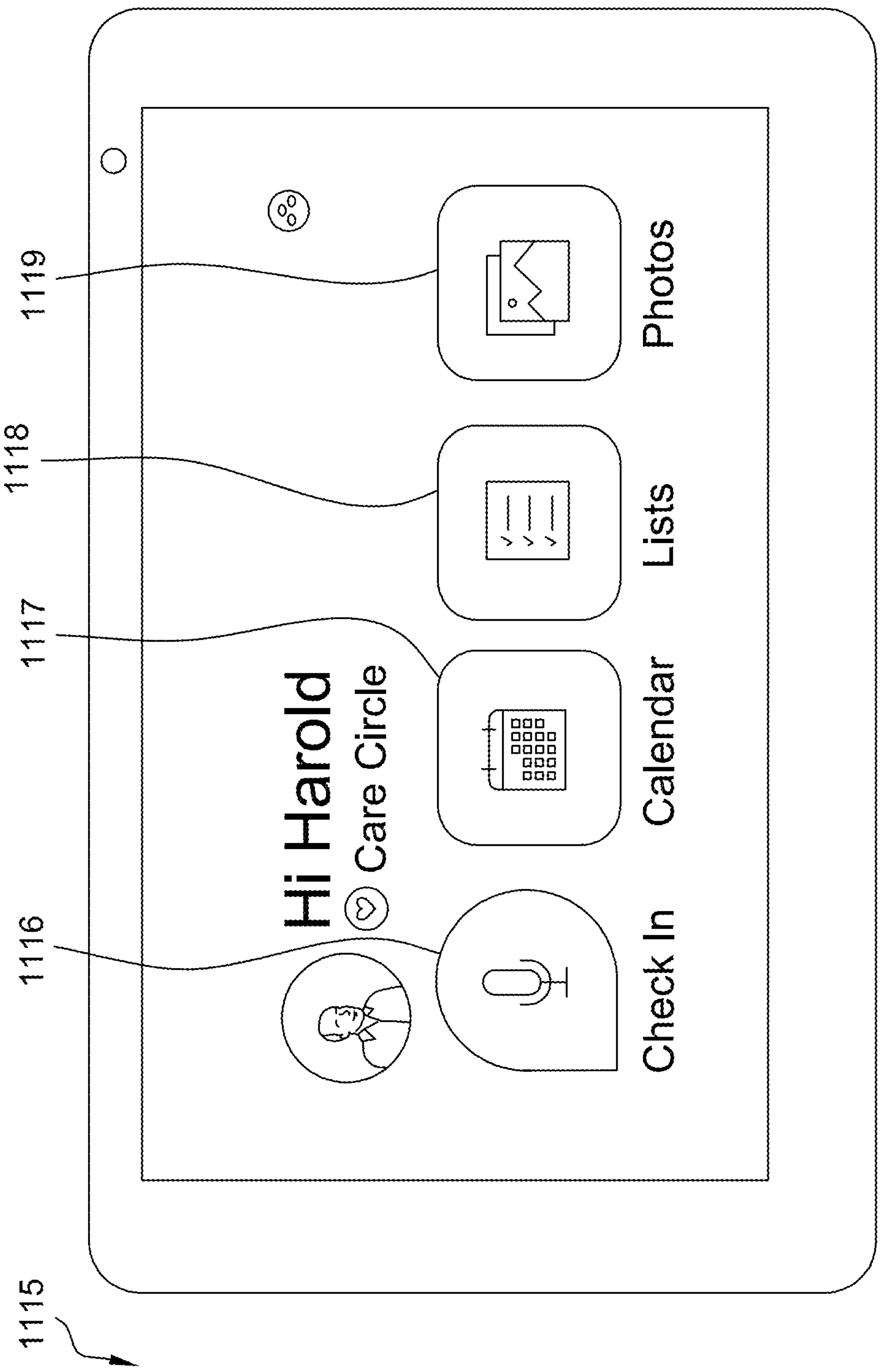
FIG. 11B is a screenshot of another example user home page of an engagement and care support application illustrated in FIG. 1.
Figure 11C:
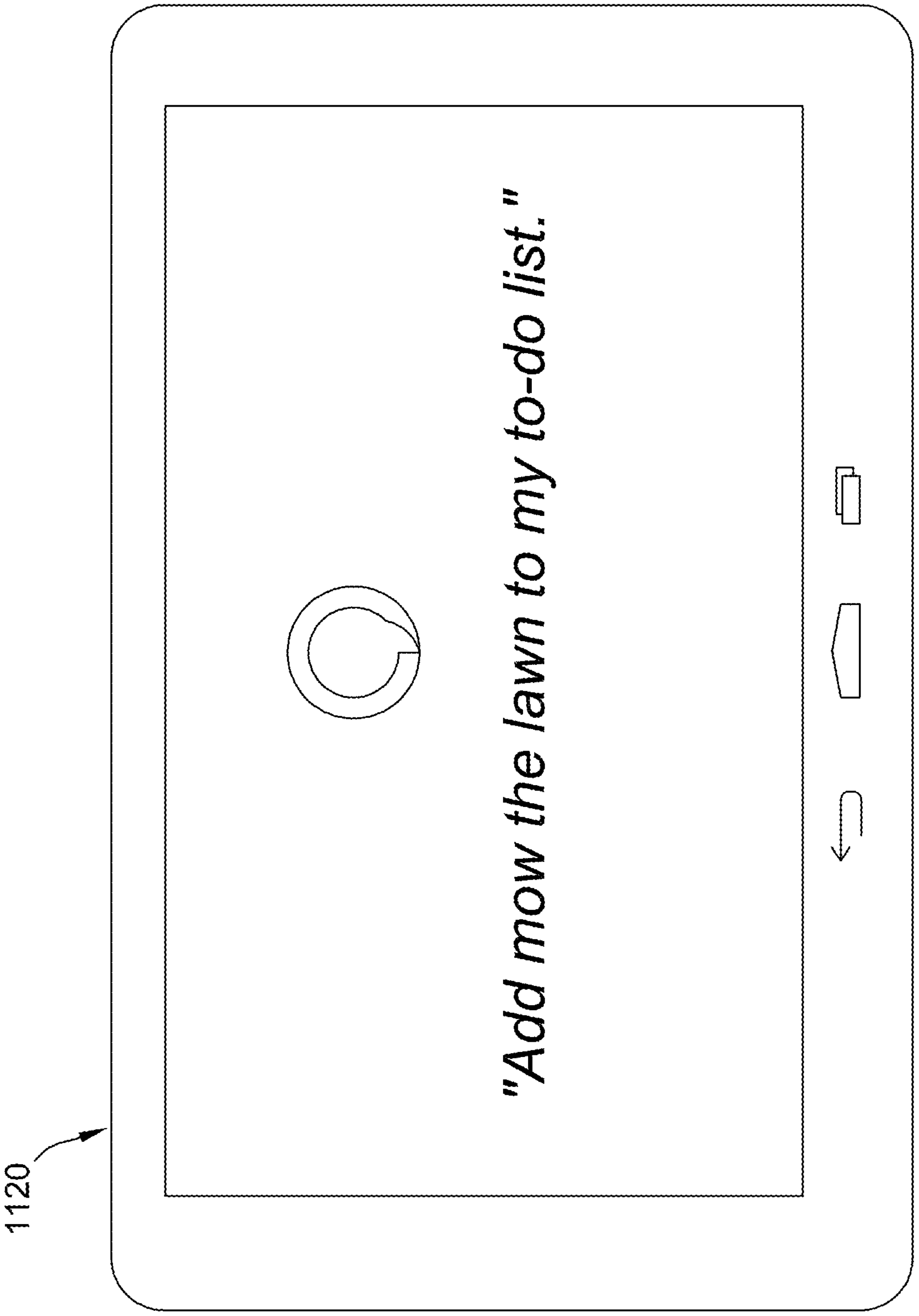
FIGS. 11C-11L are screenshots of example user interaction pages of an engagement and care support application illustrated in FIG. 1.
Figure 11D:
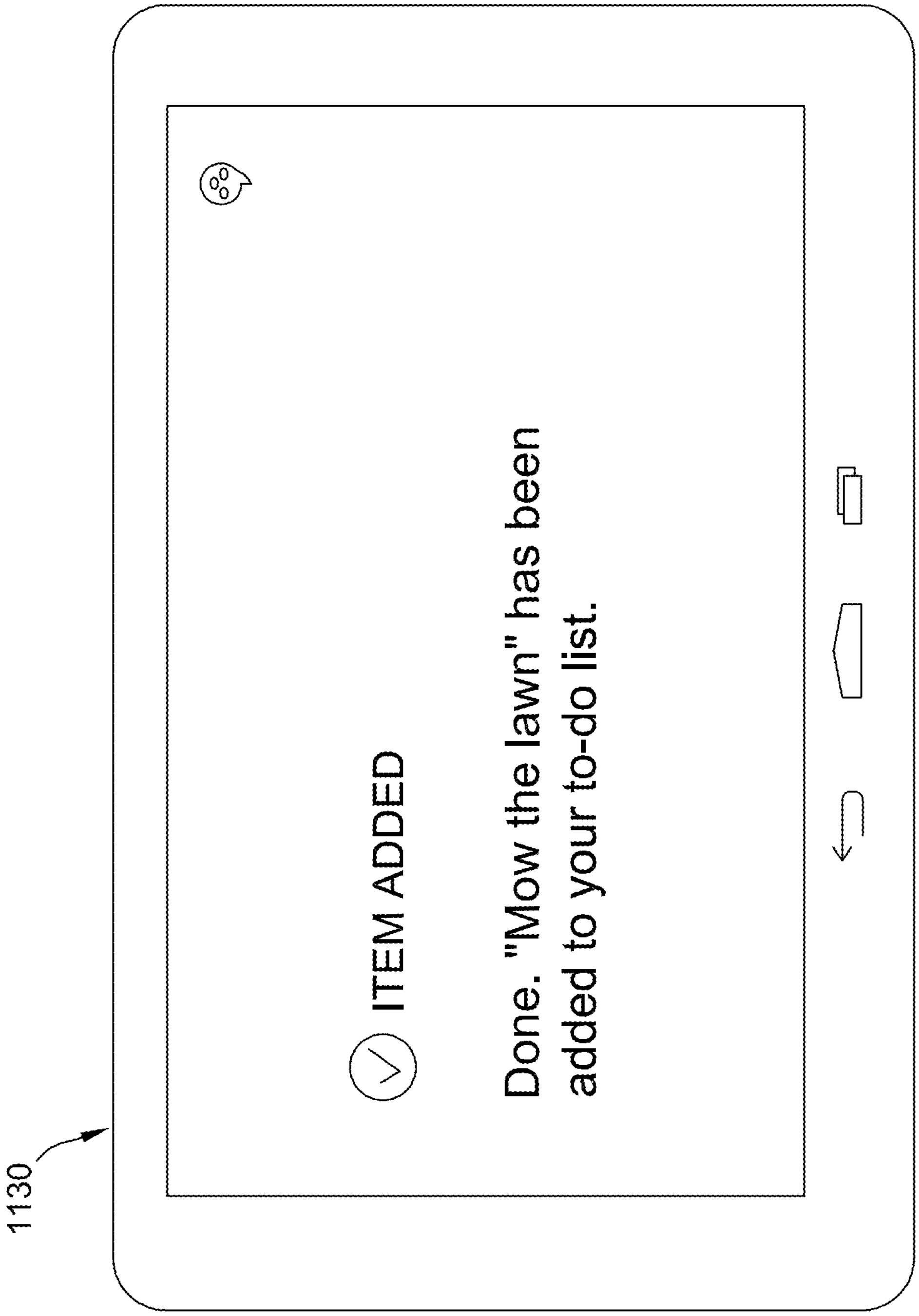
Figure 11E:
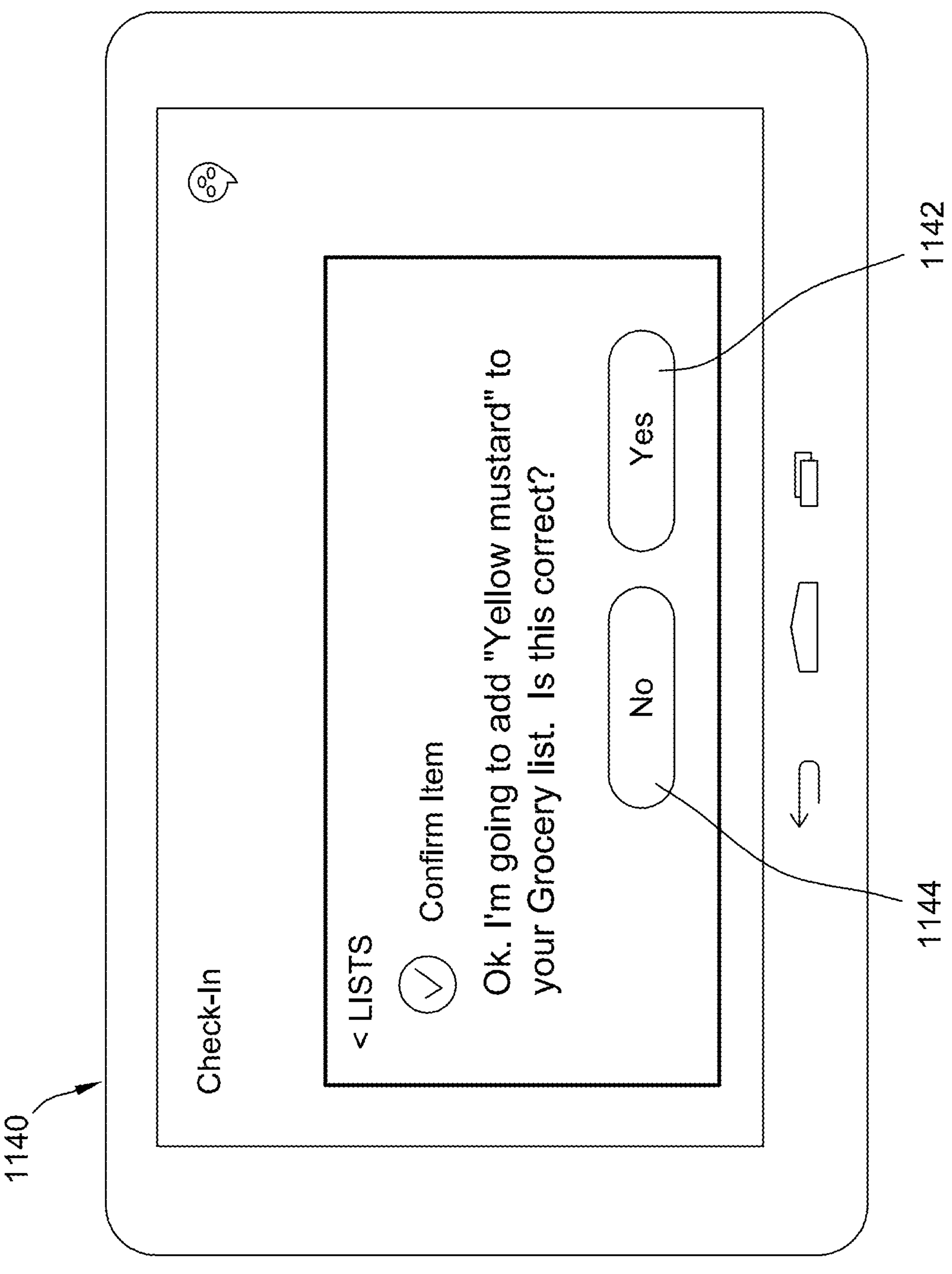
Figure 11F:
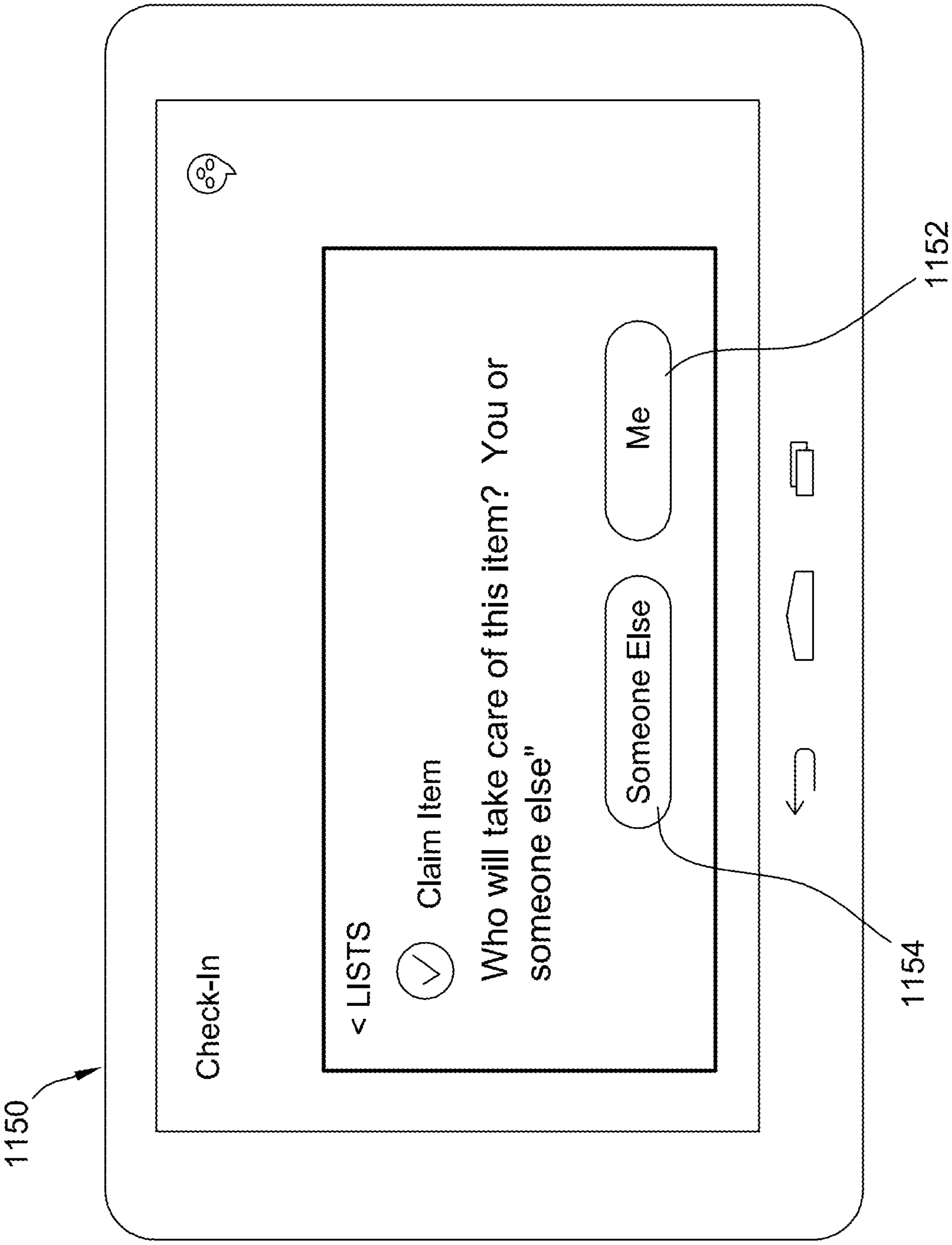
Figure 11G:
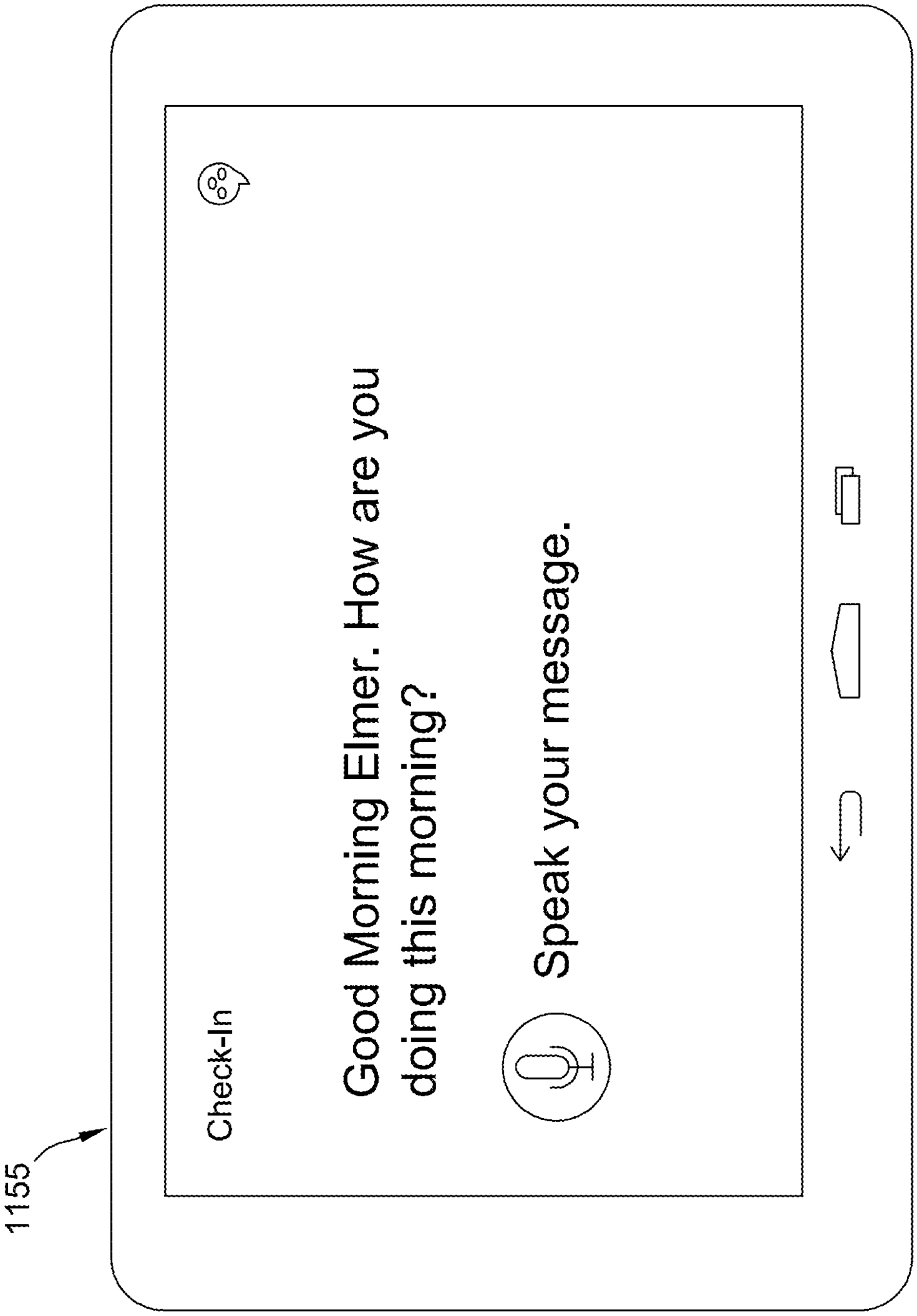
Figure 11H:
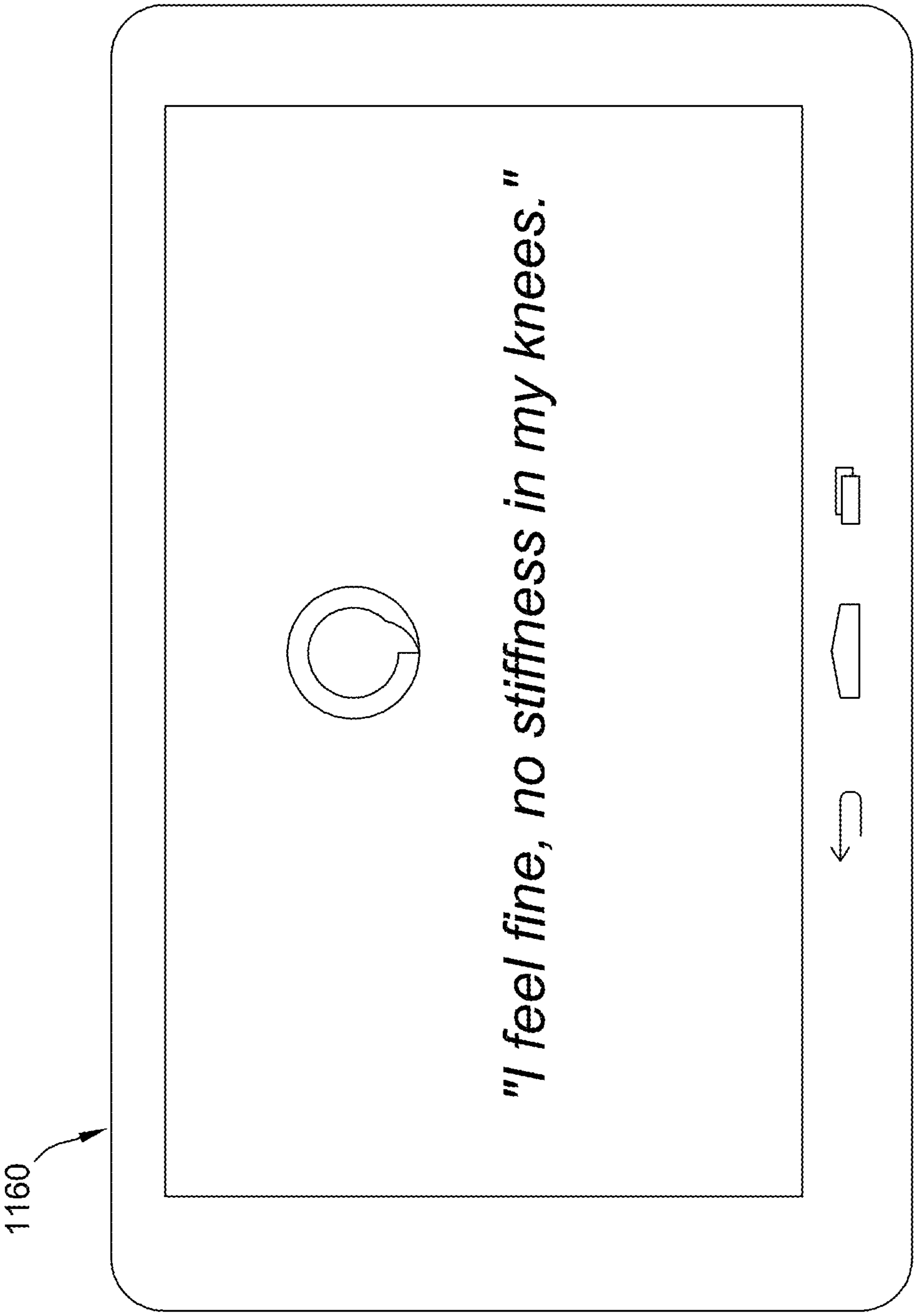
Figure 11I:
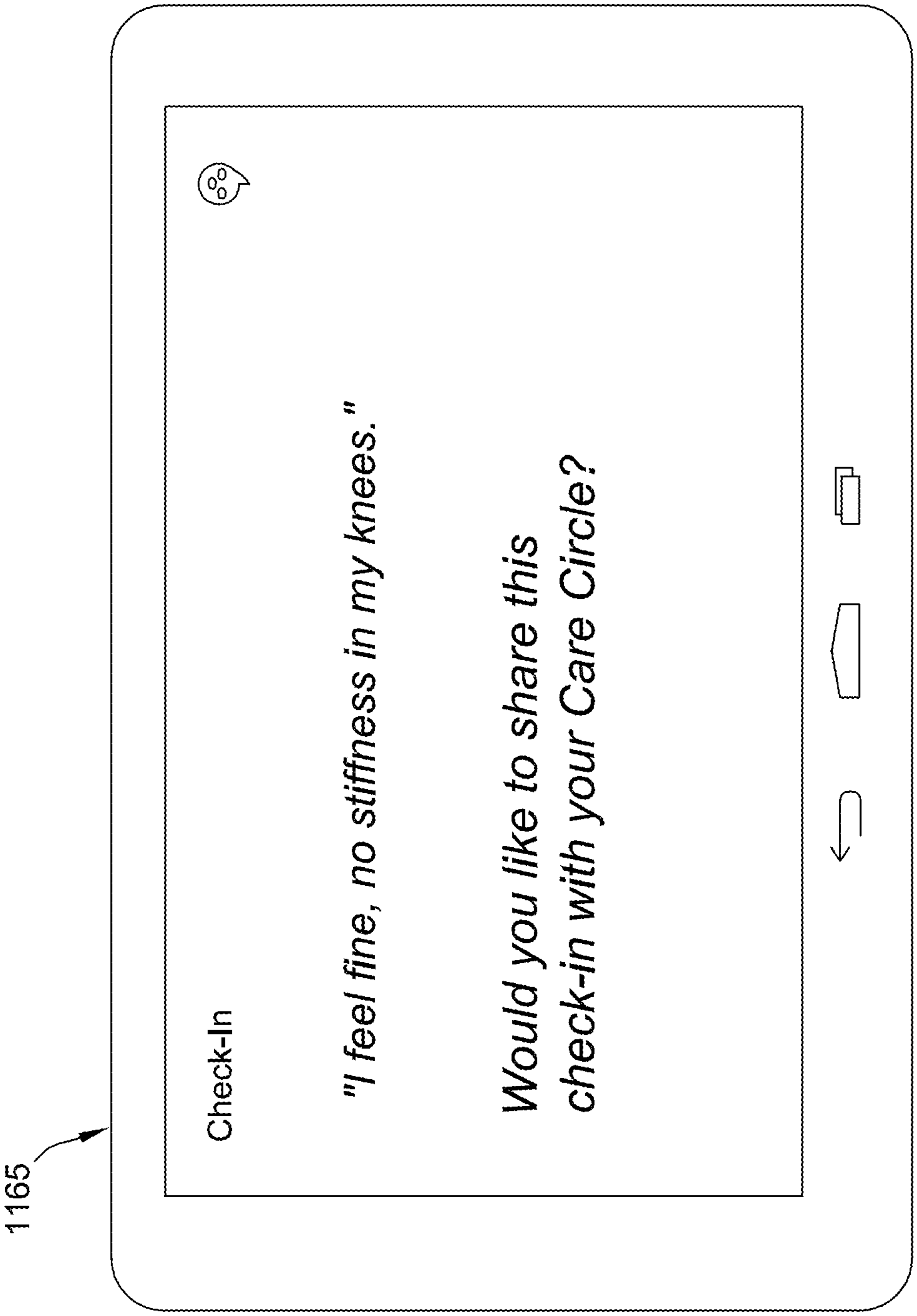
Figure 11J:
Figure 11K:
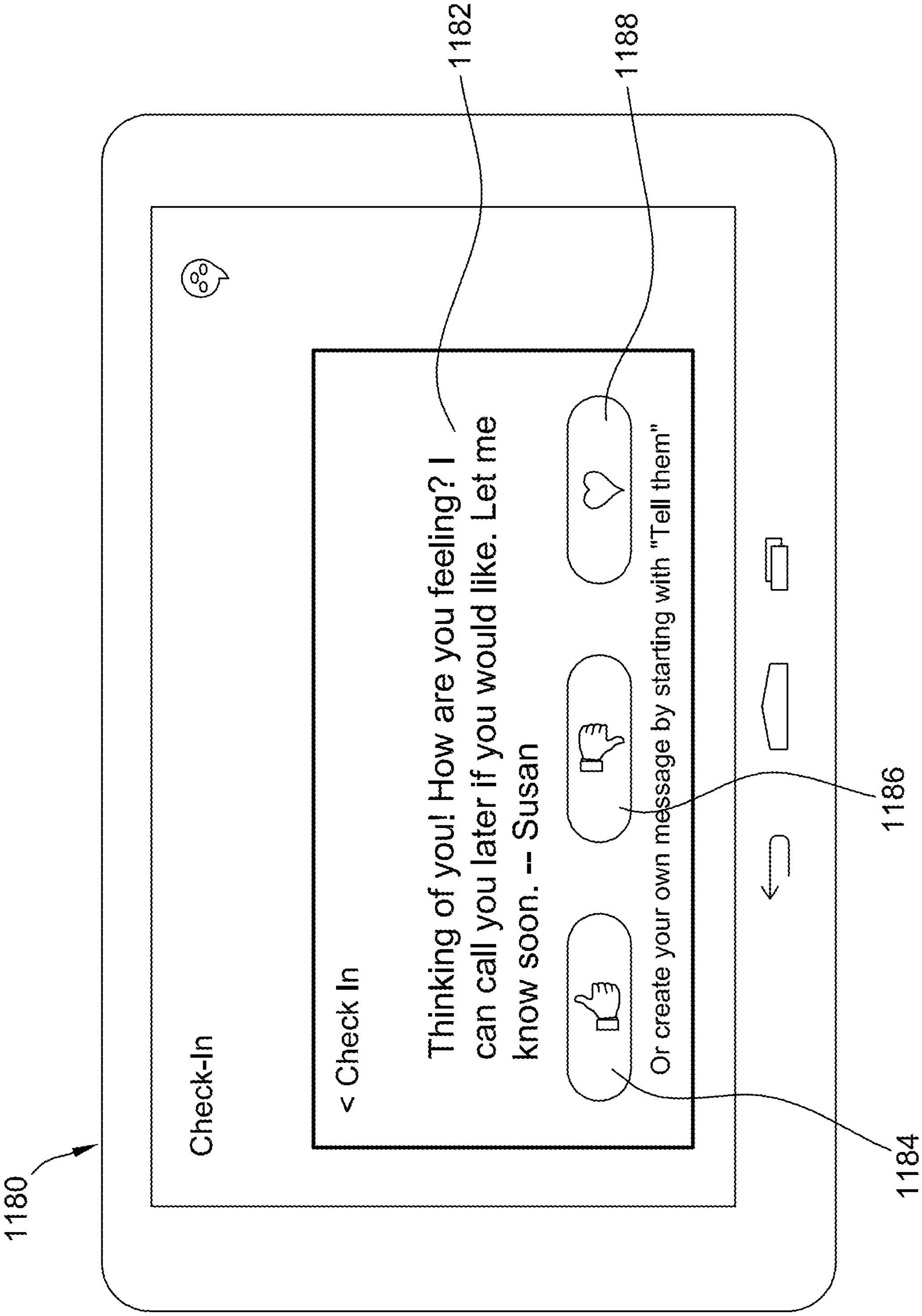
Figure 11L:
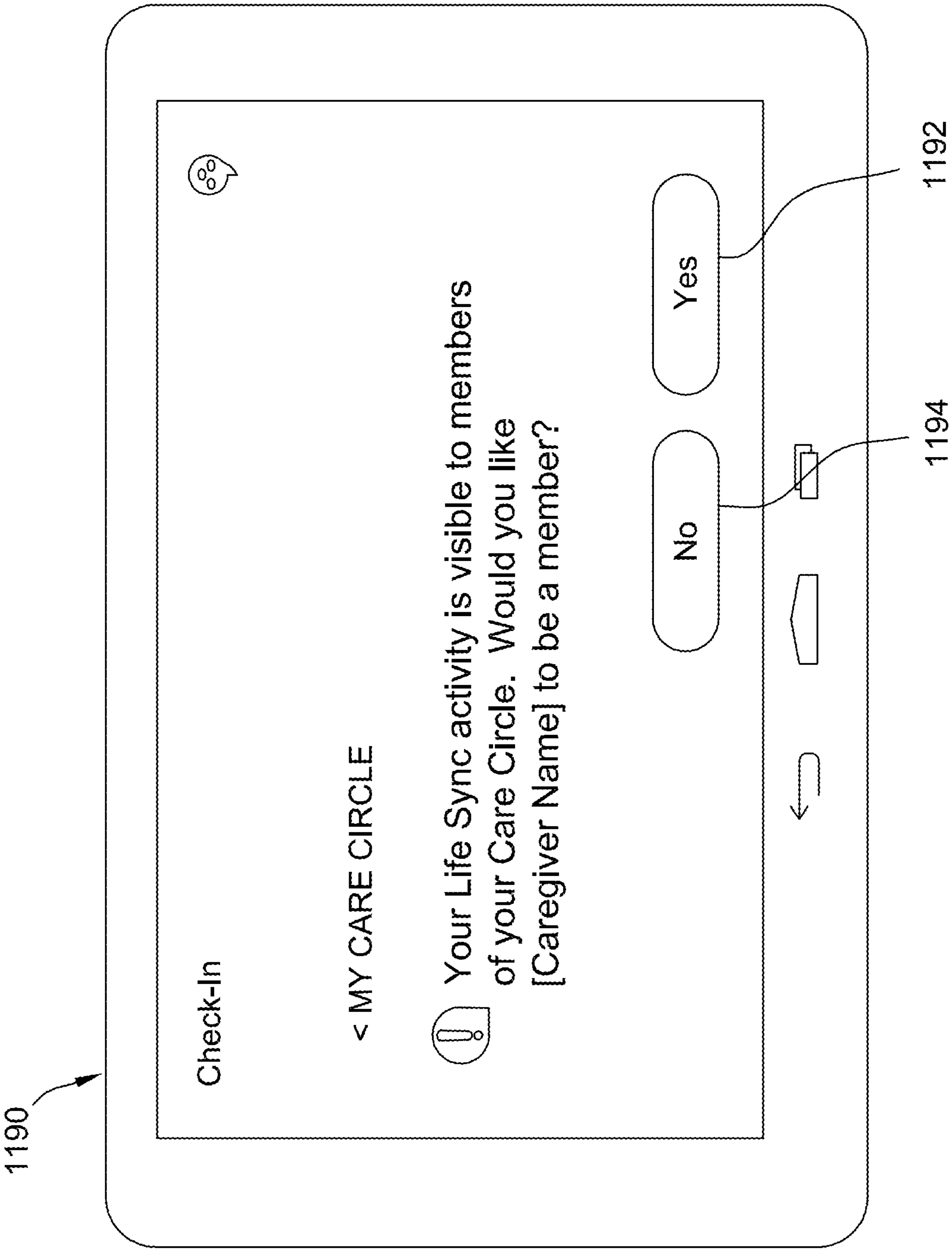

FIG. 11B shows an alternative user home page 1115 displayed on a device associated with the user that the user may be directed to when the device is synced with the application. User home page 1115 may include a "Check In" button 1116 that, when pressed, functions substantially the same as button 1108 of FIG. 11A. That is, button 1116, when pressed, may notify the caregivers (e.g., in message 1202 and 1232 of user home screen 1200 and 1230, shown in FIGS. 12A and 12B, respectively) that the user has checked in. Home page 1115 may further include a "Calendar" button 1117 that, when pressed, may cause the application to display a screen showing the calendar of the user (e.g., displayed as a daily calendar, a weekly calendar, a monthly calendar, etc.). Home page 1115 may further include a "Lists" button 1118 that, when pressed, may cause the application to display a screen showing lists associated with the user (e.g., a grocery list, a to-do list, etc.). User home page 1115 may also include a "Photos" button 1119 that, when pressed, may cause the application to display photos shared with the user.

FIGS. 11C-11L show user interaction pages 1120, 1130, 1140, 1150, 1155, 1160, 1165, 1170, 1180, and 1190. User interaction pages 1120 and 1130 are displayed on the application when the user interacts with the application. For example, user interaction page 1120 displays that the user used voice-activation to command the application to "Add mow the lawn to my to-do list." User interaction page 1130 displays that the application received the command from the user as shown in user interaction page 1120 and added the command to the to-do list of the user. User interaction page 1140 displays that the user used a command (e.g., either a voice command or pressed button 1118 of user interaction screen 1115) to add "yellow mustard" to their "Grocery list." User interaction page 1140 includes a "Yes" button 1142 that, when pressed, causes the application to add yellow mustard to the Grocery list and display user interaction page 1150, and a "No" button 1144 that, when pressed, causes the application to not add yellow mustard to the Grocery list and return to, for example, user home page 1110 or alternative user home page 1115. User interaction page 1150 includes a prompt for the user about whether the user will handle the newly added Grocery list item or if the user would like somebody else (e.g., a caregiver) to handle the newly added Grocery list item. User interaction page 1150 includes a "Me" button 1152 that, when pressed, causes the application to add the newly added Grocery list item to the lists of the user and then display, for example, user home page 1110 or alternative home page 1115, and a "Somebody else" button 1154 that, when pressed, causes the application to add the newly added Grocery list item to the lists of one of the caregivers of the user. Accordingly, the "Somebody else" button 1154, when pressed, may cause the application to display a list of the caregivers associated with the user (not shown) such that the user can pick the caregiver to assign the task to.

User interaction pages 1155, 1160, 1165, 1170, and 1180 are displayed on the application when the application actively interacts with the user for a check in. For example, user interaction page 1140 displays that the application has prompted the user to check-in via an audio prompt (e.g., asking the user "How are you this morning?"). User interaction page 1160 displays that the user used a voice command to respond to the application that the user is feeling fine (e.g., by saying, "I feel fine. No stiffness in my knees.")

User interaction page 1165 displays that the application received the response of the user and includes a prompt for the user to decide whether to share the check-in with the caregivers (e.g., the application asks the user, "Would you like to share this check-in with your care circle?"). User interaction page 1170 displays that the application received the response of the user to the prompt of user interaction page 1165 (e.g., the user responded that the user would like to share their check-in with their care circle and the application displays that the check-in has been shared). User interaction page 1180 displays an alternate way for the user to check-in. Specifically, user interaction page 1180 displays a message 1182 from a caregiver asking the user to check in with the caregiver soon. Further, user interaction page 1180 includes three check-in buttons, a first check-in button 1184, a second check-in button 1186, and a third check-in button 1188. The first check-in button 1184, when pressed or commanded to be pressed (e.g., via voice command), causes the application to send a message to the caregiver associated with the message 1182 that the user is doing well today. The second check-in button 1186, when pressed or commanded to be pressed (e.g., via voice command), causes the application to send a message to the caregiver associated with the message 1182 that the user is not doing well today. The third check-in button 1188, when pressed or commanded to be pressed (e.g., via voice command), causes the application to send a message to the caregiver associated with the message 1182 that the user feels loved today. Accordingly, when any of first, second, and third check-in buttons 1184, 1186, and 1188 is pressed or commanded to be pressed, the application counts the user as checked-in for the day.

User interaction page 1190 displays that a caregiver has been added to the Care Circle and prompts the user to accept or deny the user. User interaction page 1190 includes a "Yes" button 1192 and a "No" button 1194. The "Yes" button 1192, when pressed or commanded to be pressed (e.g., through voice command), causes the application to add the respective caregiver to be added to the Care Circle of the user. The "No" button 1194, when pressed or commanded to be pressed (e.g., through voice command), causes the application to deny the respective caregiver access to the Care Circle of the user. Accordingly, the application allows the user to control the members of the Care Circle of caregivers associated with the user.

Figure 12B:
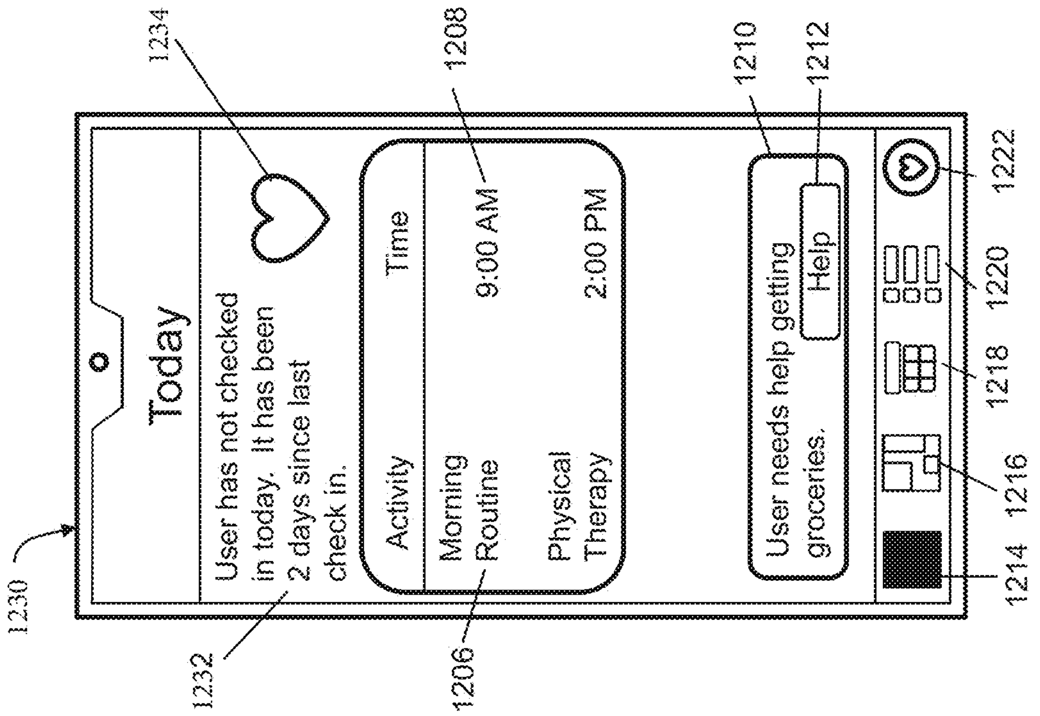
FIGS. 12A and 12B are screenshots of example caregiver home screens of an engagement and care support application illustrated in FIG. 1.
Figure 12A:
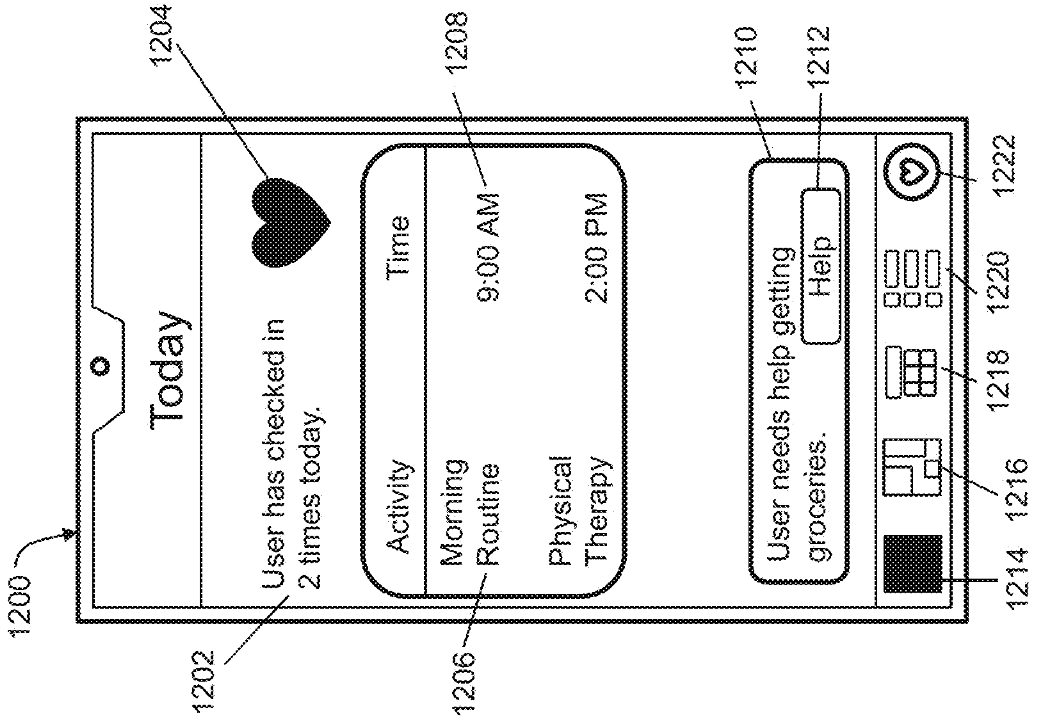

FIGS. 12A and 12B are examples of caregiver home screens 1200 and 1230. For example, caregiver home screens 1200 and 1230 may be the first screen that is displayed when the caregivers log-in to the application after registering the care team has been completed (e.g., in user care team page 1000). Caregiver home screens 1200 and 1230 may be substantially similar and may include a list 1206 of activities scheduled for the user and times 1208 associated with the activities. Caregiver home screens 1200 and 1230 may further include a notification 1210 of what the user needs help with (e.g., unassigned tasks) and a button 1212 that, when pressed, cause the application to assign the task of notification 1210 to the caregiver.

Caregiver home screens 1200 and 1230 may further include navigation buttons 1214, 1216, 1218, 1220, and 1222 that, when pressed, cause the application to display different screens of the application. For example, pressing button 1214 may cause the application to display one of caregiver home screens 1200 and 1230. Caregiver home screens 1200 and 1230 may further include a message 1202 and 1232, respectively, that may be accompanied by a logo 1204 and 1234. For example, when message 1202 and/or 1232 indicates that the user has checked-in for a specific day, logo 1204 and/or 1234 may be filled in (e.g., as shown in logo 1204). When message 1202 and/or 1232 indicates that the user has not checked-in for a specific day, logo 1204 and/or 1234 may not be filled in (e.g., as shown in logo 1234).

Figure 13A:
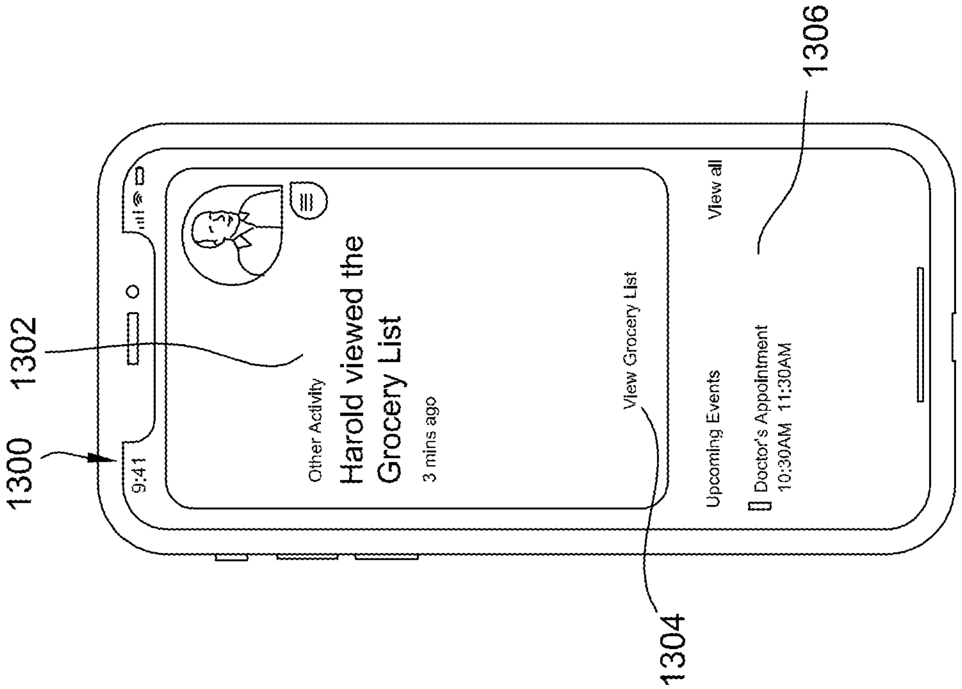
FIGS. 13A and 13B are screenshots of further example caregiver home screens of an engagement and care support application illustrated in FIG. 1.
Figure 13B:
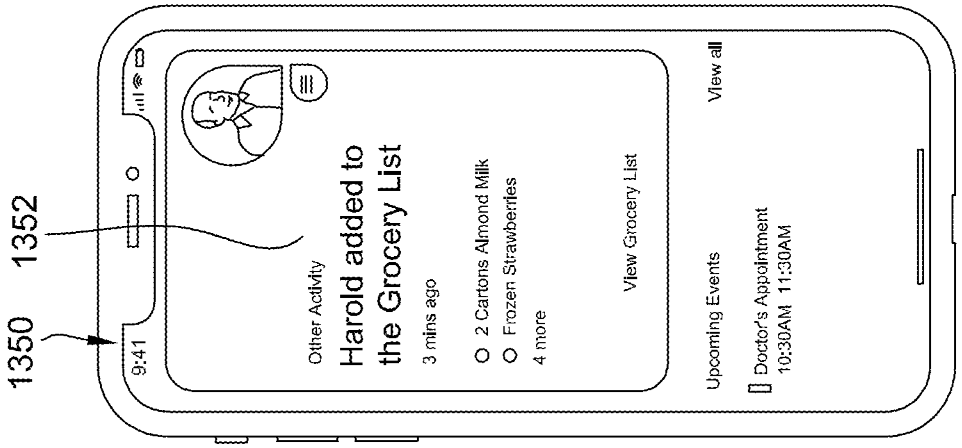

FIGS. 13A and 13B are alternative examples of caregiver home screens 1300 and 1350. For example, caregiver home screens 1300 and 1350 may be the first screen that is displayed when the caregivers log-in to the application after registering the care team has been completed (e.g., in user care team page 1000). Caregiver home screens 1300 and 1350 may include an action button 1304 that, when pressed, may cause the application to display a screen related to the action button (e.g., a grocery list view screen). Caregiver home screens 1300 and 1350 may further include an upcoming events list 1306 that display upcoming events scheduled for and/or associated with the user (e.g., a doctor's appointment scheduled at 10:30 A.M.).

Caregiver home screens 1300 and 1350 may be substantially similar and may include a user activity message 1302 and 1352. User activity messages 1302 and/or 1352 may display the most recent user activity and/or interaction with the application. For example, user activity messages 1302 and/or 1352 may show that the user viewed a grocery list (e.g., as shown in user activity message 1302) and/or that the user added to the grocery list and list the items that the user added (e.g., as shown in user activity message 1352).

Figure 14:
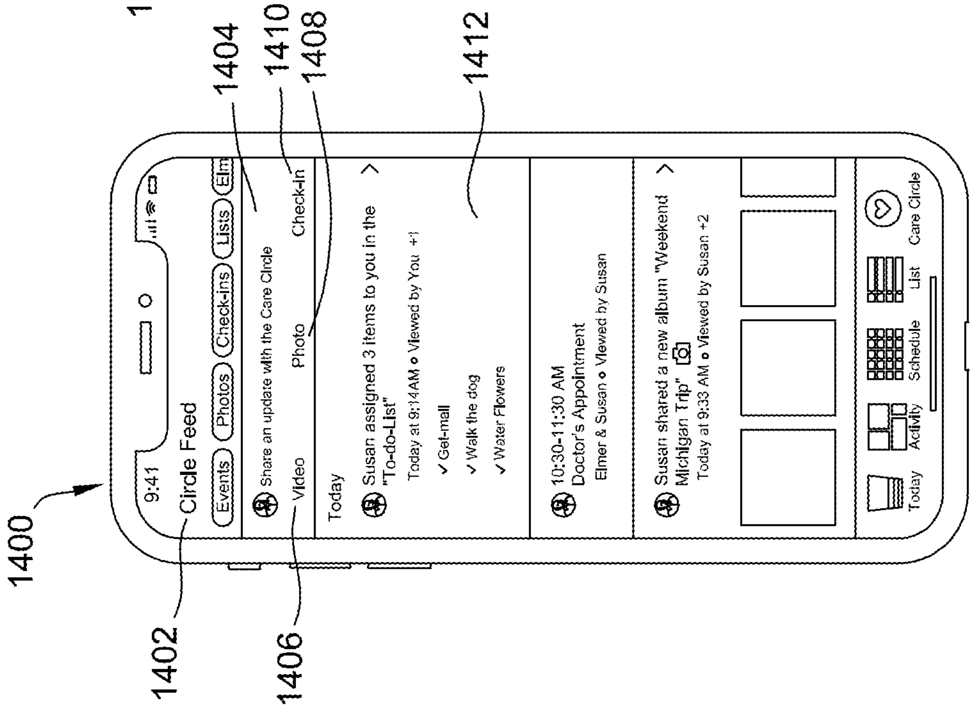
FIG. 14 is a screenshot of one example caregiver feed page of an engagement and care support application illustrated in FIG. 1.

FIG. 14 shows a caregiver feed page 1400 (e.g., which the application displays when button 1216 of FIGS. 12 and 13 is pressed). Caregiver feed page 1400 may include a header 1402, a field 1404 accompanied by a video button 1406, a photo button 1408, and a check-in button 1410, and a caregiver activity list 1412. The caregiver may give updates and include any information that the caregiver wishes to share with the other caregivers in field 1404. Video button 1406, when pressed, allows the caregiver to share a video on the application, photo button 1408, when pressed, allows the caregiver to share a photo (or multiple photos) on the application, and check-in button 1410, when pressed, allows the caregiver to check-in with the other caregivers (e.g., when the caregiver is carrying out an assigned task for the user and/or checking in on the user). Caregiver activity list 1412 shows a feed of recent caregiver activities (e.g., assigned tasks, adding appointments, sharing photos and/or videos, etc.).

Figure 15:
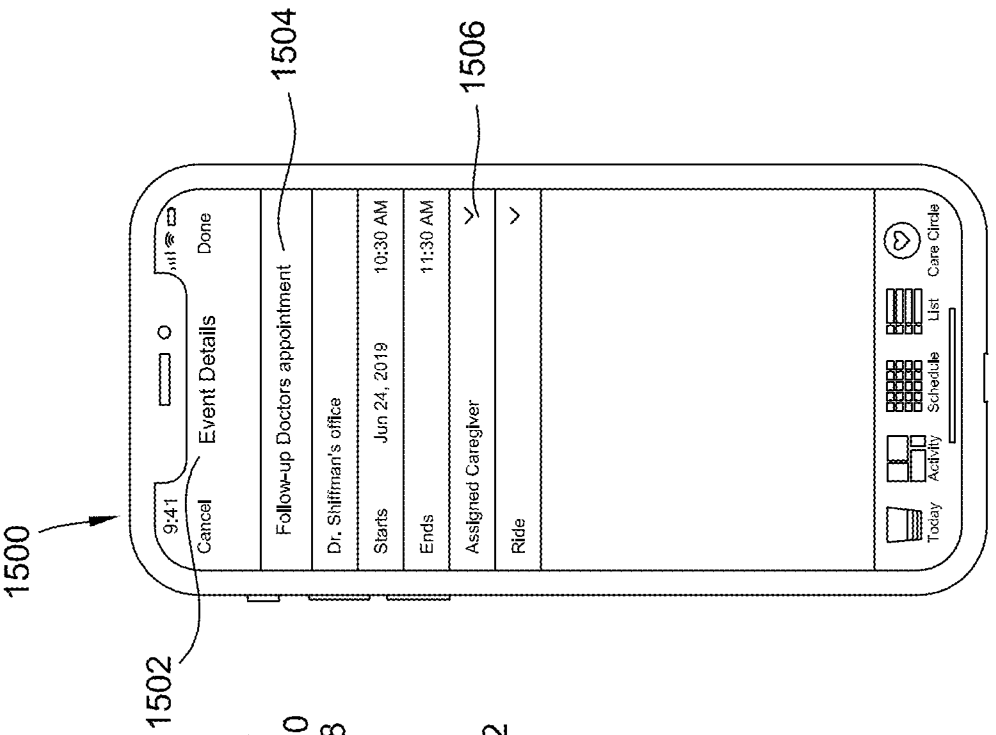
FIG. 15 is a screenshot of one example caregiver schedule page of an engagement and care support application illustrated in FIG. 1.

FIG. 15 shows a caregiver schedule page 1500 (e.g., which the application displays when button 1218 of FIGS. 12 and 13 is pressed) that allows the caregivers to add events and/or appointments to the care calendar of the user. Caregiver schedule page 1500 may include a header 1502, fields 1504, and pull-down bars 1506. The caregivers may provide information about the new event in field 1504, and the caregivers may use pull-down bars 1506 to assign the event to a specific caregiver.

Figure 17:
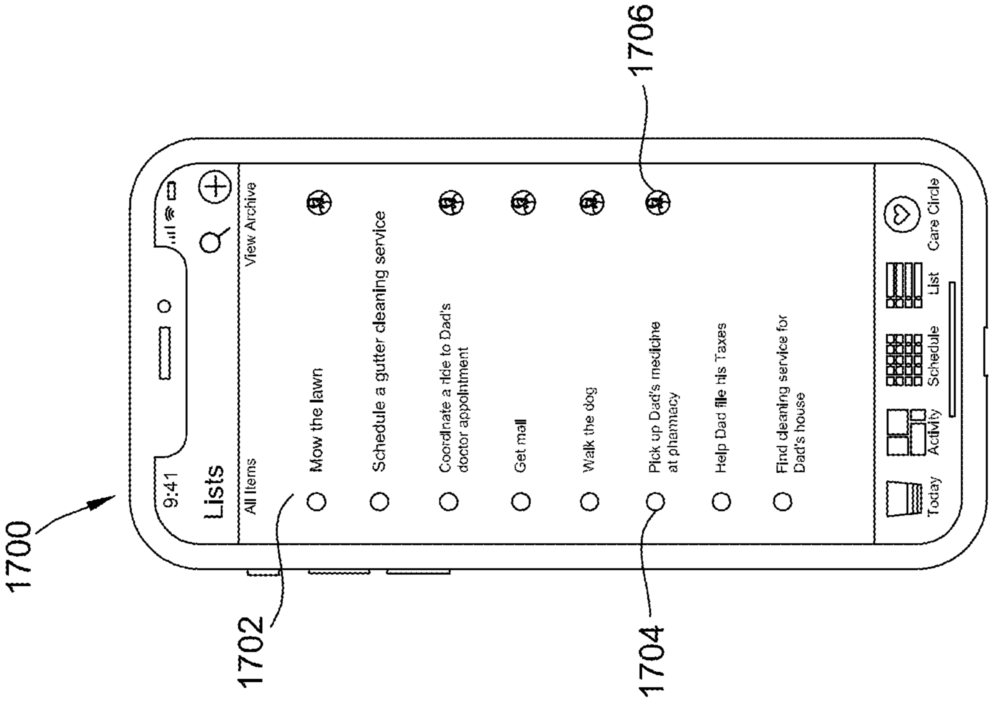
FIGS. 16 and 17 are screenshots of example caregiver list pages of an engagement and care support application illustrated in FIG. 1.
Figure 16:
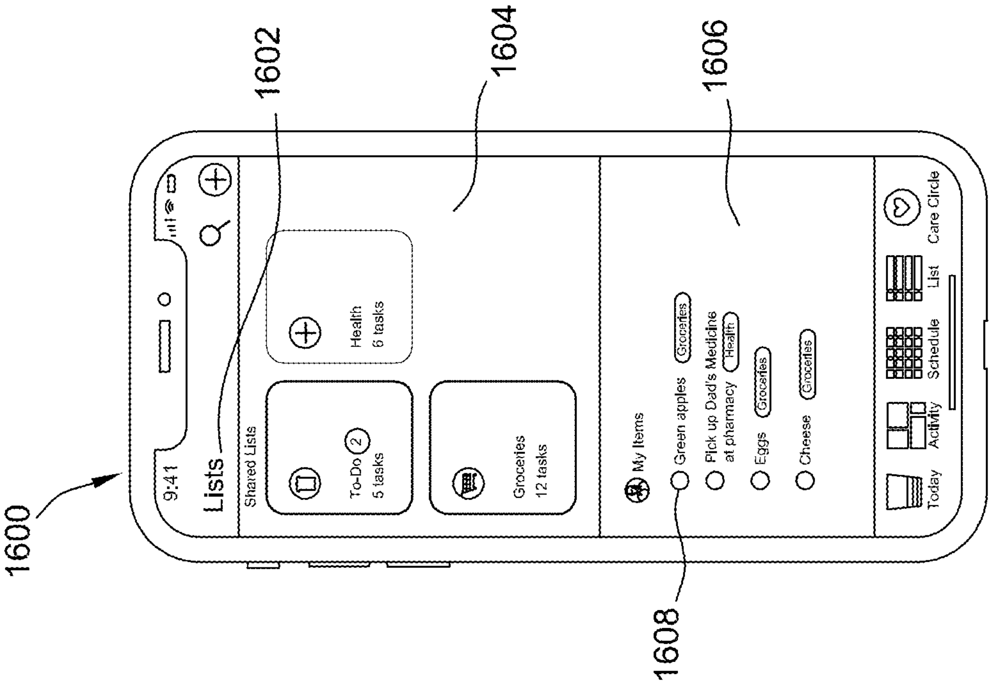

FIGS. 16 and 17 show caregiver list pages 1600 and 1700. Caregiver list page 1600 (e.g., which the application may display when button 1220 of FIGS. 12 and 13 is pressed) may include a header 1602, different categories of lists 1604, and list items 1606 that are assigned to the caregiver. List items 1606 may be accompanied by check circles 1608 that the caregivers may check when they have completed corresponding list item 1606 assigned to the caregivers. Caregiver list page 1700 may be displayed by the application when any of categories of lists 1604 is pressed. Caregiver list page 1700 may include list items 1702 that fit into the chosen category, and list items 1702 may be accompanied by check circles 1704 that the caregivers may check when they (or when they know other caregivers have) completed corresponding list item 1702. List items 1702 may further be accompanied by pictures 1706, and pictures 1706 may show the caregiver assigned to each of list items 1702.

Figure 18:
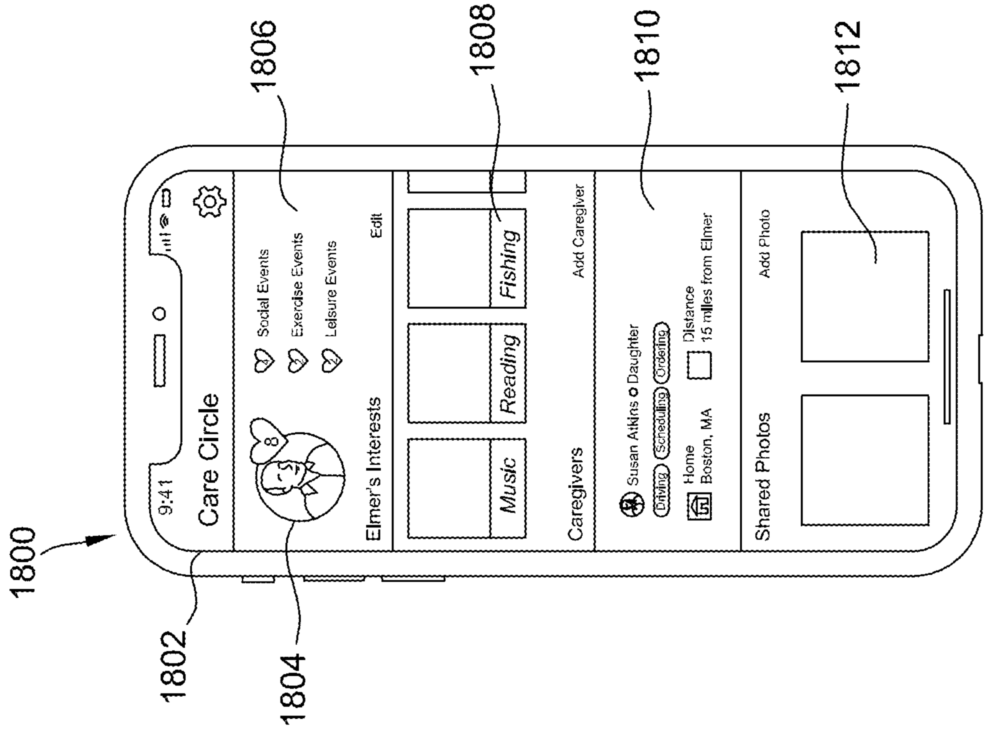
FIG. 18 is a screenshot of one example care circle page of an engagement and care support application illustrated in FIG. 1.

FIG. 18 shows a care circle page 1800 (e.g., which the application may display when button 1222 of FIGS. 12A and 12B is pressed). Care circle page 1800 may include a header 1802, an image 1804, groupings 1806 of events, interests 1808, caregiver profiles 1810, and shared photos 1812. Image 1804 may display an image of the user and/or of any of the caregivers. Groupings 1806 may show an overview of the number and types of events that the user has scheduled in the care calendar. Interests 1808 may allow the caregivers to choose certain interests 1808 of the user such that the application can better prepare a user profile. Caregiver profiles 1810 may show a brief profile of each of the caregivers of the care circle. Shared photos 1812 may show all photos shared by the caregivers of the care circle.

In other embodiments, the application may include additional features and functionality. For example, the application may present a user interface to the user and/or caregivers including an option for the user and/or caregivers to view or input additional data to their profile. The application may additionally provide an option for the user and/or caregivers to input, view, and/or edit medication information for the user. For example, the user and/or caregivers may be able to see the user's daily medication schedule and determine if the user is taking the medication (e.g., through a sensor, as described above).

Machine Learning & Other Matters

The computer systems and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on mobile computing devices, or associated with smart infrastructure or remote servers), and/or via computer executable instructions stored on non-transitory computer-readable media or medium.

In some embodiments, a care coordination support platform computing device is configured to implement machine learning, such that the care coordination support platform computing device "learns" to analyze, organize, and/or process data without being explicitly programmed. Machine learning may be implemented through machine learning methods and algorithms ("ML methods and algorithms"). In an exemplary embodiment, a machine learning module ("ML module") is configured to implement ML methods and algorithms. In some embodiments, ML methods and algorithms are applied to data inputs and generate machine learning outputs ("ML outputs"). Data inputs may include but are not limited to: user data, caregiver data, sensor data, assignment data, calendar data, task data, and/or alert data. ML outputs may include but are not limited to: user data, caregiver data, calendar data, task data, and/or assignment data. In some embodiments, data inputs may include certain ML outputs.

In some embodiments, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, combined learning, reinforced learning, dimensionality reduction, and support vector machines. In various embodiments, the implemented ML methods and algorithms are directed toward at least one of a plurality of categorizations of machine learning, such as supervised learning, unsupervised learning, and reinforcement learning.

In one embodiment, the ML module employs supervised learning, which involves identifying patterns in existing data to make predictions about subsequently received data. Specifically, the ML module is "trained" using training data, which includes example inputs and associated example outputs. Based upon the training data, the ML module may generate a predictive function which maps outputs to inputs and may utilize the predictive function to generate ML outputs based upon data inputs. The example inputs and example outputs of the training data may include any of the data inputs or ML outputs described above. For example, a ML module may receive training data comprising user data, caregiver data, and assignment data associated with the user data and caregiver data. The ML module may then generate a model which maps assignment data to aspects of user data and caregiver data. The ML module may then generate assignment data as a ML output based upon subsequently received user data and caregiver data.

In another embodiment, a ML module may employ unsupervised learning, which involves finding meaningful relationships in unorganized data. Unlike supervised learning, unsupervised learning does not involve user-initiated training based upon example inputs with associated outputs. Rather, in unsupervised learning, the ML module may organize unlabeled data according to a relationship determined by at least one ML method/algorithm employed by the ML module. Unorganized data may include any combination of data inputs and/or ML outputs as described above. For example, a ML module may receive unlabeled data comprising user data, caregiver data, and calendar data. The ML module may employ an unsupervised learning method such as "clustering" to identify patterns and organize the unlabeled data into meaningful groups. The newly organized data may be used, for example, to generate a model which associates user data and caregiver data to calendar data.

In yet another embodiment, a ML module may employ reinforcement learning, which involves optimizing outputs based upon feedback from a reward signal. Specifically, the ML module may receive a user-defined reward signal definition, receive a data input, utilize a decision-making model to generate a ML output based upon the data input, receive a reward signal based upon the reward signal definition and the ML output, and alter the decision-making model so as to receive a stronger reward signal for subsequently generated ML outputs. Other types of machine learning may also be employed, including deep or combined learning techniques.

The reward signal definition may be based upon any of the data inputs or ML outputs described above. For example, a ML module may implement reinforcement learning in generating assignment data for caregivers. The ML module may utilize a decision-making model to generate assignment data for caregivers based upon task data, and may further receive user-satisfaction data indicating a level of satisfaction experienced by a user and a caregiver who engaged in a transaction (e.g., the caregiver carrying out a task for the user). A reward signal may be generated by comparing the user-satisfaction data to an assignment score between the user and the caregiver.

Based upon the reward signal, the ML module may update the decision-making model such that subsequently generated assignment scores more accurately predict user satisfaction. For example, the ML module may determine that a specific caregiver has taken the user to four doctor's appointments. The user may enjoy the caregiver taking the user to the doctor's appointments, and the caregiver may enjoy taking the user to the doctor's appointments because the doctor's appointments may be close to the caregiver's house. Therefore, the user and the caregiver may both rate the "transaction" highly. Accordingly, the ML module may learn to automatically assign doctor's appointments to the specific caregiver.

Exemplary Virtual Care Circle Functionality

In one aspect, a digital solution is provided that will allow seniors stay independent longer in their homes, and that will use technology to create a connected care environment and platform. With the present embodiments, a new digital platform will provide a senior's care circle an easy way to stay connected and help coordinate care virtually. The digital platform may include a new application and chatbot for seniors, and new mobile applications for caregivers/family members/friends to electronically communication, and may be part of a subscription service.

The new, innovative digital platform and application/chatbot may improve the quality of life and care for seniors, and help give their family members added peace of mind, as well as provide unique voice solutions that help seniors' ability to communicate with their care circle from their homes.

In one aspect, the senior will have a voice and touch interface powered by the digital platform and/or caregiver circle application that can help them feel more connected and supported by their care circle, while delivering a personalized experience to them. The digital platform may connect to the care circle mobile app running on mobile device of the care circle members that provides updates and information throughout the day. The care circle can share information back to the senior-creating a virtual circle of support and two-way communication at any time of the day. In one embodiment, the digital platform may include or utilize Amazon's Echo Show™, or similar technologies.

Some of the features utilized by this digital solution include: (1) quick check-in to reassure care circle members; (2) interactive dashboard with scrolling list of daily activities; (3) tools to coordinate key tasks across the care circle; (4) smart-suggestions for events, content, and activities; (5) music and photos sent or delivered to the senior's computing device and/or application; (6) the ability to view the senior's full calendar with audio commands and visual display on their application; (7) social features to help everyone stay connected and up-to-date; and/or other features mentioned elsewhere herein.

The solutions discussed herein will be useful in helping manage care of a loved one, and help family members coordinate care with their aging loved one using a caregiver circle application. The application, chatbot, mobile applications, and digital platform will assist with activities of daily living, transportation, communication, and social connectivity that will be key in helping seniors' ability to "age in place."

A. Launching the Service

The care circle application, such as for use on mobile devices of caregivers and family members, may facilitate onboarding, setup, and/or profile creation. A family member or a senior may order a product, such as the Echo Show™M product, and download a mobile application to their mobile device. The family member may create a caregiver profile for themselves using the mobile application. Their profile may include their name and a profile photo, and other information and preferences.

The family member may create, using the mobile application, an account for the senior, such as their father or mother, that connects with the family member's profile and/or account. The family member may provide details about, and/or preferences of, the senior using the mobile application, such as the senior's name and a profile photo for the senior. The senior's profile may include other information, such as senior preferences for activities, events, movies, content, tv shows, music, restaurants, service providers, grocery stores, means of transportation, etc.

A sibling of the family member, for example, may also want to be part of the senior's care circle, and the family member may select an "Add Member" icon of the mobile application to add their sibling to the senior's care circle. The family member may also add, via the mobile application, details about their sibling, such as their name and email address, and other information. The family member may add additional caregivers/family members/friends to the senior's care circle using the mobile application.

The mobile application and platform may then send electronic invitations to the mobile devices or email addresses of the members of the care circle added by the originating family member. The electronic invitations may include a link to a mobile application for download that will allow the members of the care circle and/or senior to electronically communicate via the mobile application and digital platform.

The senior may launch or open the application on their computing device and/or on an Alexa-based or other chatbot-based product. After which, the senior may be greeted with a personalized dashboard on their mobile device, tablet, or laptop (or other computing device). The dashboard may include photos of family members, an icon or access to digital photos, an icon or access to a digital or virtual calendar or schedule of events, a "Check In" icon, today's date, and today's scheduled events (such as morning routine, or doctor's appointment). Once the senior opens or launches the application, all connected caregivers or designated caregivers that are part of the senior's care circle may receive an electronic notification that the senior opened the application via the mobile application running on their mobile devices. After which, as the senior provides updates (e.g., went to doctor, need groceries, etc.) on his/her activities/events and well-being via the application on their device and/or via the chatbot, all caregivers/family members in the senior's care circle may view the senior's updates on their respective mobile applications and mobile devices.

B. Managing the Virtual Care Circle

The care circle application may facilitate virtual care circle management and user invitation. If the senior has friends or neighbors that the senior wants to be able to participate in the senior's care circle, the senior may add the friend or neighbor to their virtual care circle via their application, mobile device or other computing device, and/or via the chatbot. Additionally or alternatively, one or more family members may add the friend or neighbor to the virtual care circle for the senior via their mobile care circle application and/or mobile device.

The senior and/or the one or more family members may add the friend's or neighbor's contact information, such as electronic email or text address, and other details, and then select the type of electronic notifications and communications that should be shared with the friend or neighbor via the senior's application or chatbot, or the mobile application running on a family member's mobile device, respectively. For instance, the senior and/or family members may want the friend or neighbor to know when help is needed for driving, scheduling, or ordering things, such as groceries or other items, for the senior.

After accepting an electronic invitation to join the senior's care circle, the friend or neighbor may download the mobile application onto their mobile device. The friend or neighbor may then be able to navigate a care circle feed that may consist of digital posts from all of the members in the care circle, as well as from the senior.

For instance, from the care circle feed, the friend or neighbor may be able to see on the mobile application that the original family member has assigned various items or tasks (such as items or task from a virtual to-do list) to the friend or neighbor (e.g., pick up groceries). After those items or tasks have been completed, the friend or neighbor may virtually check them off via the mobile application so that the family member and/or other members of the virtual care circle see that those items have been completed via the mobile application running on their mobile devices. The friend or neighbor may also virtually post an update using the mobile application to make sure everyone in the virtual care circle notices that he or she has completed the items assigned via the mobile application running on their respective mobile devices.

The friend and neighbor may also virtually post text updates about the well-being or health of the senior, and/or other events, via the mobile application. The family member or other members may comment or otherwise respond to the updates via the mobile application and/or their mobile devices.

C. Starting the Day Off Right

The virtual caregiver circle application may facilitate both "proactive" check-ins and "reactive" check-ins. For proactive check-ins, the senior may open the senior living application on their device or using Alexa (or other chatbot), prompting an automatic check-in. Alexa or another chatbot may greet the senior and ask how they are feeling, such as "Good Morning, Elmer. How are you doing this morning?" After which, the senior may respond verbally, and their verbal response may be converted to a text response or message by the application and/or chatbot-such as "I feel fine, no stiffness in my knees."

After which, the senior may be prompted by the chatbot and/or application to share his check-in with all caregivers, who can then view the senior's virtual post on the care circle feed. For instance, Alexa or another chatbot may ask "Would you like to share this check-in with your care circle?" If the senior decides to share his check-in with all caregivers/family members/friends, or one or more specific individuals, the chatbot or application may post the senior's update to the care circle feed, and then the chatbot may verbally respond to the senior: "Okay, your message has been shared."

The family members and other members of the care circle, may then receive an electronic notification via the mobile application on their mobile devices that the senior has checked-in for the day. After the senior checks-in, the senior may then view their digital dashboard on their computing device, and/or ask the chatbot what activities/events have scheduled for the day. The dashboard may then display a visual of the senior's scheduled activities for the day, and/or the chatbot may verbally detail the activities for the senior, such as "Call Addison at 10:30 am," or detail the activity by type, time, and location ("Doctor's appointment, St. Joseph Hospital, at 1 pm").

For reactive check-ins, such as when the senior fails to actively check-in with the application and/or chatbot on their own, one or more family members or other members of the care circle may receive an electronic notification that the senior has not checked-in this morning nor interacted with the application and/or chatbot. After which, a family member or member of the virtual care circle may decide to give the senior a video or telephone call, using the mobile application. The senior may respond to video or telephone call using the application on their computing device or chatbot. For instance, the chatbot may ask the senior if the senior is alright, and the senior may respond-either by conversing with the chatbot or by using their application on their computing device-that the senior was having coffee with a friend this morning, thus providing peace of mind to the family member that the senior is doing fine.

D. Everyone Knows What's Going On

The caregiver circle application may facilitate collaborative scheduling and calendars. For instance, one or more family members/care circle members may be sent reminders about various activities or events of the senior, depending on settings. For instance, a primary family member in the virtual care circle may be sent reminders about doctor appointments for the senior in the morning of the appointment, and a notification of which member in care circle is responsible for ensuring the senior has transportation to the appointment. After the appointment, the member of the care circle responsible for the appointment may virtually post a message providing an update on how the appointment went to the care circle feed and provide digital access to the message to one or more members of the virtual care circle.

For instance, a daughter may virtually post "Dad's post-surgery results look great, range of motion is better than expected" via the mobile application on her mobile device. Other members of the virtual care circle may receive electronic notification of the daughter's update via wireless communication or data transmission and via the mobile application running on their respective mobile devices. For example, the daughter's brother may receive, via his mobile care circle application, an electronic notification that his sister virtually posted an electronic update on the status of their father, such as "Susan posted an update about Dad's Doctor's appointment this morning." After which, the brother and other members of the virtual care circle may view the daughter's update on the status of the senior ("Dad") via the mobile application running on their respective mobile devices.

Then, continuing with this example, the daughter may create a virtual follow-up event, such as a follow-up doctor's appointment as a follow-up event, via her mobile application to add to the senior's virtual calendar viewable by one or more of the members of the virtual care circle. After which, one or more members in the virtual care circle may receive, depending upon individual permissions, an electronic notification of the seniors' next medical appointment (e.g., "Susan created a Follow-up Doctor's Appointment event"), and/or view the senior's updated virtual calendar that includes the next medical appointment.

Continuing with this example, the daughter may then designate whom receives electronic notifications of the next medical appointment; assign responsibility for the next medical appointment to one or more members of the virtual care circle; and/or schedule transportation for the senior to the next medical appointment via the mobile application running on her mobile device. After which, the senior may review and/or approve of the scheduled medical appointment, proposed responsible care giver, and/or proposed mode of transportation via their chatbot and/or application.

Additionally or alternatively, after the daughter posts the follow-up doctor's appointment event via her mobile application, a sibling may post a virtual update regarding the event using his mobile application and mobile device. For instance, brother Jake may virtually post "Going to drive Dad to his next appointment. Also, going to send him flowers!" via his mobile application. After Jake purchases the flowers through an online service or provider, such as Amazon, Jake may update the care circle feed and create a virtual event, via his mobile application, to alert the senior, his father in this example, of the delivery time, such as via the senior's chatbot and/or application.

Additionally or alternatively in this example, the service provider remote server may also have certain access to the mobile applications and/or the senior's chatbot and/or application. For instance, the service provider may provide a verbal or audible notice to the senior of a type of delivery and time of delivery via the senior's chatbot and/or application. Further, the mobile applications may provide real-time or near real-time video or images of the products being delivered to the senior-in this example, video or images of flowers being delivered to the senior.

E. Getting Things Done

The caregiver circle application may facilitate collaborative lists. For example, the senior may notice that his/her lawn needs to be mowed. To his/her virtual to-do list, the senior may add "Order landscaping/lawnmowing" via the seniors' chatbot and/or application. For instance, the senior may say "Alexa, open State Farm," and then "Add mow the lawn to my to-do list."

The senior's chatbot and/or application may then add mowing the lawn to the senior's virtual to-do list. For example, the senior's chatbot may respond: "Done. 'Mow the lawn' has been added to your to-do list."

After which, family members and/or care circle members may receive an electronic notification that the senior has updated their virtual to-do list. For instance, virtual care circle members may receive, via their respective mobile applications, an electronic message that indicates that the senior has updated their virtual to-do list-such as electronic notification saying "Elmer added an item to his to-do list. Let's help him complete some tasks."

After which, one or more designated family members and/or care circle members may take or assign responsibility for the item via a "To-do" icon on their respective mobile application, and/or the senior may also assign responsibility for the task via the senior's chatbot and/or application. For example, a primary family member responsible for assigning tasks to various members of the virtual care circle may assign the task to herself/himself, or the senior may assign the task to one of the care circle members via the senior's chatbot.

Then the senior, and/or assigning family member and/or care circle member, may view the listed items and also view who has been assigned and/or accepted responsibility for each virtual to-do item, such as via the senior's chatbot and/or application and/or via the virtual care circle members' mobile application, respectively. As examples, the virtual to-do items may include "Mow the lawn"; "Walk the dog"; "Get mail"; "Schedule an appointment"; "Schedule a gutter cleaning appointment"; "Coordinate a ride's to Dad's doctor's appointment"; "Pick up Dad's medicine at pharmacy"; "Help Dad prepare and file his taxes"; "Find cleaning service for Dad's house"; and/or other to-do items presented via a display or via the voice of a chatbot. The virtual to-do items may include other items, including those mentioned elsewhere herein.

A family member/care circle member may review the senior's virtual calendar via their mobile application, or a machine learning module, model, algorithm, or program may be programmed, to find a time to schedule a virtual to-do item for the senior. Additionally or alternatively, the senior may assign a virtual to-do item to one or more family members/care circle members via the senior's chatbot and/or application. For instance, a primary family member that has access to the senior's virtual calendar may decide upon a lawn service provider, and schedule a time and date to mow the senior's lawn using the mobile application running on their mobile device. The lawn service provider may be selected via the internet, such as selected via Amazon.com. Additionally or alternatively, the lawn service provider's website and/or Amazon.com may also be programmed with functionality to communicate or otherwise interact with the senior via the senior's chatbot to schedule a time for the lawn service provider to mow the senior's lawn.

Once the to-do item is assigned, electronic reminders may generated for the senior. For instance, voice-based reminders may be generated via the senior's chatbot. Text or visual-based reminders may be generated and displayed via the senior's application. Voice-based and text or visual-based reminders may also be sent to the mobile applications of one or more family members/care circle members. For instance, on the day of the lawn service, the daughter may be electronically notified via her mobile application when the lawn service will arrive and/or has arrived. Once the to-do items has been completed, the senior's virtual calendar may be updated to such that all virtual care members can see that the items has been completed via their mobile applications.

Exemplary Virtual Care Circle Platform & Functionality

Figure 19:
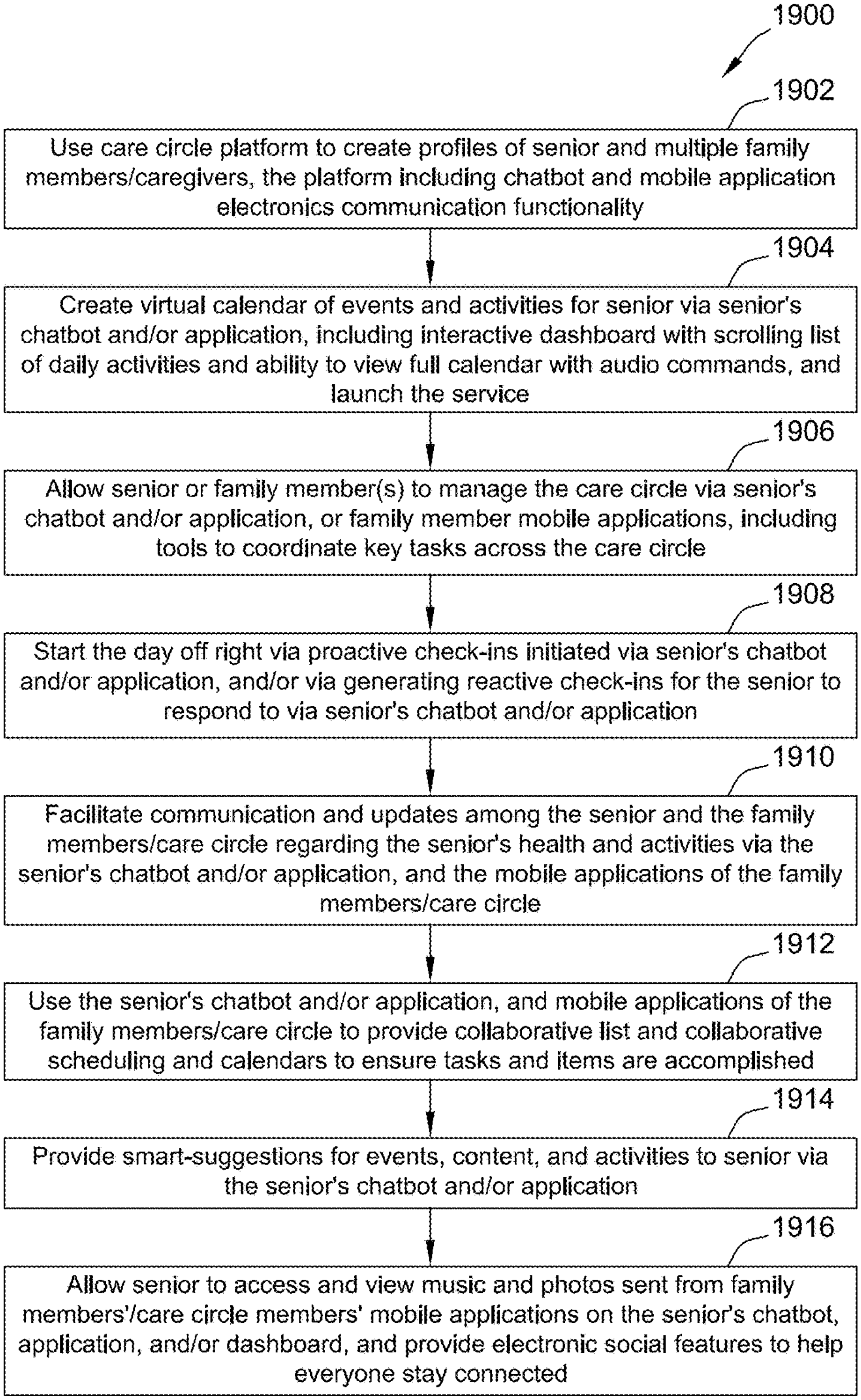
FIG. 19 illustrates an exemplary computer-implemented method of providing a care circle platform that includes chatbot and mobile application functionality that facilitates coordination of virtual care circle member communication and tasks.

FIG. 19 illustrates an exemplary computer-implemented method 1900 of providing a care circle platform that includes chatbot and mobile application functionality that facilitates coordination of virtual care circle member communication and tasks. The computer-implemented method 1900 may be implemented via one or more processors, transceivers, servers, sensors, applications, mobile applications, chatbots, and related technologies. In some embodiments, method 1900 may be carried out by a digital care circle platform. The digital care circle platform may be substantially similar to, and work in substantially the same way as ECSP server 102 (shown in FIG. 1), described above.

The computer-implemented method 1900 may include, via one or more processors and/or associated transceivers, using 1902 a digital care circle platform to create user profiles and preferences of a senior and multiple family members/caregivers with their permission or affirmative consent. The digital care circle platform may include chatbot functionality, and application and mobile application electronic communication functionality, such as that functionality discussed elsewhere herein, that permits electronic communication via computing devices and/or mobile devices over one or more radio frequency links via wireless communication or data transmission. For instance, the senior may use a chatbot and/or application to enter personal information to create their user profile and/or preferences. Members of the care circle may use a mobile application running on their respective mobile devices to enter personal information to create their respective user profiles.

The computer-implemented method 1900 may include, via one or more processors and/or associated transceivers, creating 1904 a virtual calendar of events and activities for the senior via the chatbot and/or application. The virtual calendar may include an interactive dashboard with a scrolling list of daily activities and events for the senior. The application may include the ability for the senior to view the full calendar after the senior enters one or more audible commands. The method 1900 may include launching the service, which may include activating the chatbot and application of the senior, as well as the mobile applications of the virtual care circle members, once the senior logs into or launches the application for the first time.

The computer-implemented method 1900 may include, via one or more processors and/or associated transceivers, allowing 1906 the senior and/or family members/designated members of the virtual care circle to manage the care circle via the senior's chatbot and/or application, or via the family members'/designated care circle member's mobile application, respectively. The method 1900 may include generating virtual tools that facilitate coordinating key tasks across the virtual care circle, such as assigning specific activities or events to be the responsibility of specific individuals within the virtual care circle.

The computer-implemented method 1900 may include, via one or more processors and/or associated transceivers, initiating 1908 "start the day off right" functionality. For instance, "proactive check-ins" may be generated and/or initiated via the senior interacting with their chatbot and/or application on their computing device. As an example, every morning the senior may check in with their chatbot and/or application at a given time to review their schedule, as well as provide an update to their care circle as to how they are feeling.

The computer-implemented method may also include generating "reactive check-ins" for the senior to respond to via the senior's chatbot and/or application. For instance, if the senior doesn't check in by 8 a.m., the chatbot and/or application may ask the senior if they are doing alright, and the senior may respond to, or converse with, the chatbot verbally or respond via the application textually or by touch.

Additionally or alternatively, a virtual care circle member may send a video, text or voice message to the senior that the senior receives via their chatbot and/or application. The senior may respond to the virtual care circle member's message via the chatbot and/or application. For instance, a virtual care circle member may send a text message "How are you doing today Dad?" via their mobile application. The senior's application may convert that text message to voice, and the senior's chatbot may verbally ask the senior: "How are you doing today Dad?" At which point, the senior may verbally respond to the chatbot "I am feeling well today. How are you?" After which, the conversation between the senior and the virtual care circle member may continue with the senior interacting with the chatbot to relay messages with the care circle member's mobile application.

The computer-implemented method 1900 may include, via one or more processors and/or associated transceivers, facilitating 1910 electronic and verbal communication and updates among the senior and the family members/care circle members regarding the senior's health/well-being and activities via the senior's chatbot and application, and the mobile application of the respective family members/care circle members. For instance, a virtual "care circle feed" may include updates posted by the senior using their chatbot or the application on their computing device, and/or updates posted by family member's/care circle member's via the mobile application running on their respective mobile devices. The updates may be related to the senior's health, well-being, events, activities, location, etc. The updates may include photos and/or text messages to create timeline of the senior's activities.

The computer-implemented method 1900 may include, via one or more processors and/or associated transceivers, generating, creating, and/or providing 1912 collaborative lists and/or collaborative scheduling to ensure necessary tasks and items are accomplished for the senior. For instance, the method may include allowing the senior to virtually post tasks or events that he/she needs help with completing using their chatbot and/or application. Care circle members may also virtually post tasks that need to be completed via their mobile applications. Care circle members may virtually volunteer for, or accept responsibility for, various task via their mobile application. The senior may virtually accept which volunteer care circle member to handle each task, or assign various tasks to specific individuals, via the senior's chatbot and/or application.

The computer-implemented method 1900 may include, via one or more processors and/or associated transceivers, providing 1914 smart-suggestions or recommendations for events, content, and/or activities to the senior via the senior's chatbot and/or application. For instance, based upon "likes" or preferences in the senior's profile, the senior's chatbot and/or application may recommend various events or activities to attend, and/or various online content to view, listen to, or read.

The computer-implemented method 1900 may include, via one or more processors and/or associated transceivers, allowing 1916 the senior to access and view music and photos sent or received from family members'/care circle members' mobile applications via wireless communication or data transmission over one or more radio frequency links. For instance, family members and/or care circle members may push or send photos, music, and/or content to the senior that the senior can review, view, or listen to on the senior's application. The virtual care circle members may also push or send music that the senior can listen to via the senior's chatbot or other digital platform. The computer-implemented method may include additional, less, or alternate functionality, including that discussed elsewhere herein.

Exemplary Virtual Care Circle Embodiments

In one aspect, a digital care circle platform for electronic communication (i) within a virtual care circle, and (ii) between a senior's chatbot and application, and a mobile application running on multiple care circle members' respective mobile devices may be provided. The digital care circle platform may include one or more processors, servers, sensors, wearables, and/or transceivers configured for wireless communication and/or data transmission over one or more radio frequency links between and/or among the senior's chatbot and application, and the mobile application running on each virtual care circle member's mobile device. The digital care circle platform may include, or be interconnected with on communication with, (i) a chatbot associated with the senior configured to receive one or more audible or verbal commands from the senior; (ii) an application associated with a computing device of the senior, the application electronically interacting with and/or communicating with the chatbot; and/or (iii) a mobile application running on each virtual care circle member's mobile device and associated with virtual care circle members, the mobile application configured to electronically communicate with the senior's chatbot and application running on the senior's computing device, such as via wireless communication or data transmission over one or more radio frequency links.

The digital care circle platform may be configured to accept "event" posts from the senior via the chatbot and application, and from each virtual care circle member via the mobile device running on their respective mobile devices. The digital care circle platform may be configured to detect pro-active check-ins that are automatically detected and/or generated by the senior verbally or audibly interacting with the chatbot and/or the senior accessing, viewing, or otherwise interacting with the application running on the senior's computing device. Once a pro-active check-in is detected, the digital care circle platform may be configured to generate an electronic communication detailing the pro-active check-in as a "pro-active check-in event," and (i) automatically virtually post the pro-active check-in event to a care circle feed access via the mobile application running on one or more virtual care circle member mobile devices, or (ii) otherwise transmit the electronic communication to the mobile application running on one or more virtual care circle member mobile devices to facilitate providing communication on the senior's current activity to the members of the virtual care circle and quick check-in functionality. The digital care circle platform may include additional, less, or alternate functionality, including that discussed elsewhere herein.

For instance, the digital care circle platform may be configured to, via one or more processors, sensors, servers, wearables, and/or transceivers: (a) actively monitor use of, and/or interaction with, the chatbot, application, and/or computing device by the senior; (b) detect that the senior has not used or interacted with the chatbot, application, and/or computing device for a predetermined amount of time; and (c) if so, automatically generate an electronic message to the senior, and transmit or send the electronic message to the chatbot, application, and/or computing device of the senior to facilitate quick check-ins and/or determining whether the senior needs assistance. Additionally or alternatively, the digital care circle platform may be configured to, via one or more processors, sensors, servers, wearables, and/or transceivers: when it is detected that the senior has not used or interacted with the chatbot, application, and/or computing device for a predetermined amount of time, automatically generate an electronic notification detailing such, and transmitting or otherwise sending the electronic notification to one or more virtual care circle member mobile devices to facilitate quick check-ins.

The digital care circle platform may be being configured to, via one or more processors, sensors, servers, wearables, and/or transceivers: (a) actively monitor use of, and/or interaction with, the chatbot, application, and/or computing device by the senior; (b) detect that the senior has not used or interacted with the chatbot, application, and/or computing device for a predetermined amount of time; (c) when it is detected that the senior has not used or interacted with the chatbot, application, and/or computing device for a predetermined amount of time, automatically generate an electronic notification detailing such, and transmitting or otherwise sending the electronic notification to one or more virtual care circle member mobile devices; and/or (d) open, access, or create an audible or verbal communication channel between the senior's chatbot and a virtual care circle member mobile device to facilitate a real-time conversation between the senior and the virtual care circle member, and/or quick check-ins.

The digital care circle platform may be configured to, via one or more processors, sensors, servers, wearables, and/or transceivers: scan the internet for preferred content (music, videos, articles, events, activities, etc.) for the senior based the senior's preferences identified or detailed in a virtual profile associated with the senior; and/or push preferred content, or otherwise providing links thereto, to the senior's chatbot and/or the application running on the senior's computing device.

The digital care circle platform may be configured to, via one or more processors, sensors, servers, wearables, and/or transceivers: (a) generate a virtual calendar of scheduled events and/or activities for the senior, the virtual calendar including a scrolling list of scheduled events and/or activities; and/or (b) display the virtual calendar of scheduled events and/or activities for the senior via the application on a display screen of the senior's computing device, and/or audibly or verbally detail the calendar of scheduled events and/or activities for the senior via the chatbot.

The digital care circle platform may be configured to, via one or more processors, sensors, servers, wearables, and/or transceivers: (i) receive or accept audible or verbal commends from the senior via the chatbot regarding details of an event or activity to add to their virtual calendar; and/or (ii) add the event or activity to the senior's virtual calendar.

The digital care circle platform may be configured to, via one or more processors, sensors, servers, wearables, and/or transceivers: (a) receive or accept audible or verbal commends from the senior via the chatbot regarding details of a task or item to add to their virtual to-do list; (b) add the task or item to the senior's virtual to-do list; and/or (c) generate and post an electronic notification detailing the task or item to the care circle feed accessible via the mobile application running on one or more virtual care circle member mobile devices to facilitate coordinating key tasks among the members of the virtual care circle.

The digital care circle platform may be configured to, via one or more processors, sensors, servers, wearables, and/or transceivers: (a) receive or accept audible or verbal commands from the senior via the chatbot regarding identification of a virtual care circle member to assign the task or item to, or responsibility for; and/or (b) generate and post an electronic notification detailing which virtual care circle member has been assigned the task or item to the care circle feed accessible via the mobile application running on one or more virtual care circle member mobile devices.

The digital care circle platform may be configured to, via one or more processors, sensors, servers, wearables, and/or transceivers: (i) receive or accept user input from a virtual care circle member via the mobile application regarding details of a task or item to add to the senior's virtual to-do list; (ii) add the task or item to the senior's virtual to-do list; and/or (iii) generate and post an electronic notification detailing the task or item to the care circle feed accessible via the mobile application running on one or more virtual care circle member mobile devices to facilitate coordinating key tasks among the members of the virtual care circle.

The digital care circle platform may be configured to, via one or more processors, sensors, servers, wearables, and/or transceivers: (i) receive user input from a virtual care circle member via the mobile application regarding identification of a virtual care circle member to assign the task or item to, or responsibility for; and/or (ii) generate and post an electronic notification detailing which virtual care circle member has been assigned the task or item to the care circle feed accessible via the mobile application running on one or more virtual care circle member mobile devices. The digital care circle platform may also be configured to, via one or more processors, sensors, servers, and/or transceivers: allow virtual care circle members to take or assign responsibility for various tasks or items in a virtual to-do list associated with the senior to facilitate collaborative scheduling and coordinating key tasks across the virtual care circle.

In another aspect, a computer-implemented method for electronic communication (i) within a virtual care circle, and (ii) between a senior's chatbot and application, and a mobile application running on multiple care circle members' respective mobile devices, the method may include, via one or more processors, servers, sensors, wearables, digital platforms, and/or transceivers configured for wireless communication and/or data transmission over one or more radio frequency links between and/or among the senior's chatbot and application, and the mobile application running on each virtual care circle member's mobile device: (1) receiving one or more one or more audible or verbal commands from the senior via the chatbot; (2) electronically interacting with and/or communicating with the chatbot via an application associated with a computing device of the senior; (3) electronically communicating with the senior's chatbot and application running on the senior's computing device via a mobile application running on each virtual care circle member's mobile device and associated with virtual care circle members, such as via wireless communication or data transmission over one or more radio frequency links; (4) electronically accepting or wirelessly receiving event posts from the senior via the chatbot and application, and from each virtual care circle member via the mobile device running on their respective mobile devices, such as via wireless communication or data transmission over one or more radio frequency links; (5) detecting pro-active check-ins that are automatically detected and/or generated by the senior verbally or audibly interacting with the chatbot and/or the senior accessing, viewing, or otherwise interacting with the application running on the senior's computing device; and/or (6) once a pro-active check-in is detected, generating an electronic communication detailing the pro-active check-in as a pro-active check-in event, and (a) automatically virtually posting the pro-active check-in event to a care circle feed access via the mobile application running on one or more virtual care circle member mobile devices, and/or (b) otherwise transmitting the electronic communication to the mobile application running on one or more virtual care circle member mobile devices to facilitate providing communication on the senior's current activity to the members of the virtual care circle and quick check-in functionality. The method may include additional, less, or alternate functionality, including that discussed elsewhere herein.

For instance, the computer-implemented method may include, via one or more processors, sensors, servers, wearables, and/or transceivers: actively monitoring use of, and/or interaction with, the chatbot, application, and/or computing device by the senior; detecting that the senior has not used or interacted with the chatbot, application, and/or computing device for a predetermined amount of time; and if so, automatically generating an electronic message to the senior, and transmitting or sending the electronic message to the chatbot, application, and/or computing device of the senior to facilitate quick check-ins and/or determining whether the senior needs assistance. The method may also include, via one or more processors, sensors, servers, wearables, and/or transceivers: when it is detected that the senior has not used or interacted with the chatbot, application, and/or computing device for a predetermined amount of time (such as 12 hours, 18 hours, 24 hours, 48 hours, etc.), automatically generating an electronic notification detailing such, and transmitting or otherwise sending the electronic notification to one or more virtual care circle member mobile devices to facilitate quick check-ins.

The computer-implemented method may include, via one or more processors, sensors, servers, wearables, and/or transceivers: actively monitoring use of, and/or interaction with, the chatbot, application, and/or computing device by the senior; detecting that the senior has not used or interacted with the chatbot, application, and/or computing device for a predetermined amount of time; when it is detected that the senior has not used or interacted with the chatbot, application, and/or computing device for a predetermined amount of time (e.g., 24 hours, 48 hours, etc.), automatically generating an electronic notification detailing such, and transmitting or otherwise sending the electronic notification to one or more virtual care circle member mobile devices; and/or opening, accessing, or creating an audible or verbal communication channel between the senior's chatbot and a virtual care circle member mobile device to facilitate a real-time conversation between the senior and the virtual care circle member, and/or quick check-ins.

The computer-implemented method may include, via one or more processors, sensors, servers, wearables, and/or transceivers: scanning or searching the internet for preferred content (music, videos, articles, events, activities, etc.) for the senior based the senior's preferences identified or detailed in a virtual profile associated with the senior; and/or pushing preferred content, or otherwise providing links thereto, to the senior's chatbot and/or the application running on the senior's computing device.

The computer-implemented method may include, via one or more processors, sensors, servers, wearables, and/or transceivers: generating a virtual calendar of scheduled events and/or activities for the senior, the virtual calendar including a scrolling list of scheduled events and/or activities; and displaying the virtual calendar of scheduled events and/or activities for the senior via the application on a display screen of the senior's computing device, and/or audibly or verbally detailing the calendar of scheduled events and/or activities for the senior via the chatbot.

The computer-implemented method may include, via one or more processors, sensors, servers, wearables, and/or transceivers: receiving audible or verbal commends from the senior via the chatbot regarding details of an event or activity to add to their virtual calendar; and/or adding the event or activity to the senior's virtual calendar.

The computer-implemented method may include, via one or more processors, sensors, servers, wearables, and/or transceivers: receiving or accepting audible or verbal commends from the senior via the chatbot regarding details of a task or item to add to their virtual to-do list; adding the task or item to the senior's virtual to-do list; and/or generating and posting an electronic notification detailing the task or item to the care circle feed accessible via the mobile application running on one or more virtual care circle member mobile devices to facilitate coordinating key tasks among the members of the virtual care circle. The method may include, via one or more processors, sensors, servers, wearables, and/or transceivers: receiving or accepting audible or verbal commands from the senior via the chatbot regarding identification of a virtual care circle member to assign the task or item to, or responsibility for; and/or generating and posting an electronic notification detailing which virtual care circle member has been assigned the task or item to the care circle feed accessible via the mobile application running on one or more virtual care circle member mobile devices.

The computer-implemented method may include, via one or more processors, sensors, servers, wearables, and/or transceivers: receiving or accepting user input from a virtual care circle member via the mobile application regarding details of a task or item to add to the senior's virtual to-do list; adding the task or item to the senior's virtual to-do list; and/or generating and posting an electronic notification detailing the task or item to the care circle feed accessible via the mobile application running on one or more virtual care circle member mobile devices to facilitate coordinating key tasks among the members of the virtual care circle. The method may include, via one or more processors, sensors, servers, wearables, and/or transceivers: receiving or accepting user input from a virtual care circle member via the mobile application regarding identification of a virtual care circle member to assign the task or item to, or responsibility for; and/or generating and posting an electronic notification detailing which virtual care circle member has been assigned the task or item to the care circle feed accessible via the mobile application running on one or more virtual care circle member mobile devices.

The method may also include, via one or more processors, sensors, servers, wearables, and/or transceivers: allowing virtual care circle members to take or assign responsibility for various tasks or items in a virtual to-do list associated with the senior to facilitate collaborative scheduling and coordinating key tasks across the virtual care circle.

Additional Considerations

With the foregoing, users and caregivers may opt-in or register to a care coordination support platform program or other type of program. After the users and caregivers give their affirmative consent or permission, a care coordination support platform remote server may collect data from the mobile devices, user computing devices, smart home controllers, smart vehicles, autonomous or semi-autonomous vehicles, smart infrastructure, smart buildings, smart aerial devices (e.g., drones), and/or other smart devices, such as with the permission or affirmative consent of the users and caregivers. The data collected may be related to user activities and/or user/caregiver schedules and current locations.

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an exemplary embodiment, the system is executed on a single computer system, without requiring a connection to a sever computer. In a further embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes.

In some embodiments, registration of users for the care coordination support platform includes opt-in informed consent of users to data usage by the smart home devices, wearable devices, mobile devices, autonomous vehicles, and/or smart vehicles consistent with consumer protection laws and privacy regulations. In some embodiments, the user data, the caregiver data, and/or other collected data may be anonymized and/or aggregated prior to receipt such that no personally identifiable information (PII) is received. In other embodiments, the system may be configured to receive user and caregiver data and/or other collected data that is not yet anonymized and/or aggregated, and thus may be configured to anonymize and aggregate the data. In such embodiments, any PII received by the system is received and processed in an encrypted format, or is received with the consent of the individual with which the PII is associated. In situations in which the systems discussed herein collect personal information about individuals, or may make use of such personal information, the individuals may be provided with an opportunity to control whether such information is collected or to control whether and/or how such information is used. In addition, certain data may be processed in one or more ways before it is stored or used, so that personally identifiable information is removed.

As used herein, an element or step recited in the singular and proceeded with the word "a" or "an" should be understood as not excluding plural elements or steps, unless such exclusion is explicitly recited. Furthermore, references to "exemplary embodiment" or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An engagement and care support platform ("ECSP") computer device comprising at least one processor in communication with at least one memory device, wherein the at least one processor of the ECSP computer device is programmed to:

receive input data associated with a plurality of user interactions of a senior user with a chatbot, the input data received via audio commands and one or more smart devices;

generate a user activity message summarizing a first user interaction of the plurality of user interactions, the user activity message identifying at least a type of the user interaction with at least one of the chatbot or the one or more smart devices and including one or more virtual to-do items that the senior user has verbally assigned to a caregiver; and transmit the user activity message to a caregiver client device associated with the caregiver, wherein the user activity message causes the caregiver client device to generate voice-based reminders associated with the virtual to-do items assigned to the caregiver.

2. The ECSP computer device of claim 1, wherein the at least one processor is further programmed to receive an indication, from a first smart device of the one or more smart devices, that the senior user interacted with the first smart device.

3. The ECSP computer device of claim 2, wherein the indication from the first smart device includes sensor information collected by the first smart device.

4. The ECSP computer device of claim 1, wherein the at least one processor is further programmed to:

generate a second user activity message summarizing a second user interaction of the plurality of user interactions with the chatbot or a smart device of the one or more smart devices, the second user activity message identifying at least a type of the second user interaction with the chatbot or the smart device; and transmit the second user activity message to the caregiver client device, wherein the second user activity message causes the caregiver client device to display at least the type of the second user interaction.

5. The ECSP computer device of claim 4, wherein the type of the first user interaction is different from the type of the second user interaction.

6. The ECSP computer device of claim 1, wherein the at least one processor is further programmed to:

receive second input data associated with an additional plurality of user interactions of the senior user with the chatbot, the second input data received via second audio commands and the one or more smart devices;

generate an additional user activity message summarizing an additional user interaction of the additional plurality of user interactions of the senior user with at least one of the chatbot or the one or more smart devices; and transmit the additional user activity message to the caregiver client device, wherein the additional user activity message causes the caregiver client device to display at least the type of the additional user interaction.

7. The ECSP computer device of claim 1, wherein the user activity message includes a device that the senior user interacted with.

8. The ECSP computer device of claim 7, wherein a first smart device that the senior user interacted with is an Internet of Things device.

9. The ECSP computer device of claim 1, wherein the at least one processor is further programmed to cause a user activity page to be displayed on a user interface of the caregiver client device, wherein the user activity page includes a summary of recent user-initiated interactions with the chatbot and the one or more smart devices.

10. The ECSP computer device of claim 1, wherein the at least one processor is further programmed to cause a virtual button to be displayed on a user interface of the caregiver client device, wherein when selected the virtual button at least one of initiates a video call, a phone call, or a text message from the caregiver client device to a client device associated with the senior user.

11. The ECSP computer device of claim 1, wherein the at least one processor is further programmed to:

determine a frequency of interactions of the senior user with the chatbot and the one or more smart devices; and transmit, to the caregiver client device, one or more notifications including the frequency of the interactions, wherein the frequency is caused to be displayed on a user interface of the caregiver client device.

12. The ECSP computer device of claim 1, wherein the at least one processor is further programmed to execute the chatbot to audibly interact with the senior user using plain language, wherein the chatbot receives an input signal captured by a microphone, interprets the input signal, generates an audio plain language response to the interpreted input signal, and responds with the audio plain language response via a speaker.

13. An engagement and care support platform ("ECSP") computer system comprising at least one processor in communication with at least one memory device, wherein the at least one processor of the ECSP computer system is programmed to:

receive input data associated with a plurality of user interactions of a senior user with a chatbot, the input data received via audio commands and one or more smart devices;

generate a user activity message summarizing a first user interaction of the plurality of user interactions, the user activity message identifying at least a type of the user interaction with at least one of the chatbot or the one or more smart devices and including one or more virtual to-do items that the senior user has verbally assigned to a caregiver;

and transmit the user activity message to a caregiver client device associated with the caregiver, wherein the user activity message causes the caregiver client device to generate voice-based reminders associated with the virtual to-do items assigned to the caregiver.

14. The ECSP computer system of claim 13, wherein the at least one processor is further programmed to receive an indication, from a first smart device of the one or more smart devices, that the senior user interacted with the first smart device, wherein the indication from the first smart device includes sensor information collected by the first smart device.

15. The ECSP computer system of claim 13, wherein the at least one processor is further programmed to:

generate a second user activity message summarizing a second user interaction of the plurality of user interactions with the chatbot or a smart device of the one or more smart devices, the second user activity message identifying at least a type of the second user interaction with the chatbot or the smart device; and transmit the second user activity message to the caregiver client device, wherein the second user activity message causes the caregiver client device to display at least the type of the second user interaction.

16. The ECSP computer system of claim 13, wherein the at least one processor is further programmed to cause a user activity page to be displayed on a user interface of the caregiver client device, wherein the user activity page includes a summary of recent user-initiated interactions with the chatbot and the one or more smart devices.

17. The ECSP computer system of claim 13, wherein the at least one processor is further programmed to cause a virtual button to be displayed on a user interface of the caregiver client device, wherein when selected the virtual button at least one of initiates a video call, a phone call, or a text message from the caregiver client device to a client device associated with the senior user.

18. The ECSP computer system of claim 13, wherein the at least one processor is further programmed to:

determine a frequency of interactions of the senior user with the chatbot and the one or more smart devices; and transmit, to the caregiver client device, one or more notifications including the frequency of the interactions, wherein the frequency is caused to be displayed on a user interface of the caregiver client device.

19. The ECSP computer system of claim 13, wherein the at least one processor is further programmed to execute the chatbot to audibly interact with the senior user using plain language, wherein the chatbot receives an input signal captured by a microphone, interprets the input signal, generates an audio plain language response to the interpreted input signal, and responds with the audio plain language response via a speaker.

20. A computer-implemented method for facilitating senior user engagement, the computer-implemented method performed by an engagement and care support platform ("ECSP") computer system comprising at least one processor in communication with at least one memory device, the computer-implemented method comprising:

receiving input data associated with a plurality of user interactions of a senior user with a chatbot, the input data received via audio commands and one or more smart devices;

generating a user activity message summarizing a first user interaction of the plurality of user interactions, the user activity message identifying at least a type of the user interaction with at least one of the chatbot or the one or more smart devices and including one or more virtual to-do items that the senior user has verbally assigned to a caregiver; and transmitting the user activity message to a caregiver client device associated with the caregiver, wherein the user activity message causes the caregiver client device to generate voice-based reminders associated with the virtual to-do items assigned to the caregiver.

* * * * *